US007259151B2

(12) United States Patent
Arbetman et al.

(10) Patent No.: US 7,259,151 B2
(45) Date of Patent: Aug. 21, 2007

(54) AAV VIRIONS WITH DECREASED IMMUNOREACTIVITY AND USES THEREFOR

(75) Inventors: Alejandra Elena Arbetman, San Francisco, CA (US); Peter C. Colosi, Alameda, CA (US); Michael A. Lochrie, Hayward, CA (US); Richard T. Surosky, Oakland, CA (US)

(73) Assignee: Genzyme Corporation, Framingham, MA (US)

( * ) Notice: Subject to any disclaimer, the term of this patent is extended or adjusted under 35 U.S.C. 154(b) by 0 days.

(21) Appl. No.: 10/873,632

(22) Filed: Jun. 21, 2004

(65) Prior Publication Data

US 2006/0051333 A1 Mar. 9, 2006

Related U.S. Application Data

(60) Provisional application No. 60/576,501, filed on Jun. 3, 2004, provisional application No. 60/567,310, filed on Apr. 30, 2004, provisional application No. 60/480,395, filed on Jun. 19, 2003.

(51) Int. Cl.

*A61K 31/715* (2006.01)
*A61K 39/23* (2006.01)
*A61K 48/00* (2006.01)

(52) U.S. Cl. ..................... 514/44; 424/93.2; 424/233.1

(58) Field of Classification Search ..................... None

See application file for complete search history.

(56) References Cited

U.S. PATENT DOCUMENTS 6,733,757 B2 5/2004 Patel et al.
2002/0192823 A1 12/2002 Bartlett
2003/0053990 A1 3/2003 Rabinowitz et al.

OTHER PUBLICATIONS

Wu, et al. Mutational analysis of the Adeno-associated Virus Type 2 (AAV2) Capsid Gene and Construction of AAV2 Vectors with Altered Tropism:, Journal of Virology, 74(18):8635-8647 (2000).*

Arbetman et al.; "Novel Caprine Adeno-Associated Virus (AAV) Capsid (AAV-Go.I) Is Closely Related to the Primate AAV-5 and Has Unique Tropism and Neutralization Properties," Journal of virology, 79(24):15238-15245 (2005).

Lochrie et al., "Mutations on the External Surfaces of Adeno-Associated Virus Type 2 Capsids That Effect Transduction and Neutralization," Journal of virology, 80(2):821-834 (2006).

Wu et al., "Mutational Analysis of the Adeno-Associated Virus Type 2 (AAV2) Capsid Gene and Construction of AAV2 Vectors With Altered Tropism," Journal of virology, 74(18):8635-8647 (2000).

Gao et al., "Novel Adeno-Associated Viruses From Rhesus Monkeys as Vectors for Human Gene Therapy", *PNAS*, 99(18):11854-11859 (2002).

(Continued)

*Primary Examiner*—Bruce R. Campell
*Assistant Examiner*—Stuart W. Snyder
(74) *Attorney, Agent, or Firm*—Robins & Pasternak LLP

(57) ABSTRACT

Methods of making and using recombinant AAV virions with decreased immunoreactivity are described. The recombinant AAV virions include mutated capsid proteins or are derived from non-primate mammalian AAV serotypes and isolates that display decreased immunoreactivity relative to AAV-2.

24 Claims, 36 Drawing Sheets

OTHER PUBLICATIONS

Halbert et al., "Successful Readministration of Adeno-Associated Virus Vectors to the Mouse Lung Requires Transient Immunosuppression During the Initial Exposure", *J. Virol.*, 72(12):9795-9805 (1998).

Huttner et al., "Genetic Modifications of the Adeno-Associated Virus Type 2 Capsid Reduce the Affinity and the Neutralizing Effects of Human Serum Antibodies", *Gene Therapy*, 10:2139-2147 (2003).

Moskalenko et al., "Epitope Mapping of Human Anti-Adeno-Associated Virus Type 2 Neutralizing Antibodies: Implications for Gene Therapy and Virus Structure", *J. Virol.*, 74(4):1761-1766 (2000).

Opie et al., "Identification of Amino Acid Residues in the Capsid Proteins of Adeno-Associated Virus Type 2 That Contribute to Heparan Sulfate Proteoglycan Binding", *J. Virol.*, 77(12):6995-7006 (2003).

Schmidt et al., "Cloning and Characterization of a Bovine Adeno-Associated Virus",*J. Virol.*, 78(12):6509-6516 (2004).

Lochrie, et al., "Mutation of 53 Amino Acids on the Surface of Adeno-Associated Virus Type-2." *Molecular Therapy* May 2003, vol.7, No.5, part 2, p. S40, Abstract No. 100.

Lochrie, et al., Effect of 127 Mutations at 72 positions on the surface of adeno-associated virus type-2. *Molecular Therapy* May 2004, vol. 9, Supplement 1, p. S286, Abstract No. 752.

* cited by examiner

| | |
|---|---|
| 1 | MAPGKKRPVEHSPVEPDSSSGTGKAGQQPARKRLNFGQTGDADSVPDPQPLGQPPAAP |
| 59 | SGLGTNTMATGSGAPMADNNEGADGVGNSSGNWHCDSTWMGDRVITTSTRTWALPTYN |
| 117 | NHLYKQISSQSGASNDNHYFGYSTPWGYFDFNRFHCHFSPRDWQRLINNNWGFRPKRL |
| 175 | NFKLFNIQVKEVTQNDGTTTIANNLTSTVQVFTDSEYQLPYVLGSAHQGCLPPFPADV |
| 233 | FMVPQYGYLTLNNGSQAVGRSSFYCLEYFPSQMLRTGNNFTFSYTFEDVPFHSSYAHS |
| 291 | QSLDRLMNPLIDQYLYYLSRTNTPSGTTTQSRLQFSQAGASDIRDQSRNWLPGPCYRQ |
| 349 | QRVSKTSADNNNSEYSWTGATKYHLNGRDSLVNPGPAMASHKDDEEKFFPQSGVLIFG |
| 407 | KQGSEKTNVDIEKVMITDEEEIRTTNPVATEQYGSVSTNLQRGNRQAATADVNTQGVL |
| 465 | PGMVWQDRDVYLQGPIWAKIPHTDGHFHPSPLMGGFGLKHPPPQILIKNTPVPANPST |
| 523 | TFSAAKFASFITQYSTGQVSVEIEWELQKENSKRWNPEIQYTSNYNKSVNVDFTVDTN |
| 581 | GVYSEPRPIGTRYLTRNL |

FIGURE 9

```
  1 maadgylpdw ledtlsegir qwwklkpgpp ppkpaerhkd dsrglvlpgy kylgpfngld
 61 kgepvneada aalehdkayd rqldsgdnpy lkynhadaef qerlkedtsf ggnlgravfq
121 akkrvleplg lveepvktap gkkrpvehsp vepdsssgtg kagqqparkr lnfgqtgdad
181 svpdpqplgq ppaapsglgt ntmatgsgap madnnegadg vgnssgnwhc dstwmgdrvi
241 ttstrtwalp tynnhlykqi ssqsgasndn hyfgystpwg yfdfnrfhch fsprdwqrli
301 nnnwgfrpkr lnfklfniqv kevtqndgtt tiannltstv qvftdseyql pyvlgsahqg
361 clppfpadvf mvpqygyltl nngsqavgrs sfycleyfps qmlrtgnnft fsytfedvpf
421 hssyahsqsl drlmnplidq ylyylsrtnt psgtttqsrl qfsqagasdi rdqsrnwlpg
481 pcyrqqrvsk tsadnnnsey swtgatkyhl ngrdslvnpg pamashkdde ekffpqsgvl
541 ifgkqgsekt nvdiekvmit deeeirttnp vateqygsvs tnlqrgnrqa atadvntqgv
601 lpgmvwqdrd vylqgpiwak iphtdghfhp splmggfglk hpppqilikn tpvpanpstt
661 fsaakfasfi tqystgqvsv eiewelqken skrwnpeiqy tsnynksvnv dftvdtngvy
721 seprpigtry ltrnl
```

FIGURE 10

| | | |
|---|---|---|
| | VP1 | |
| Primate AAV type 5 | <u>atg</u>tcttttgttgatcaccctccagattggttggaagaagttgg | 2250 |
| Caprine AAV | ............................................ | |
| Primate AAV type 5 | tgaaggtcttcgcgagtttttgggcctgaagcgggcccaccgaaaccaa | 2300 |
| Caprine AAV | .................................................. | |
| Primate AAV type 5 | aacccaatcagcagcatcaagatcaagcccgtggtcttgtgctgcctggt | 2350 |
| Caprine AAV | .................................................. | |
| Primate AAV type 5 | tataactatctcggacccggaaacggtctcgatcgaggagagcctgtcaa | 2400 |
| Caprine AAV | .................................................. | |
| Primate AAV type 5 | cagggcagacgaggtcgcgcgagagcacgacatctcgtacaacgagcagc | 2450 |
| Caprine AAV | .................................................. | |
| Primate AAV type 5 | ttgaggcgggagacaacccctacctcaagtacaaccacgcggacgccgag | 2500 |
| Caprine AAV | .................................................. | |
| Primate AAV type 5 | tttcaggagaagctcgccgacgacacatccttcgggggaaacctcggaaa | 2550 |
| Caprine AAV | .................................................. | |
| Primate AAV type 5 | ggcagtctttcaggccaagaaaagggttctcgaaccttttggcctggttg | 2600 |
| Caprine AAV | .................................................. | |
| Primate AAV type 5 | aagagggtgctaagacggcccctaccggaaagcggatagacgaccacttt | 2650 |
| Caprine AAV | .................................................. | |
| Primate AAV type 5 | ccaaaaagaaagaaggctcggaccgaagaggactccaagccttccacctc | 2700 |
| Caprine AAV | .................................................. | |
| Primate AAV type 5 | gtcagacgccgaagctggacccagcggatcccagcagctgcaaatcccag | 2750 |
| Caprine AAV | .................................................. | |
| Primate AAV type 5 | cccaaccagcctcaagtttgggagctgatacaatgtctgcgggaggtggc | 2800 |
| Caprine AAV | .a................................................ | |
| Primate AAV type 5 | ggcccattgggcgacaataaccaaggtgccgatggagtgggcaatgcctc | 2850 |
| Caprine AAV | .................................................. | |
| Primate AAV type 5 | gggagattggcattgcgattccacgtggatggggacagagtcgtcacca | 2900 |
| Caprine AAV | .................................................. | |
| Primate AAV type 5 | agtccacccgaacctgggtgctgcccagctacaacaaccaccagtaccga | 2950 |
| Caprine AAV | ..........c....................................... | |
| Primate AAV type 5 | gagatcaaaagcggctccgtcgacggaagcaacgccaacgcctactttgg | 3000 |
| Caprine AAV | .................................................. | |
| Primate AAV type 5 | atacagcacccccctggggtactttgactttaaccgcttccacagccact | 3050 |
| Caprine AAV | .................................................. | |
| Primate AAV type 5 | ggagcccccgagactggcaaagactcatcaacaactactggggcttcaga | 3100 |
| Caprine AAV | .....................................t............ | |
| Primate AAV type 5 | ccccggtccctcagagtcaaaatcttcaacattcaagtcaaagaggtcac | 3150 |
| Caprine AAV | ........t.......................c................. | |
| Primate AAV type 5 | ggtgcaggactccaccaccaccatcgccaacaacctcacctccaccgtcc | 3200 |
| Caprine AAV | .................................................. | |
| Primate AAV type 5 | aagtgtttacggacgacgactaccagctgccctacgtcgtcggcaacggg | 3250 |
| Caprine AAV | .........................a..c..g.................. | |
| Primate AAV type 5 | accgagggatgcctgccggccttccctccgcaggtctttacgctgccgca | 3300 |
| Caprine AAV | ..........................c....................... | |

FIGURE 12A

| | | |
|---|---|---|
| Primate AAV type 5 | gtacggttacgcgacgctgaaccgcgacaacacagaaaatcccaccgaga | 3350 |
| Caprine AAV | ......c.................a......gg...c..c..g..a...c | |
| Primate AAV type 5 | ggagcagcttcttctgcctagagtactttcccagcaagatgctgagaacg | 3400 |
| Caprine AAV | .............t................................g... | |
| Primate AAV type 5 | ggcaacaactttgagtttacctacaactttgaggaggtgcccttccactc | 3450 |
| Caprine AAV | .........................g......a................g | |
| Primate AAV type 5 | cagcttcgctcccagtcagaacctgttcaagctggccaacccgctggtgg | 3500 |
| Caprine AAV | .........c..g..c........c..t...................... | |
| Primate AAV type 5 | accagtacttgtaccgcttcgtgagcacaaataacactggcggagtccag | 3550 |
| Caprine AAV | ........c...................ctcggc...g....cca..... | |
| Primate AAV type 5 | ttcaacaagaacctggccgggagatacgccaacacctacaaaaactggtt | 3600 |
| Caprine AAV | ...c.a...........g..c............................. | |
| Primate AAV type 5 | cccggggcccatgggccgaacccagggctggaacctgggctccggggtca | 3650 |
| Caprine AAV | ..................................ac.a...t..    .. | |
| Primate AAV type 5 | accgcgc---cagtgtcagcgccttcgccacgacc------aataggatg | 3691 |
| Caprine AAV | g.a..a.caa...a.......t.aa.aa.tttt..gtctca..cc..... | |
| Primate AAV type 5 | gagctcgagggcgcgagttaccaggtgcccccgcagccgaacggcatgac | 3741 |
| Caprine AAV | a.c..g.....g..c..c.....a...aa...c.....c.....g..... | |
| Primate AAV type 5 | caacaacctccagggcagcaacacctatgccctggagaacactatgatct | 3791 |
| Caprine AAV | a....cg.....a.........cg...c..g.....a.....c....... | |
| Primate AAV type 5 | tcaacagccagccggcgaacccgggcaccaccgccacgtacctcgagggc | 3841 |
| Caprine AAV | .....gct..aaac..c.cg....a..t...t.ggt......ca....a. | |
| Primate AAV type 5 | aacatgctcatcaccagcgagagcgagacgcagccggtgaaccgcgtggc | 3891 |
| Caprine AAV | ..tc.a..gc.g...................t....c..c....g..... | |
| Primate AAV type 5 | gtacaacgtcggcgggcagatggccaccaacaaccagagctccaccactg | 3941 |
| Caprine AAV | t.....acg....t.................gc.....a.g.......g. | |
| Primate AAV type 5 | cccccgcgaccggcacgtacaacctccaggaaatcgtgcccggcagcgtg | 3991 |
| Caprine AAV | .t...a..gt...g..c...............g.gc.t..t........a | |
| Primate AAV type 5 | tggatggagagggacgtgtacctccaaggacccatctgggccaagatccc | 4041 |
| Caprine AAV | .................................................. | |
| Primate AAV type 5 | agagacgggggcgcactttcacccctctccggccatgggcggattcggac | 4091 |
| Caprine AAV | .................................................. | |
| Primate AAV type 5 | tcaaacacccaccgcccatgatgctcatcaagaacacgcctgtgcccgga | 4141 |
| Caprine AAV | ..........g....................a........g........c | |
| Primate AAV type 5 | aatatcaccagcttctcggacgtgcccgtcagcagcttcatcacccagta | 4191 |
| Caprine AAV | ..c............................................... | |
| Primate AAV type 5 | cagcaccgggcaggtcaccgtggagatggagtgggagctcaagaaggaaa | 4241 |
| Caprine AAV | ..............................a...........a....... | |
| Primate AAV type 5 | actccaagaggtggaacccagagatccagtacacaaacaactacaacgac | 4291 |
| Caprine AAV | ..................................c............... | |
| Primate AAV type 5 | ccccagtttgtggactttgccccggacagcaccggggaatacagaaccac | 4341 |
| Caprine AAV | ....................t..a...g..t....c.............. | |
| Primate AAV type 5 | cagacctatcggaacccgataccttacccgacccctt | 4378 |
| Caprine AAV | ....g.c.................c............ | |

FIGURE 12B

```
Primate AAV type 5 VP1 MSFVDHPPDWLEEVGEGLREFLGLEAGPPKPKPNQQHQDQARGLVLPGYNYLGPGNGLDR 60
Caprine AAV VP1       ............................................................ 60

Primate AAV type 5 VP1 GEPVNRADEVAREHDISYNEQLEAGDNPYLKYNHADAEFQEKLADDTSFGGNLGKAVFQA 120
Caprine AAV VP1       ............................................................ 120

Primate AAV type 5 VP1 KKRVLEPFGLVEEGAKTAPTGKRIDDHFPKRKKARTEEDSKPSTSSDAEAGPSGSQQLQI 180
Caprine AAV VP1       ............................................................ 180

Primate AAV type 5 VP1 PAQPASSLGADTMSAGGGGPLGDNNQGADGVGNASGDWHCDSTWMGDRVVTKSTRTWVLP 240
Caprine AAV VP1       ............................................................ 240

Primate AAV type 5 VP1 SYNNHQYREIKSGSVDGSNANAYFGYSTPWGYFDFNRFHSHWSPRDWQRLINNYWGFRPR 300
Caprine AAV VP1       ............................................................ 300

Primate AAV type 5 VP1 SLRVKIFNIQVKEVTVQDSTTTIANNLTSTVQVFTDDDYQLPYVVGNGTEGCLPAFPPQV 360
Caprine AAV VP1       ............................................................ 360

Primate AAV type 5 VP1 FTLPQYGYATLNRDNTENPTERSSFFCLEYFPSKMLRTGNNFEFTYNFEEVPFHSSFAPS 420
Caprine AAV VP1       ...............GD.........................S.......G..... 420

Primate AAV type 5 VP1 QNLFKLANPLVDQYLYRFVSTNNTGGVQFNKNLAGRYANTYKNWFPGPMGRTQGWNLGSG 480
Caprine AAV VP1       .....................SA..AI..Q..........................TS.. 480

Primate AAV type 5 VP1 --VNRASVSAFATTNRMELEGASYQVPPQPNGMTNNLQGSNTYALENTMIFNSQPANPGT 538
Caprine AAV VP1       SST..V..NN.SVS...N........N........T.....R...........A.N.T... 540

Primate AAV type 5 VP1 TATYLEGNMLITSESETQPVNRVAYNVGGQMATNNQSSTTAPATGTYNLQEIVPGSVWME 598
Caprine AAV VP1       .SV.P.S.L.L...............T.......A.NA....TV.......VL....... 600

Primate AAV type 5 VP1 RDVYLQGPIWAKIPETGAHFHPSPAMGGFGLKHPPPMMLIKNTPVPGNITSFSDVPVSSF 658
Caprine AAV VP1       ............................................................ 660

Primate AAV type 5 VP1 ITQYSTGQVTVEMEWELKKENSKRWNPEIQYTNNYNDPQFVDFAPDSTGEYRTTRPIGTR 718
Caprine AAV VP1       ..............................................GS.......A.... 720

Primate AAV type 5 VP1 YLTRPL 724
Caprine AAV VP1       ...... 726
```

FIG. 13

```
                                                               VP1 VP2
      AAV-2 VP1:MAADGYLPDW LEDTLSEGIR QWWKLKPGPP PPKPAERHKD DSRGLVLPGY  50
     AAV-3B VP1:MAADGYLPDW LEDNLSEGIR EWWALKPGVP QPKANQQHQD NRRGLVLPGY
      AAV-6 VP1:MAADGYLPDW LEDNLSEGIR EWWDLKPGAP KPKANQQKQD DGRGLVLPGY
      AAV-1 VP1:MAADGYLPDW LEDNLSEGIR EWWDLKPGAP KPKANQQKQD DGRGLVLPGY
      AAV-8 VP1:MAADGYLPDW LEDNLSEGIR EWWALKPGAP KPKANQQKQD DGRGLVLPGY
      AAV-4 VP1:M-TDGYLPDW LEDNLSEGVR EWWALQPGAP KPKANQQHQD NARGLVLPGY
      AAV-5 VP1:MSFVDHPPDW LEE-VGEGLR EFLGLEAGPP KPKPNQQHQD QARGLVLPGY
Caprine AAV VP1:MSFVDHPPDW LEE-VGEGLR EFLGLEAGPP KPKPNQQHQD QARGLVLPGY
   Parvoviruses:*
         Other:                                               PPPPPPP

      AAV-2 VP1:KYLGPFNGLD KGEPVNEADA AALEHDKAYD RQLDSGDNPY LKYNHADAEF  100
     AAV-3B VP1:KYLGPGNGLD KGEPVNEADA AALEHDKAYD QQLKAGDNPY LKYNHADAEF
      AAV-6 VP1:KYLGPFNGLD KGEPVNAADA AALEHDKAYD QQLKAGDNPY LRYNHADAEF
      AAV-1 VP1:KYLGPFNGLD KGEPVNAADA AALEHDKAYD QQLKAGDNPY LRYNHADAEF
      AAV-8 VP1:KYLGPFNGLD KGEPVNAADA AALEHDKAYD QQLQAGDNPY LRYNHADAEF
      AAV-4 VP1:KYLGPGNGLD KGEPVNAADA AALEHDKAYD QQLKAGDNPY LKYNHADAEF
      AAV-5 VP1:NYLGPGNGLD RGEPVNRADE VAREHDISYN EQLEAGDNPY LKYNHADAEF
Caprine AAV VP1:NYLGPGNGLD RGEPVNRADE VAREHDISYN EQLEAGDNPY LKYNHADAEF
   Parvoviruses:                   *      **  *                   *
         Other:PPPPPPPPPP PPPPPPPPPP PPPPPPPPPP PPPPPPPPPP PPPPPPPPPP
```

FIG. 14A

```
                                                                                           VP1  VP2
         AAV-2 VP1:QERLKEDTSF GGNLGRAVFQ AKKRVLEPLG LVEEPVKTAP GKKRPVEHSP  150   13
        AAV-3B VP1:QERLQEDTSF GGNLGRAVFQ AKKRILEPLG LVEEAAKTAP GKKRPVDQSP
         AAV-6 VP1:QERLQEDTSF GGNLGRAVFQ AKKRVLEPFG LVEEGAKTAP GKKRPVEQSP
         AAV-1 VP1:QERLQEDTSF GGNLGRAVFQ AKKRVLEPLG LVEEGAKTAP GKKRPVEQSP
         AAV-8 VP1:QERLQEDTSF GGNLGRAVFQ AKKRVLEPLG LVEEGAKTAP GKKRPVEPSP
         AAV-4 VP1:QQRLQGDTSF GGNLGRAVFQ AKKRVLEPLG LVEQAGETAP GKKRPLIESP
         AAV-5 VP1:QEKLADDTSF GGNLGKAVFQ AKKRVLEPFG LVEEGAKTAP TGKRIDDHFP
   Caprine AAV VP1:QEKLADDTSF GGNLGKAVFQ AKKRVLEPFG LVEEGAKTAP TGKRIDDHFP
             Other:PPPPPPPPPP PPPPPPPPPP PPPPPPPPPP PPPPP

         AAV-2 VP1:VE-PDSSSGTG KAGQQPARKR LNFGQTGDAD SVPDPQPLGQ PPAAP-SGLGT 200 63
        AAV-3B VP1:QE-PDSSSGVG KSGKQPARKR LNFGQTGDSE SVPDPQPLGE PPAAP-TSLGS
         AAV-6 VP1:QE-PDSSSGIG KTGQQPAKKR LNFGQTGDSE SVPDPQPLGE PPATP-AAVGP
         AAV-1 VP1:QE-PDSSSGIG KTGQQPAKKR LNFGQTGDSE SVPDPQPLGE PPATP-AAVGP
         AAV-8 VP1:QRSPDSSTGIG KKGQQPARKR LNFGQTGDSE SVPDPQPLGE PPAAP-SGVGP
         AAV-4 VP1:QQ-PDSSTGIG KKGKQPAKKK LVFEDETGAG DGPPEGSTSG AMSDD--S---
         AAV-5 VP1:----------- KRKKARTEED SKPSTSSDAE AGPSGSQQLQ IPAQPASSLGA
   Caprine AAV VP1:----------- KRKKARTEED SKPSTSSDAE AGPSGSQQLQ IPAQPASSLGA
```

FIG. 14B

```
                                                                                    VP1 VP2
                                   /AAV-2 capsid structure begins here.
       AAV-2 VP1:NTMATGSGAP MADNNEGADG VGNSSGNWHC DSTWMGDRVI TTSTRTWALP  250 113
       AAV-6 VP1:TTMASGGGAP MADNNEGADG VGNASGNWHC DSTWLGDRVI TTSTRTWALP
       AAV-1 VP1:TTMASGGGAP MADNNEGADG VGNASGNWHC DSTWLGDRVI TTSTRTWALP
       AAV-8 VP1:NTMAAGGGAP MADNNEGADG VGSSSGNWHC DSTWLGDRVI TTSTRTWALP
       AAV-4 VP1:-EMRAAAGGA AVEGGQGADG VGNASGDWHC DSTWSEGHVT TTSTRTWVLP
       AAV-5 VP1:DTMSAGGGGP LGDNNQGADG VGNASGDWHC DSTWMGDRVV TKSTRTWVLP
 Caprine AAV VP1:DTMSAGGGGP LGDNNQGADG VGNASGDWHC DSTWMGDRVV TKSTRTWVLP
   Parvoviruses:    *             * *                           *
  Accessibility:                  IIII IIIIIIIII IIIIIIIII IIIIBBBBBB
            DNA:                                R  P B
          Other:                                   M

       AAV-2 VP1:TYNNHLYKQI SSQS--GASNDN HYFGYSTPWG YFDFNRFHCH FSPRDWQRLI 300
163
      AAV-3B VP1:TYNNHLYKQI SSQS--GASNDN HYFGYSTPWG YFDFNRFHCH FSPRDWQRLI
       AAV-6 VP1:TYNNHLYKQI SSAST-GASNDN HYFGYSTPWG YFDFNRFHCH FSPRDWQRLI
       AAV-1 VP1:TYNNHLYKQI SSAST-GASNDN HYFGYSTPWG YFDFNRFHCH FSPRDWQRLI
       AAV-8 VP1:TYNNHLYKQI SNGTSGGATNDN TYFGYSTPWG YFDFNRFHCH FSPRDWQRLI
       AAV-4 VP1:TYNNHLYKRL GESL-----QSN TYNGFSTPWG YFDFNRFHCH FSPRDWQRLI
       AAV-5 VP1:SYNNHQYREI KSGSV-DGSNAN AYFGYSTPWG YFDFNRFHSH WSPRDWQRLI
 Caprine AAV VP1:SYNNHQYREI KSGSV-DGSNAN AYFGYSTPWG YFDFNRFHSH WSPRDWQRLI
   Parvoviruses:       *                        ***    * *         *   *
 Neutralization:                 #  # # #  #
  Accessibility:OOOOBOBOOO OBOO  OOOOOO OOBBBBBBBB BBBBBBBBBB BBBBBBBIBB
Surface Feature:YYYY Y YYY Y PP  PPPPPP PP
          Other:              AA
```

FIG. 14C

```
                                                                                     VP1 VP2
          AAV-2 VP1:NNNWGFRPKR LNFKLFNIQV KEVTQNDGTT TIANNLTSTV QVFTDSEYQL  350 213
         AAV-3B VP1:NNNWGFRPKK LSFKLFNIQV KEVTQNDGTT TIANNLTSTV QVFTDSEYQL
          AAV-6 VP1:NNNWGFRPKR LNFKLFNIQV KEVTTNDGVT TIANNLTSTV QVFSDSEYQL
          AAV-1 VP1:NNNWGFRPKR LNFKLFNIQV KEVTTNDGVT TIANNLTSTV QVFSDSEYQL
          AAV-8 VP1:NNNWGFRPKR LSFKLFNIQV KEVTQNEGTK TIANNLTSTI QVFTDSEYQL
          AAV-4 VP1:NNNWGMRPKA MRVKIFNIQV KEVTTSNGET TVANNLTSTV QIFADSSYEL
          AAV-5 VP1:NNYWGFRPRS LRVKIFNIQV KEVTVQDSTT TIANNLTSTV QVFTDDDYQL
    Caprine AAV VP1:NNYWGFRPRS LRVKIFNIQV KEVTVQDSTT TIANNLTSTV QVFTDDDYQL
       Parvoviruses:                      *                *         *
      Accessibility:IIBIBBIIII IIBIBIBBBB OOOOOOOOOO OOBIBIBBBB BBIIIIIIBB
    Surface Feature:                      CCCCCCCCCC CC
               DNA:    B     D BB                                PB D
             Other:                                              M

          AAV-2 VP1:PYVLGSAHQG CLPPFPADVF MVPQYGYLTL N--NGSQ-AVGRS SFYCLEYFPS 400
    263
         AAV-3B VP1:PYVLGSAHQG CLPPFPADVF MVPQYGYLTL N--NGSQ-AVGRS SFYCLEYFPS
          AAV-6 VP1:PYVLGSAHQG CLPPFPADVF MIPQYGYLTL N--NGSQ-AVGRS SFYCLEYFPS
          AAV-1 VP1:PYVLGSAHQG CLPPFPADVF MIPQYGYLTL N--NGSQ-AVGRS SFYCLEYFPS
          AAV-8 VP1:PYVLGSAHQG CLPPFPADVF MIPQYGYLTL N--NGSQ-AVGRS SFYCLEYFPS
          AAV-4 VP1:PYVMDAGQEG SLPPFPNDVF MVPQYGYCGL VTGNTSQQQTDRN AFYCLEYFPS
          AAV-5 VP1:PYVVGNGTEG CLPAFPPQVF TLPQYGYATL NRDNTEN-PTERS SFFCLEYFPS
    Caprine AAV VP1:PYVVGNGTEG CLPAFPPQVF TLPQYGYATL NRDNGDN-PTERS SFFCLEYFPS
       Parvoviruses:*                             *
      Accessibility:BIBBBBBBBB BBBBBBBBBB OBOOBBBBBB O  OOOOBBBBB BBBBBBBIII
    Surface Feature:                     Y YY       P  PPPP
             Other:                                     AA
```

FIG. 14D

```
                                                                                 VP1  VP2
       AAV-2 VP1:QMLRTGNNFT FSYTFEDVPF HSSYAHSQSL DRLMNPLIDQ YLYYLSRTN-T 450  313
      AAV-3B VP1:QMLRTGNNFQ FSYTFEDVPF HSSYAHSQSL DRLMNPLIDQ YLYYLNRTQGT
       AAV-6 VP1:QMLRTGNNFT FSYTFEDVPF HSSYAHSQSL DRLMNPLIDQ YLYYLNRTQ-N
       AAV-1 VP1:QMLRTGNNFT FSYTFEEVPF HSSYAHSQSL DRLMNPLIDQ YLYYLNRTQ-N
       AAV-8 VP1:QMLRTGNNFQ FTYTFEDVPF HSSYAHSQSL DRLMNPLIDQ YLYYLSRTQ-T
       AAV-4 VP1:QMLRTGNNFE ITYSFEKVPF HSMYAHSQSL DRLMNPLIDQ YLWGLQSTT-T
       AAV-5 VP1:KMLRTGNNFE FTYNFEEVPF HSSFAPSQNL FKLANPLVDQ YLYRFVSTN-N
 Caprine AAV VP1:KMLRTGNNFE FTYSFEEVPF HCSFAPSQNL FKLANPLVDQ YLYRFVSTS-A
    Parvoviruses:     *
   Accessibility: IIBBBIIII IIIIIIIIII BIBIBBIBOB OBBBBBOOOB BBBBBBOBB O
 Surface Feature:                            P  P     YYY         S   S
            DNA: P       B    BB D      D D

       AAV-2 VP1:PSGTTTQSRL QFSQAGASDI RDQSRNWLPG PCYRQQRVSK TSA-----DNNNSEY 500
363
      AAV-3B VP1:TSGTTNQSRL LFSQAGPQSM SLQARNWLPG PCYRQQRLSK TAN-----DNNNSNF
       AAV-6 VP1:QSGSAQNKDL LFSRGSPAGM SVQPKNWLPG PCYRQQRVSK TKT-----DNNNSNF
       AAV-1 VP1:QSGSAQNKDL LFSRGSPAGM SVQPKNWLPG PCYRQQRVSK TKT-----DNNNSNF
       AAV-8 VP1:TGGTANTQTL GFSQGGPNTM ANQAKNWLPG PCYRQQRVST TTG-----QNNNSNF
       AAV-4 VP1:TTLNAGTATT NFTKLRPTNF SNFKKNWLPG PSIKQQGFSK TANQNYKIPATGSDS
       AAV-5 VP1:TGG------V QFNKNLAGRY ANTYKNWFPG PMGRTQGWNL GSG-----VNRASVS
 Caprine AAV VP1:TGA------I QFQKNLAGRY ANTYKNWFPG PMGRTQGWNT SSGSSTNRVSVN
  Neutralization: #                    #                     #    #  #
   Accessibility:OOOOOOOOOB OBBBBOOOOB OOBBBBBBBB BBOOBBOOBO OOO  OBOOOOB
 Surface Feature:SSSSSSSSS  S    PPPP  PP            SS   SS S SSS  S SSSS
           Other:                                    H   H
```

FIG. 14E

```
                                                                                 VP1  VP2
          AAV-2 VP1:SWTGATKYHL NGRDSLVNPG PAMASHKDDE EKFFPQSGVL IFGKQGSEKT  550  413
         AAV-3B VP1:PWTAASKYHL NGRDSLVNPG PAMASHKDDE EKFFPMHGNL IFGKEGTTAS
          AAV-6 VP1:TWTGASKYNL NGRESIINPG TAMASHKDDK DKFFPMSGVM IFGKESAGAS
          AAV-1 VP1:TWTGASKYNL NGRESIINPG TAMASHKDDE DKFFPMSGVM IFGKESAGAS
          AAV-8 VP1:AWTAGTKYHL NGRNSLANPG IAMATHKDDE ERFFPSNGIL IFGKQNAARD
          AAV-4 VP1:LIKYETHSTL DGRWSALTPG PPMATAGPAD SKFSNSQLIF AGPKQNGNTA
          AAV-5 VP1:AFATTNRMEL EGASYQVPPQ PNGMTNNLQG SNTYALENTM IFNSQPANPG
    Caprine AAV VP1:NFSVSNRMNL EGASYQVNPQ PNGMTNTLQG SNRYALENTM IFNAQNATPG
     Neutralization: #      #   # #            #  # ###        #   # #
      Accessibility:BOOBBBOBOB OOBOBBBBBB BBBBBBOOOO OOOBBBBBBB BBBOOOBOOO
    Surface Feature: PP    P P  PP P           PPPP PSS           SSS SSS
              Other:                                 HH              A

          AAV-2 VP1:NVDI--E-KVMIT DEEEIRTTNP VATEQYGSVS TNLQRGNRQA ATADVNTQGV 600
  463
         AAV-3B VP1:NAEL---DNVMIT DEEEIRTTNP VATEQYGTVA NNLQSSNTAP TTRTVNDQGA
          AAV-6 VP1:NTAL---DNVMIT DEEEIKATNP VATERFGTVA VNLQSSSTDP ATGDVHVMGA
          AAV-1 VP1:NTAL---DNVMIT DEEEIKATNP VATERFGTVA VNFQSSSTDP ATGDVHAMGA
          AAV-8 VP1:NADY---SDVMLT SEEEIKTTNP VATEEYGIVA DNLQQQNTAP QIGTVNSQGA
          AAV-4 VP1:TVPG----TLIFT SEEELAATNA TDTDMWGNLP GGDQSNSNLP TVDRLTALGA
          AAV-5 VP1:TTATYLEGNMLIT SESETQPVNR VAYNVGGQMA TNNQSSTTAP ATGTYNLQEI
    Caprine AAV VP1:TTSVYPEDNLLLT SESETQPVNR VAYNTGGQMA TNAQNATTAP TVGTYNLQEV
     Neutralization:     #                      #          ##
      Accessibility:OOOO  O OOBOB OBOOBOBBBB BBBOOBBOBB OOOBOOOOOB OOOOBOOOBB
    Surface Feature:SSSS  S SS S  Y YY Y       PP  P    SSS SSSSS  PPPP PPP
              Other:                                      H H  H
```

FIG. 14F

```
                                                               VP1 VP2
      AAV-2 VP1:LPGMVWQDRD VYLQGPIWAK IPHTDGHFHP SPLMGGFGLK HPPPQILIKN 650 513
     AAV-3B VP1:LPGMVWQDRD VYLQGPIWAK IPHTDGHFHP SPLMGGFGLK HPPPQIMIKN
      AAV-6 VP1:LPGMVWQDRD VYLQGPIWAK IPHTDGHFHP SPLMGGFGLK HPPPQILIKN
      AAV-1 VP1:LPGMVWQDRD VYLQGPIWAK IPHTDGHFHP SPLMGGFGLK NPPPQILIKN
      AAV-8 VP1:LPGMVWQNRD VYLQGPIWAK IPHTDGNFHP SPLMGGFGLK HPPPQILIKN
      AAV-4 VP1:VPGMVWQNRD IYYQGPIWAK IPHTDGHFHP SPLIGGFGLK HPPPQIFIKN
      AAV-5 VP1:VPGSVWMERD VYLQGPIWAK IPETGAHFHP SPAMGGFGLK HPPPMMLIKN
Caprine AAV VP1:LPGSVWMERD VYLQGPIWAK IPETGAHFHP SPAMGGFGLK HPPPMMLIKN
   Parvoviruses:*                *  *                         *     *
  Accessibility:BBBBBIIBBO BBBBBBIBBI IBIIIIIIII IBBBBBBBII IIIIBBBBBB
Surface Feature:         S
            DNA:                   P         B          BB B

      AAV-2 VP1:TPVPANPSTT FSAAKFASFI TQYSTGQVSV EIEWELQKEN SKRWNPEIQY 700 563
     AAV-3B VP1:TPVPANPPTT FSPAKFASFI TQYSTGQVSV EIEWELQKEN SKRWNPEIQY
      AAV-6 VP1:TPVPANPPAE FSATKFASFI TQYSTGQVSV EIEWELQKEN SKRWNPEVQY
      AAV-1 VP1:TPVPANPPAE FSATKFASFI TQYSTGQVSV EIEWELQKEN SKRWNPEVQY
      AAV-8 VP1:TPVPANPSTT FSAAKFASFI TQYSTGQVSV EIEWELQKEN SKRWNPEIQY
      AAV-4 VP1:TPVPANPATT FSSTPVNSFI TQYSTGQVSV QIDWEIQKER SKRWNPEVQF
      AAV-5 VP1:TPVPGN-ITS FSDVPVSSFI TQYSTGQVTV EMEWELKKEN SKRWNPEIQY
Caprine AAV VP1:TPVPGN-ITS FSDVPVSSFI TQYSTGQVTV EMEWELKKEN SKRWNPEIQY
   Parvoviruses:                        *                      * *
  Accessibility:BBBBOOBOOO OOBOOOOOOO OOOBBBBBII IIIIIIIIII IIIBBBBOOO
Surface Feature:    YY YYY YY YYYYYYY YYY                         YYY
            DNA:                                            P
```

FIG. 14G

```
                          AAV-2 capsid structure ends here \                VP1 VP2
      AAV-2 VP1:TSNYNKSVNV DFTVDTNGVY SEPRPIGTRY LTRNL                      735 598
     AAV-3B VP1:TSNYNKSVNV DFTVDTNGVY SEPRPIGTRY LTRNL
      AAV-6 VP1:TSNYAKSANV DFTVDNNGLY TEPRPIGTRY LTRPL
      AAV-1 VP1:TSNYAKSANV DFTVDNNGLY TEPRPIGTRY LTRPL
      AAV-8 VP1:TSNYYKSTSV DFAVNTEGVY SEPRPIGTRY LTRNL
      AAV-4 VP1:TSNYGQQNSL LWAPDAAGKY TEPRAIGTRY LTHHL
      AAV-5 VP1:TNNYNDPQFV DFAPDSTGEY RTTRPIGTRY LTRPL
Caprine AAV VP1:TNNYNDPQFV DFAPDGSGEY RTTRAIGTRY LTRPL
 Neutralization:     ## #
  Accessibility:OBOOOOOOOB OBBBOOOBOO OOOOOBBBOO BBIIB
Surface Feature:Y YYYPYPY  Y    YPP YY YYYYY    YY
            DNA:                                   PB
            DNA:                                    R
          Other:      A
```

FIG. 14H

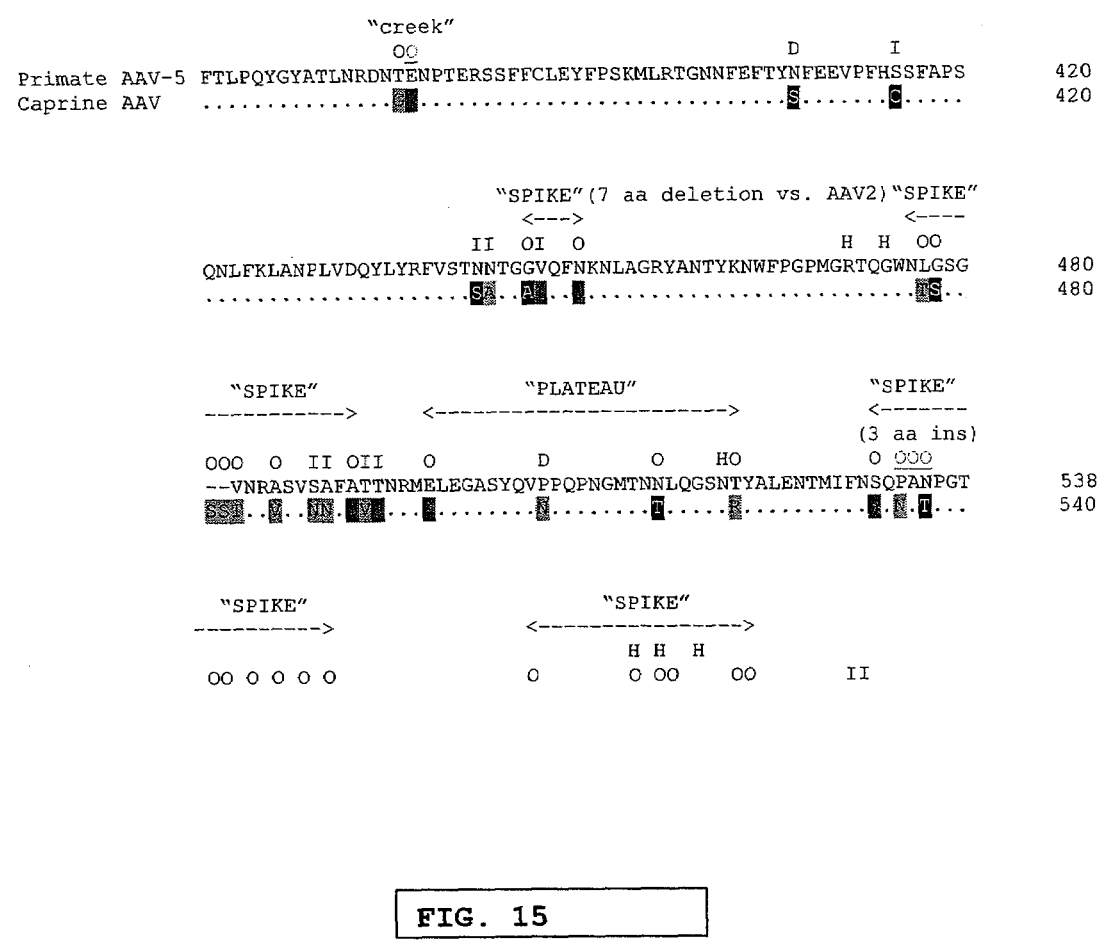

```
                                 "creek"
                                   OO                                D       I
Primate AAV-5  FTLPQYGYATLNRDNTENPTERSSFFCLEYFPSKMLRTGNNFEFTYNFEEVPFHSSFAPS     420
Caprine AAV    ...............[illegible]...........................S.......C.....     420

                                         "SPIKE"(7 aa deletion vs. AAV2)"SPIKE"
                                             <--->                       <----
                                     II  OI  O                      H  H  OO
               QNLFKLANPLVDQYLYRFVSTNNTGGVQFNKNLAGRYANTYKNWFPGPMGRTQGWNLGSG     480
               ....................SA..A..[illegible]...........................[illegible]S..     480

                 "SPIKE"             "PLATEAU"                    "SPIKE"
               ----------->  <---------------------->             <-------
                                                                 (3 aa ins)
               OOO  O  II OII   O        D        O     HO        O OOO
               --VNRASVSAFATTNRMELEGASYQVPPQPNGMTNNLQGSNTYALENTMIFNSQPANPGT     538
               SST..[illegible]..NN.[illegible]V[illegible]...[illegible].........N.........T.....R..........[illegible].N.T...     540

                "SPIKE"                 "SPIKE"
               ---------->          <----------------->
                                          H H  H
               OO O O O O           O     O OO    OO      II
```

FIG. 15

| | Brain | Heart | Kidney | Liver | Lung | Muscle | Spleen | Testis |
|---|---|---|---|---|---|---|---|---|
| AAV-G1 hF.IX (n=2) | 0.0008 | 0.001 | 0.005 | 0.43 | 4.52 | < 0.0005 | 0.060 | 0.0005 |

```
ATGTCTTTTGTTGACCACCCTCCAGATTGGTTGGAATCGATCGGCGACGGCTTTCGTGAATTTCTCGGCCTTGAGGCGGG  80
TCCCCCGAAACCCAAGGCCAATCAACAGAAGCAAGATAACGCTCGAGGTCTTGTGCTTCCTGGGTACAAGTATCTTGGTC  160
CTGGGAACGGCCTTGATAAGGGCGATCCTGTCAATTTTGCTGACGAGGTTGCCCGAGAGCACGACCTCTCCTACCAGAAA  240
CAGCTTGAGGCGGGCGATAACCCTTACCTCAAGTACAACCACGCGGACGCAGAGTTTCAGGAGAAACTCGCTTCTGACAC  320
TTCTTTTGGAGGAAACCTTGGGAAGGCTGTTTTCCAGGCTAAAAAGAGGATTCTCGAACCTCTTGGCCTGGTTGAGACGC  400
CGGATAAAACGGCGCCTGCGGCAAAAAAGAGGCCTCTAGAGCAGAGTCCTCAAGAGCCAGACTCCTCGAGCGGAGTTGGC  480
AAGAAAGGCAAACAGCCTGCCAGAAAGAGACTCAACTTTGACGACGAACCTGGAGCCGGAGACGGGCCTCCCCCAGAAGG  560
ACCATCTTCCGGAGCTATGTCTACTGAGACTGAAATGCGTGCAGCAGCTGGCGGAAATGGTGGCGATGCGGGACAAGGTG  640
CCGAGGGAGTGGGTAATGCCTCCGGTGATTGGCATTGCGATTCCACTTGGTCAGAGAGCCACGTCACCACCACCTCAACC  720
CGCACCTGGGTCCTGCCGACCTACAACAACCACCTGTACCTGCGGCTCGGCTCGAGCAACGCCAGCGACACCTTCAACGG  800
ATTCTCCACCCCCTGGGGATACTTTGACTTTAACCGCTTCCACTGCCACTTCTCGCCAAGAGACTGGCAAAGGCTCATCA  880
ACAACCACTGGGGACTGCGCCCCAAAAGCATGCAAGTCCGCATCTTCAACATCCAAGTTAAGGAGGTCACGACGTCTAAC  960
GGGGAGACGACCGTATCCAACAACCTCACCAGCACGGTCCATATCTTTGCGGACAGCACGTACGAGCTCCCGTACGTGAT  1040
GGATGCAGGTCAGGAGGGCAGCTTGCCTCCTTTCCCCAACGACGTGTTCATGGTGCCTCAGTACGGGTACTGCGGACTGG  1120
TAACCGGAGGCAGCTCTCAAAACCAGACAGACAGAAATGCCTTCTACTGTCTGGAGTACTTTCCCAGCCAGATGCTGAGA  1200
ACCGGAAACAACTTTGAGATGGTGTACAAGTTTGAAAACGTGCCCTTCCACTCCATGTACGCTCACAGCCAGAGCCTGGA  1280
TAGGCTGATGAACCCGCTGCTGGACCAGTACCTGTGGAACTCCAGTCTACCACCTCTGGAGGAACTCTCAACCAGGGCA  1360
ATTCAGCCACCAACTTTGCCAAGCTGACCAACAAAAACTTTTCTGGCTACCGCAAAAACTGGCTCCCGGGGCCCATGATG  1440
AAGCAGCAGAGATTCTCCAAGACTGCCAGTCAAAACTACAAGATTCCCCAGGGAGGAAACAACAGTCTGCTCCATTATGA  1520
GACCAGAACTACCCTCGACAGAAGATGGAGCAATTTTGCCCCGGGAACGGCCATGGCAACCGCAGCCAACGACGCCACCG  1600
ACTTCTCTCAGGCCCAGCTCATCTTTGCGGGGCCCAACATCACCGGCAACACCACCACAGATGCCAATAATCTGATGTTC  1680
ACTTCAGAAGATGAACTTAGGGCCACCAACCCCCGGGACACTGACCTGTTTGGCCACCTGGCAACCAACCAGCAAAACGC  1760
CACCACCGTTCCTACCGTAGACGACGTGGACGGAGTCGGCGTGTACCCGGGAATGGTGTGGCAGGACAGAGACATTTACT  1840
ACCAAGGGCCCATTTGGGCCAAAATTCCACACACGGATGGACACTTTCACCCGTCTCCTCTCATTGGCGGATTTGGACTG  1920
AAAAGCCCGCCTCCACAAATATTCATCAAAAACACTCCTGTACCCGCCAATCCCGCAACGACCTTCTCTCCGGCCAGAAT  2000
CAACAGCTTCATCACCCAGTACAGCACCGGACAGGTGGCTGTCAAAATAGAATGGGAAATCCAGAAGGAGCGGTCCAAGA  2080
GATGGAACCCAGAGGTCCAGTTCACGTCCAACTACGGAGCACAGGACTCGCTTCTCTGGCTCCCGACAACGCCGGAGCC  2150
TACAAAGAGCCCAGGGCCATTGGATCCCGATACCTCACCAACCACCTCTAG  2211
```

FIG 20A

```
MSFVDHPPDWLESIGDGFREFLGLEAGPPKPKANQQKQDNARGLVLPGYK  50
YLGPGNGLDKGDPVNFADEVAREHDLSYQKQLEAGDNPYLKYNHADAEFQ  100
EKLASDTSFGGNLGKAVFQAKKRILEPLGLVETPDKTAPAAKKRPLEQSP  150
QEPDSSSGVGKKGKQPARKRLNFDDEPGAGDGPPPEGPSSGAMSTETEMR  200
AAAGGNGGDAGQGAEGVGNASGDWHCDSTWSESHVTTTSTRTWVLPTYNN  250
HLYLRLGSSNASDTFNGFSTPWGYFDFNRFHCHFSPRDWQRLINNHWGLR  300
PKSMQVRIFNIQVKEVTTSNGETTVSNNLTSTVHIFADSTYELPYVMDAG  350
QEGSLPPFPNDVFMVPQYGYCGLVTGGSSQNQTDRNAFYCLEYFPSQMLR  400
TGNNFEMVYKFENVPFHSMYAHSQSLDRLMNPLLDQYLWELQSTTSGGTL  450
NQGNSATNFAKLTNKNFSGYRKNWLPGPMMKQQRFSKTASQNYKIPQGGN  500
NSLLHYETRTTLDRRWSNFAPGTAMATAANDATDFSQAQLIFAGPNITGN  550
TTTDANNLMFTSEDELRATNPRDTDLFGHLATNQQNATTVPTVDDVDGVG  600
VYPGMVWQDRDIYYQGPIWAKIPHTDGHFHPSPLIGGFGLKSPPPQIFIK  650
NTPVPANPATTFSPARINSFITQYSTGQVAVKIEWEIQKERSKRWNPEVQ  700
FTSNYGAQDSLLWAPDNAGAYKEPRAIGSRYLTNHL  736
```

FIG 20B

```
                                                                 VP1 VP2
   AAV-2 VP1:MAADGYLPDW LEDTLSEGIR QWWKLKPGPP PPKPAERHKD DSRGLVLPGY 50
  AAV-3B VP1:.......... ...N...... E..A...... Q..A...... ..........
   AAV-6 VP1:.......... ...N...... E..D....A. K..ANQQKQ. .G........
   AAV-1 VP1:.......... ...N...... E..D....A. K..ANQQKQ. .G........
   AAV-8 VP1:.......... ...N...... E..A....A. K..ANQQKQ. .G........
   AAV-4 VP1:.-T....... ...N....V. E..A.Q..A. K..ANQQ.Q. NA........
  AAV-C1 VP1:.SFVDHP... ..S-IGD.F. EFLG.EA... K.KANQQKQ. NA........
   AAV-5 VP1:.SFVDHP... ..E-VG..L. EFLG.EA... K...NQQ.Q. QA........
  AAV-G1 VP1:.SFVDHP... ..E-VG..L. EFLG.EA... K...NQQ.Q. QA........
Parvoviruses:*
       Other:                                              PPPPPPP

   AAV-2 VP1:KYLGPFNGLD KGEPVNEADA AALEHDKAYD RQLDSGDNPY LKYNHADAEF 100
  AAV-3B VP1:.....G.... .......... .......... Q..KA..... ..........
   AAV-6 VP1:.......... ......A... .......... Q..KA..... .R........
   AAV-1 VP1:.......... ......A... .......... Q..KA..... .R........
   AAV-8 VP1:.......... ......A... .......... Q..QA..... .R........
   AAV-4 VP1:.....G.... ......A... .......... Q..KA..... ..........
  AAV-C1 VP1:.....G.... ..D...F..E V.R...LS.Q K..EA..... ..........
   AAV-5 VP1:N....G.... R.....R..E V.R...IS.N E..EA..... ..........
  AAV-G1 VP1:N....G.... R.....R..E V.R...IS.N E..EA..... ..........
Parvoviruses:                   *     **  *                  *
       Other:PPPPPPPPPP PPPPPPPPPP PPPPPPPPPP PPPPPPPPPP PPPPPPPPPP
```

FIG. 21A

```
                                                                         VP1  VP2
 AAV-2 VP1:QERLKEDTSF GGNLGRAVFQ AKKRVLEPLG LVEEPVKTAP G-KKRPVEHSP 150   13
AAV-3B VP1:....Q..... .......... ....I..... ....AA.... .-.....DQ..
 AAV-6 VP1:....Q..... .......... ........F. ....GA.... .-......Q..
 AAV-1 VP1:....Q..... .......... .......... ....GA.... .-......Q..
 AAV-8 VP1:....Q..... .......... .......... ....GA.... .-......P..
 AAV-4 VP1:.Q..QG.... .......... .......... ...QAGE... .-.....IE..
AAV-C1 VP1:..K.AS.... .....K.... ....I..... ...T.D.... AA....L.Q..
 AAV-5 VP1:..K.AD.... .....K.... ........F. ....GA.... T-G..IDD.F.
AAV-G1 VP1:..K.AD.... .....K.... ........F. ....GA.... T-G..IDD.F.
     Other:PPPPPPPPPP PPPPPPPPPP PPPPPPPPPP PPPPP

 AAV-2 VP1:VE-PDSSSGTG KAGQQPARKR LNFGQTGDAD SVPD-PQPLGQ PPAAP-SGLGT 200 63
AAV-3B VP1:Q.-.......V. .S.K...... ........SE ....-.....E .....-TS..S
 AAV-6 VP1:Q.-.......I. .T.....K.. ........SE ....-.....E ...T.-AAV.P
 AAV-1 VP1:Q.-.......I. .T.....KKR ........SE ....-.....E ...T.-AAV.P
 AAV-8 VP1:QRS....T.I. .K........ ........SE ....-.....E .....-..V.P
 AAV-4 VP1:QQ-....T.I. .K.K...K.K .V.EDETG.G DG.P-EGSTSG AMSDD-.----
AAV-C1 VP1:Q.-.......V. .K.K...... ...DDEPG.G DG.P.EGPSSG AMSTE-T----
 AAV-5 VP1:----------- .RKKARTEED SKPSTSS..E AGPS-GSQQL. I..Q.A.S..A
AAV-G1 VP1:----------- .RKKARTEED SKPSTSS..E AGPS-GSQQL. I..Q.A.S..A
```

FIG. 21B

```
                                                                       VP1 VP2
                                 /AAV-2 capsid structure begins here.
      AAV-2 VP1:NTMATGSGAP MADNNEGADG VGNSSGNWHC DSTWMGDRVI TTSTRTWALP 250 113
     AAV-3B VP1:....S.G... .......... .......... ..Q.L..... ..........
      AAV-6 VP1:T...S.G... .......... ...A...... ....L..... ..........
      AAV-1 VP1:T...S.G... .......... ...A...... ....L..... ..........
      AAV-8 VP1:....A.G... .......... ..SS...... ....L..... ..........
      AAV-4 VP1:-E.RAAA.GA AVEGGQ.... ...A..D... ....SEGH.T .......V..
     AAV-C1 VP1:-E.RAAA.GN GG.AGQ..E. ...A..D... ....SESH.T .......V..
      AAV-5 VP1:D..SA.G.G. LG...Q.... ...A..D... .........V .K.....V..
     AAV-G1 VP1:D..SA.G.G. LG...Q.... ...A..D... .........V .K.....V..
   Parvoviruses:  *              *  *                           *
  Accessibility:                 IIII IIIIIIIIII IIIIIIIII  IIIIBBBBBB
            DNA:                              R  P B
          Other:                                 M

      AAV-2 VP1:TYNNHLYKQI SSQS--GASNDN HYFGYSTPWG YFDFNRFHCH FSPRDWQRLI 300 163
     AAV-3B VP1:.......... ....--...... .......... .......... ..........
      AAV-6 VP1:.......... ..A.T-...... .......... .......... ..........
      AAV-1 VP1:.......... ..A.T-...... .......... .......... ..........
      AAV-8 VP1:.......... .NGTSG..T... T......... .......... ..........
      AAV-4 VP1:........RL GESL-----QS. T.N.F..... .......... ..........
     AAV-C1 VP1:.......LRL G.SN-----ASD TFN.F..... .......... ..........
      AAV-5 VP1:S....Q.RE. K.G.V-DG..A. A......... ........S. W.........
     AAV-G1 VP1:S....Q.RE. K.G.V-DG..A. A......... ........S. W.........
   Parvoviruses:      *                       ***    * *        *   *
 Neutralization:              #  # # #  #
  Accessibility:OOOOBOBOOO OBOO  OOOOOO OOBBBBBBBB BBBBBBBBBB BBBBBBBIBB
Surface Feature:YYYY Y YYY Y PP  PPPPPP PP
          Other:             AA
```

FIG. 21C

```
                                                                                 VP1  VP2
    AAV-2 VP1:NNNWGFRPKR LNFKLFNIQV KEVTQNDGTT TIANNLTSTV QVFTDSEYQL    350  213
   AAV-3B VP1:.........K .S........ .......... .......... ..........
    AAV-6 VP1:.......... .......... ....T...V. .......... ...S......
    AAV-1 VP1:.......... .......... ....T...V. .......... ...S......
    AAV-8 VP1:.......... .S........ ......E..K .........I ..........
    AAV-4 VP1:.....M...A MRV.I..... ....TSN.E. .V........ .I.A..S.E.
   AAV-C1 VP1:..H..L...S MQVRI..... ....TSN.E. .VS....... HI.A..T.E.
    AAV-5 VP1:..Y.....RS LRV.I..... ....VQ.S.. .......... .....DD...
   AAV-G1 VP1:..Y.....RS LRV.I..... ....VQ.S.. .......... .....DD...
  Parvoviruses:                    *                   *        *
 Accessibility:IIBIBBIIII IIBIBIBBBB OOOOOOOOOO OOBIBIBBBB BBIIIIIIBB
Surface Feature:                     CCCCCCCCCC CC
          DNA:   B     D BB                                 PB D
        Other:                                              M

    AAV-2 VP1:PYVLGSAHQG CLPPFPADVF MVPQYGYLTL N--NGSQ-AVGRS SFYCLEYFPS 400/263
   AAV-3B VP1:.......... .......... .......... .--....-..... ..........
    AAV-6 VP1:.......... .......... .I........ .--....-..... ..........
    AAV-1 VP1:.......... .......... .I........ .--....-..... ..........
    AAV-8 VP1:.......... .......... .I........ .--....-..... ..........
    AAV-4 VP1:...MDAGQE. S.....N... .......CG. VTG.T..QQTD.N A.........
   AAV-C1 VP1:...MDAGQE. S.....N... .......CG. VTG..S.NQTD.N A.........
    AAV-5 VP1:...V.NGTE. ...A..PQ.. TL.....A.. .RD.TEN-PTE.. ..F.......
   AAV-G1 VP1:...V.NGTE. ...A..PQ.. TL.....A.. .RD..DN-PTE.. ..F.......
  Parvoviruses:*                           *
 Accessibility:BIBBBBBBBB BBBBBBBBBB OBOOBBBBBB O OOOOBBBBB BBBBBBBIII
Surface Feature:                     Y YY       P PPPP
        Other:                                     AA
```

FIG. 21D

```
                                                                                   VP1  VP2
         AAV-2 VP1:QMLRTGNNFT FSYTFEDVPF HSSYAHSQSL DRLMNPLIDQ YLYYLSRTN-T  450  313
        AAV-3B VP1:.........Q .......... .......... .......... .....N..QG.
         AAV-6 VP1:.......... .......... .......... .......... .....N..Q-N
         AAV-1 VP1:.......... ......E... .......... .......... .....N..Q-N
         AAV-8 VP1:.........Q .T........ .......... .......... ........Q-.
         AAV-4 VP1:.........E IT.S..K... ..M....... .......... ..WG.QS.T-.
        AAV-C1 VP1:.........E MV.K..N... ..M....... .......L.. ..WE.QS.T-S
         AAV-5 VP1:K........E .T.N..E... ...F.P..N. FK.A...V.. ...RFVS..-N
        AAV-G1 VP1:K........E .T.S..E... .C.F.P..N. FK.A...V.. ...RFVS.S-A
      Parvoviruses:     *
     Accessibility: IIBBBIIII IIIIIIIIII BIBIBBIBOB OBBBBBOOOB BBBBBBOBB O
   Surface Feature:                              P  P     YYY         S   S
              DNA: P        B    BB D       D D

         AAV-2 VP1:-PSGTTTQSRL QFSQAGASDI RDQSRNWLPG PCYRQQRVSK TSA-----DNNNSEY500363
        AAV-3B VP1:-T....N.... L.....PQSM SL.A...... .......... .AN-----.....NF
         AAV-6 VP1:-Q..SAQNKD. L..RGSPAGM SV.PK..... .......... .KT-----.....NF
         AAV-1 VP1:-Q..SAQNKD. L..RGSPAGM SV.PK..... .......... .KT-----.....NF
         AAV-8 VP1:-TG..ANTQT. G...G.PNTM AN.AK..... .........T .TG-----.....NF
         AAV-4 VP1:GTTLNAGTATT N.TKLRPTNF SNFKK..... .SIK..GF.. .ANQNYKIPATG.DS
        AAV-C1 VP1:GGTLNQGNSAT N.AKLTNKNF SGYRK..... .MMK..RF.. .ASQNYKIPQGG.NS
         AAV-5 VP1:-TG.------V ..NKNL.GRY ANTYK..F.. .MG.T.GWNL G.G-----V.RA.VS
        AAV-G1 VP1:-TGA------I ..QKNL.GRY ANTYK..F.. .MG.T.GWNT S.G---SST.RV.VN
    Neutralization:- #                    #                     #  -----  #  #
     Accessibility:-OOOOOOOOOB OBBBBOOOOB OOBBBBBBBB BBOOBBOOBO OOO-----OBOOOOB
   Surface Feature:-SSSSSSSSS S    PPPP  PP           SS   SS S SSS----  S SSSS
             Other:                                    H   H
```

FIG. 21E

```
                                                                                VP1  VP2
      AAV-2 VP1:SWTGATKYHL NGRDSLVNPG PAMASHKDDE EKFFPQSGVL IFGKQGSEKT  550  413
     AAV-3B VP1:P..A.S.... .......... .......... .....MH.N. ....E.TTAS
      AAV-6 VP1:T....S..N. ...E.II... T........K D....M...M ....ESAGAS
      AAV-1 VP1:T....S..N. ...E.II... T......... D....M...M ....ESAGAS
      AAV-8 VP1:A..AG..... ...N..A... I...T..... .R...SN.I. .....NAARD
      AAV-4 VP1:LIKYE.HST. D..W.ALT.. PP..TAGPAD S..SNSQLIF AGP..NGNTA
     AAV-C1 VP1:LLHYE.RTT. DR.W.NFA.. T...TAAN.A TD.SQAQLIF AGPNITGNT.
      AAV-5 VP1:AFATTNRME. E.ASYQ.P.Q PNGMTNNLQG SNTYALENTM ..NS.PANPG
     AAV-G1 VP1:NFSVSNRMN. E.ASYQ...Q PNGMTNTLQG SNRYALENTM ..NA.NATPG
 Neutralization: #      #    # #             #  # ###         #   # #
  Accessibility:BOOBBBOBOB OOBOBBBBBB BBBBBBOOOO OOOBBBBBBB BBBOOOBOOO
Surface Feature: PP    P P  PP P             PPPP PSS          SSS SSS
          Other:                                   HH              A

      AAV-2 VP1:NVDI--E-KVMIT DEEEIRTTNP VATEQYGSVS TNLQRGNRQA ATADVNTQGV 600463
     AAV-3B VP1:.AEL---DN.... .......... .......T.A N...SS.TAP T.RT..D..A
      AAV-6 VP1:.TAL---DN.... .....KA... ....RF.T.A V...SSSTDP A.G..HVM.A
      AAV-1 VP1:.TAL---DN.... .....KA... ....RF.T.A V.F.SSSTDP A.G..HAM.A
      AAV-8 VP1:.A.Y---SD..L. S....K.... ....E..I.A D...QQ.TAP QIGT..S..A
      AAV-4 VP1:T.PG----TLIF. S...LAA..A TD.DMW.NLP GGD.SNSNLP TVDRLTAL.A
     AAV-C1 VP1:TDAN----NL.F. S.D.L.A... RD.DLF.HLA ..Q.NATTVP TVD..DGV..
      AAV-5 VP1:TTATYL.GNML.. S.S.TQPV.R ..YNVG.QMA ..N.SSTTAP ..GTY.L.EI
     AAV-G1 VP1:TTSVYP.DNLLL. S.S.TQPV.R ..YNTG.QMA ..A.NATTAP TVGTY.L.E.
 Neutralization:       #                     #            ##
  Accessibility:OOOO  O OOBOB OBOOBOBBBB BBBOOBBOBB OOOBOOOOOB OOOOBOOOBB
Surface Feature:SSSS  S SS S  Y YY Y        PP   P   SSS SSSSS  PPPP PPP
          Other:                                       H  H  H
```

FIG. 21F

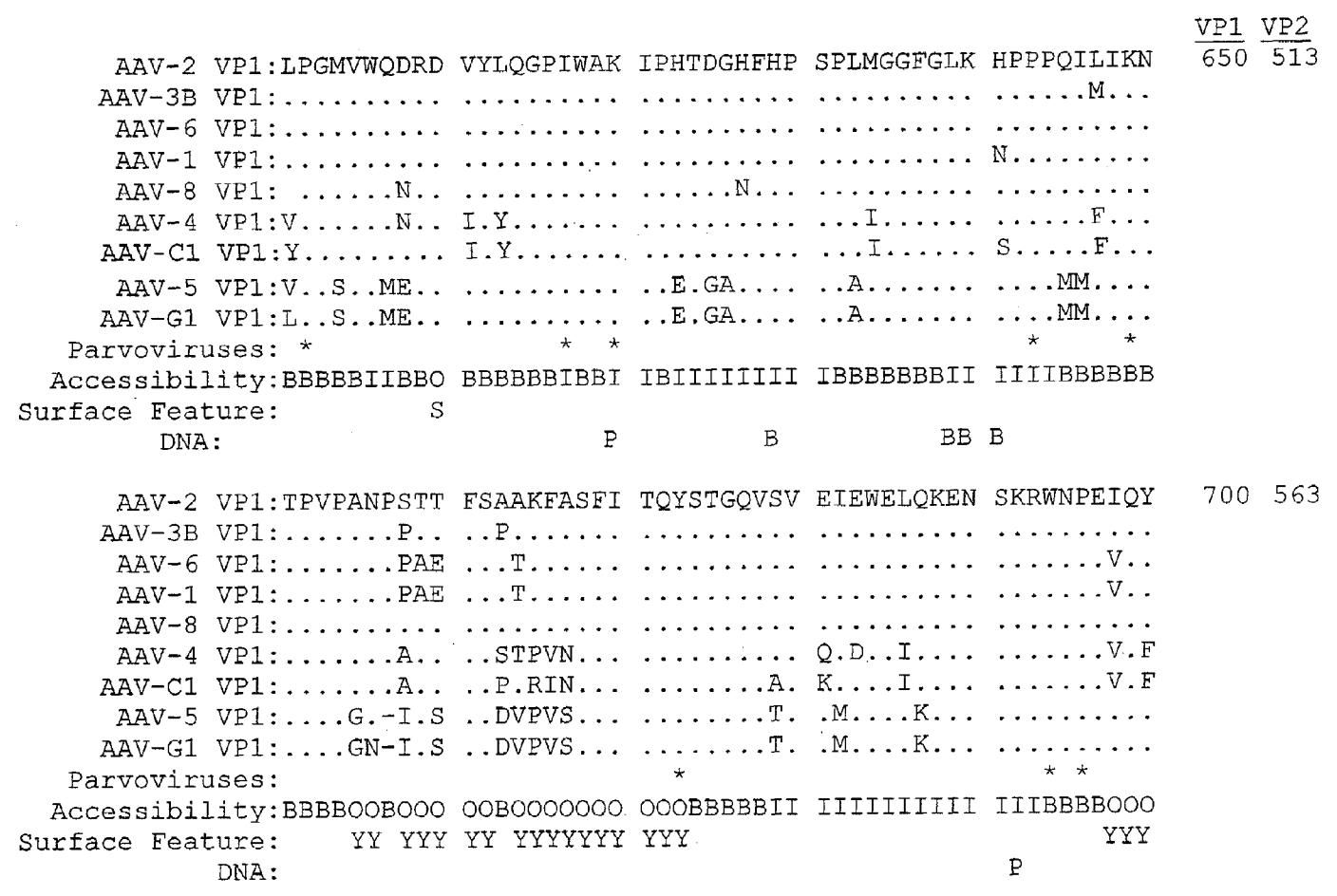

```
                                                                            VP1  VP2
    AAV-2 VP1:LPGMVWQDRD VYLQGPIWAK IPHTDGHFHP SPLMGGFGLK HPPPQILIKN   650  513
   AAV-3B VP1:.......... .......... .......... .......... ......M...
    AAV-6 VP1:.......... .......... .......... .......... ..........
    AAV-1 VP1:.......... .......... .......... .......... N.........
    AAV-8 VP1: ......N.. .......... ......N... .......... ..........
    AAV-4 VP1:V......N.. I.Y....... .......... ...I...... ......F...
   AAV-C1 VP1:Y......... I.Y....... .......... ...I...... S.....F...
    AAV-5 VP1:V..S..ME.. .......... ..E.GA.... ..A....... ....MM....
   AAV-G1 VP1:L..S..ME.. .......... ..E.GA.... ..A....... ....MM....
  Parvoviruses: *                * *                        *     *
 Accessibility:BBBBBIIBBO BBBBBBIBBI IBIIIIIIII IBBBBBBBII IIIIBBBBBB
Surface Feature:        S
        DNA:                        P          B          BB B

    AAV-2 VP1:TPVPANPSTT FSAAKFASFI TQYSTGQVSV EIEWELQKEN SKRWNPEIQY   700  563
   AAV-3B VP1:.......P.. ..P....... .......... .......... ..........
    AAV-6 VP1:.......PAE ...T...... .......... .......... .......V..
    AAV-1 VP1:.......PAE ...T...... .......... .......... .......V..
    AAV-8 VP1:.......... .......... .......... .......... ..........
    AAV-4 VP1:.......A.. ..STPVN... .......... Q.D..I.... .......V.F
   AAV-C1 VP1:.......A.. ..P.RIN... .........A. K....I.... .......V.F
    AAV-5 VP1:....G.-I.S ..DVPVS... .........T. .M....K... ..........
   AAV-G1 VP1:....GN-I.S ..DVPVS... .........T. .M....K... ..........
  Parvoviruses:                       *                           * *
 Accessibility:BBBBOOBOOO OOBOOOOOOO OOOBBBBBII IIIIIIIIII IIIBBBBOOO
Surface Feature:    YY YYY YY YYYYYYY YYY                            YYY
          DNA:                                           P
```

FIG. 21G

```
                                                                 VP1  VP2
                     AAV-2 capsid structure ends here \
     AAV-2 VP1:TSNYNKSVNV DFTVDTNGVY SEPRPIGTRY LTRNL            735  598
    AAV-3B VP1:.......... .......... .......... .....
     AAV-6 VP1: ...A..A.. .....N..L. T......... ...P.
     AAV-1 VP1: ...A..A.. .....N..L. T......... ...P.
     AAV-8 VP1: ...Y..TS. ..A.N.E... .......... .....
     AAV-4 VP1:....GQQNSL LWAP.AA.K. T...A..... ..HH.
    AAV-C1 VP1:....GAQDSL LWAP.NA.A. K...A..S.. ..NH.
     AAV-5 VP1:.N...DPQF. ..AP.ST.E. RTT....... ...P.
    AAV-G1 VP1:.N...DPQF. ..AP.GS.E. RTT.A..... ...P.
Neutralization:    ## #
 Accessibility:OBOOOOOOOB OBBBOOOBOO OOOOOBBBOO BBIIB
Surface Feature:Y YYYPYPY  Y   YPP YY YYYYY   YY
           DNA:                                  PB
           DNA:                                   R
         Other:       A
```

FIG. 21H

SEQUENCE LISTING

```
<160> NUMBER OF SEQ ID NOS: 28

<210> SEQ ID NO 1
<211> LENGTH: 31
<212> TYPE: DNA
<213> ORGANISM: Artificial Sequence
<220> FEATURE:
<223> OTHER INFORMATION: chemically synthesized mutagenic oligo

<400> SEQUENCE: 1

ccgctacagg gcgcgatatc agctcactca a                                 31


<210> SEQ ID NO 2
<211> LENGTH: 58
<212> TYPE: DNA
<213> ORGANISM: Artificial Sequence
<220> FEATURE:
<223> OTHER INFORMATION: chemically synthesized polylinker

<400> SEQUENCE: 2

ggatccggta ccgcccgggc tctagaatcg atgtatacgt cgacgtttaa accatatg    58


<210> SEQ ID NO 3
<211> LENGTH: 34
<212> TYPE: DNA
<213> ORGANISM: Artificial Sequence
<220> FEATURE:
<223> OTHER INFORMATION: chemically synthesized oligonucleotide used in
      the mutagenesis

<400> SEQUENCE: 3

agaggcccgg gcgttttagg gcggagtaac ttgc                              34


<210> SEQ ID NO 4
<211> LENGTH: 22
<212> TYPE: DNA
<213> ORGANISM: Artificial Sequence
<220> FEATURE:
<223> OTHER INFORMATION: chemically synthesized oligonucleotide used in
      the mutagenesis

<400> SEQUENCE: 4

acatacccgc aggcgtagag ac                                           22


<210> SEQ ID NO 5
<211> LENGTH: 10
<212> TYPE: DNA
<213> ORGANISM: Artificial Sequence
<220> FEATURE:
<223> OTHER INFORMATION: chemically synthesized Not I oligonucleotide

<400> SEQUENCE: 5
```

-continued agcggccgct 10

<210> SEQ ID NO 6
<211> LENGTH: 30
<212> TYPE: DNA
<213> ORGANISM: Artificial Sequence
<220> FEATURE:
<223> OTHER INFORMATION: chemically synthesized linker "145NA/NB"

<400> SEQUENCE: 6
ccaactccat cactaggggt tcctgcggcc 30

<210> SEQ ID NO 7
<211> LENGTH: 8
<212> TYPE: DNA
<213> ORGANISM: Artificial Sequence
<220> FEATURE:
<223> OTHER INFORMATION: chemically synthesized Sse I linker

<400> SEQUENCE: 7 cctgcagg 8

<210> SEQ ID NO 8
<211> LENGTH: 19
<212> TYPE: DNA
<213> ORGANISM: Artificial Sequence
<220> FEATURE:
<223> OTHER INFORMATION: chemically synthesized lac Z primer #LZ-1883F

<400> SEQUENCE: 8
tgccactcgc tttaatgat 19

<210> SEQ ID NO 9
<211> LENGTH: 19
<212> TYPE: DNA
<213> ORGANISM: Artificial Sequence
<220> FEATURE:
<223> OTHER INFORMATION: chemically synthesized lac Z primer #LZ-1948R

<400> SEQUENCE: 9
tcgccgcaca tctgaactt 19

<210> SEQ ID NO 10
<211> LENGTH: 23
<212> TYPE: DNA
<213> ORGANISM: Artificial Sequence
<220> FEATURE:
<223> OTHER INFORMATION: chemically synthesized lacZ probe # LZ-1906T

<400> SEQUENCE: 10
agcctccagt acagcgcggc tga 23

<210> SEQ ID NO 11
<211> LENGTH: 12
<212> TYPE: PRT
<213> ORGANISM: Artificial Sequence
<220> FEATURE:
<223> OTHER INFORMATION: chemically synthesized inserted sequence

<400> SEQUENCE: 11

Asp Ala Ser Asn Asp Asn Leu Ser Ser Gln Ser Asp
1 5 10

<210> SEQ ID NO 12
<211> LENGTH: 598
<212> TYPE: PRT

-continued

<213> ORGANISM: adeno-associated virus 2

<400> SEQUENCE: 12

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

-continued

```
Gly Val Leu Ile Phe Gly Lys Gln Gly Ser Glu Lys Thr Asn Val Asp
                405                 410                 415

Ile Glu Lys Val Met Ile Thr Asp Glu Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
    450                 455                 460

Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Pro Gln Ile Leu Ile Lys
            500                 505                 510

Asn Thr Pro Val Pro Ala Asn Pro Ser Thr Thr Phe Ser Ala Ala Lys
        515                 520                 525

Phe Ala Ser Phe Ile Thr Gln Tyr Ser Thr Gly Gln Val Ser Val Glu
    530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595


<210> SEQ ID NO 13
<211> LENGTH: 735
<212> TYPE: PRT
<213> ORGANISM: adeno-associated virus 2

<400> SEQUENCE: 13

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

-continued

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

-continued

Ala Asp Val Asn Thr Gln Gly Val Leu Pro Gly Met Val Trp Gln Asp
595 600 605

Arg Asp Val Tyr Leu Gln Gly Pro Ile Trp Ala Lys Ile Pro His Thr
610 615 620

Asp Gly His Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Ser Thr Thr Phe Ser Ala Ala Lys Phe Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Asn Lys Ser Val Asn Val Asp Phe Thr Val Asp Thr Asn Gly Val Tyr
705 710 715 720

Ser Glu Pro Arg Pro Ile Gly Thr Arg Tyr Leu Thr Arg Asn Leu
725 730 735

<210> SEQ ID NO 14
<211> LENGTH: 2172
<212> TYPE: DNA
<213> ORGANISM: adeno-associated virus 5

<400> SEQUENCE: 14
atgtcttttg ttgatcaccc tccagattgg ttggaagaag ttggtgaagg tcttcgcgag 60
tttttgggcc ttgaagcggg cccaccgaaa ccaaaaccca atcagcagca tcaagatcaa 120
gcccgtggtc ttgtgctgcc tggttataac tatctcggac ccggaaacgg tctcgatcga 180
ggagagcctg tcaacagggc agacgaggtc gcgcgagagc acgacatctc gtacaacgag 240
cagcttgagg cgggagacaa cccctacctc aagtacaacc acgcggacgc cgagtttcag 300
gagaagctcg ccgacgacac atccttcggg ggaaacctcg gaaaggcagt ctttcaggcc 360
aagaaaaggg ttctcgaacc ttttggcctg gttgaagagg gtgctaagac ggcccctacc 420
ggaaagcgga tagacgacca ctttccaaaa agaaagaagg ctcggaccga agaggactcc 480
aagccttcca cctcgtcaga cgccgaagct ggacccagcg gatcccagca gctgcaaatc 540
ccagcccaac cagcctcaag tttgggagct gatacaatgt ctgcgggagg tggcggccca 600
ttgggcgaca ataaccaagg tgccgatgga gtgggcaatg cctcgggaga ttggcattgc 660
gattccacgt ggatggggga cagagtcgtc accaagtcca cccgaacctg ggtgctgccc 720
agctacaaca accaccagta ccgagagatc aaaagcggct ccgtcgacgg aagcaacgcc 780
aacgcctact ttggatacag caccccctgg gggtactttg actttaaccg cttccacagc 840
cactggagcc cccgagactg gcaaagactc atcaacaact actggggctt cagaccccgg 900
tccctcagag tcaaaatctt caacattcaa gtcaaagagg tcacggtgca ggactccacc 960
accaccatcg ccaacaacct cacctccacc gtccaagtgt ttacggacga cgactaccag 1020
ctgccctacg tcgtcggcaa cgggaccgag ggatgcctgc cggccttccc tccgcaggtc 1080
tttacgctgc cgcagtacgg ttacgcgacg ctgaaccgcg acaacacaga aaatcccacc 1140
gagaggagca gcttcttctg cctagagtac tttcccagca agatgctgag aacgggcaac 1200
aactttgagt ttacctacaa ctttgaggag gtgcccttcc actccagctt cgctcccagt 1260
cagaacctgt tcaagctggc caacccgctg gtggaccagt acttgtaccg cttcgtgagc 1320

-continued

```
acaaataaca ctggcggagt ccagttcaac aagaacctgg ccgggagata cgccaacacc   1380

tacaaaaact ggttcccggg gcccatgggc cgaacccagg gctggaacct gggctccggg   1440

gtcaaccgcg ccagtgtcag cgccttcgcc acgaccaata ggatggagct cgagggcgcg   1500

agttaccagg tgcccccgca gccgaacggc atgaccaaca acctccaggg cagcaacacc   1560

tatgccctgg agaacactat gatcttcaac agccagccgg cgaacccggg caccaccgcc   1620

acgtacctcg agggcaacat gctcatcacc agcgagagcg agacgcagcc ggtgaaccgc   1680

gtggcgtaca acgtcggcgg gcagatggcc accaacaacc agagctccac cactgccccc   1740

gcgaccggca cgtacaacct ccaggaaatc gtgcccggca gcgtgtggat ggagagggac   1800

gtgtacctcc aaggacccat ctgggccaag atcccagaga cgggggcgca ctttcacccc   1860

tctccggcca tgggcggatt cggactcaaa cacccaccgc ccatgatgct catcaagaac   1920

acgcctgtgc ccggaaatat caccagcttc tcggacgtgc ccgtcagcag cttcatcacc   1980

cagtacagca ccgggcaggt caccgtggag atggagtggg agctcaagaa ggaaaactcc   2040

aagaggtgga acccagagat ccagtacaca aacaactaca acgacccccca gtttgtggac   2100

tttgccccgg acagcaccgg ggaatacaga accaccagac ctatcggaac ccgatacctt   2160

acccgacccc tt                                                        2172
```

<210> SEQ ID NO 15
<211> LENGTH: 2181
<212> TYPE: DNA
<213> ORGANISM: adeno-associated virus

<400> SEQUENCE: 15

```
atgtcttttg ttgatcaccc tccagattgg ttggaagaag ttggtgaagg tcttcgcgag     60

tttttgggcc ttgaagcggg cccaccgaaa ccaaaaccca atcagcagca tcaagatcaa    120

gcccgtggtc ttgtgctgcc tggttataac tatctcggac ccggaaacgg tctcgatcga    180

ggagagcctg tcaacagggc agacgaggtc gcgcgagagc acgacatctc gtacaacgag    240

cagcttgagg cgggagacaa cccctacctc aagtacaacc acgcggacgc cgagtttcag    300

gagaagctcg ccgacgacac atccttcggg ggaaacctcg gaaaggcagt ctttcaggcc    360

aagaaaaggg ttctcgaacc ttttggcctg gttgaagagg gtgctaagac ggcccctacc    420

ggaaagcgga tagacgacca ctttccaaaa agaaagaagg ctcggaccga agaggactcc    480

aagccttcca cctcgtcaga cgccgaagct ggacccagcg gatcccagca gctgcaaatc    540

ccagcacaac cagcctcaag tttgggagct gatacaatgt ctgcgggagg tggcggccca    600

ttgggcgaca ataaccaagg tgccgatgga gtgggcaatg cctcgggaga ttggcattgc    660

gattccacgt ggatgggggga cagagtcgtc accaagtcca cccgcacctg ggtgctgccc    720

agctacaaca accaccagta ccgagagatc aaaagcggct ccgtcgacgg aagcaacgcc    780

aacgcctact ttggatacag caccccctgg gggtactttg actttaaccg cttccacagc    840

cactggagcc cccgagactg gcaaagactc atcaacaact attggggctt cagaccccgg    900

tctctcagag tcaaaatctt caacatccaa gtcaaagagg tcacggtgca ggactccacc    960

accaccatcg ccaacaacct cacctccacc gtccaagtgt ttacggacga cgactaccaa   1020

ctcccgtacg tcgtcggcaa cgggaccgag ggatgcctgc cggccttccc cccgcaggtc   1080

tttacgctgc cgcagtacgg ctacgcgacg ctgaaccgag acaacggaga caacccgaca   1140

gagcggagca gcttcttttg cctagagtac tttcccagca agatgctgag gacgggcaac   1200

aactttgagt ttacctacag ctttgaagag gtgcccttcc actgcagctt cgccccgagc   1260
```

-continued

```
cagaacctct ttaagctggc caacccgctg gtggaccagt acctgtaccg cttcgtgagc   1320

acctcggcca cgggcgccat ccagttccaa aagaacctgg cgggcagata cgccaacacc   1380

tacaaaaact ggttcccggg gcccatgggc cgaacccagg gctggaacac gagctctggg   1440

gtcagcagca ccaacagagt cagcgtcaac aacttttccg tctcaaaccg gatgaacctg   1500

gagggggcca gctaccaagt gaacccccag cccaacggga tgacaaacac gctccaaggc   1560

agcaaccgct acgcgctgga aaacaccatg atcttcaacg ctcaaaacgc cacgccggga   1620

actacctcgg tgtacccaga ggacaatcta ctgctgacca gcgagagcga gactcagccc   1680

gtcaaccggg tggcttacaa cacgggcggt cagatggcca ccaacgccca gaacgccacc   1740

acggctccca cggtcgggac ctacaacctc caggaagtgc ttcctggcag cgtatggatg   1800

gagagggacg tgtacctcca aggacccatc tgggccaaga tcccagagac gggggcgcac   1860

tttcacccct ctccggccat gggcggattc ggactcaaac acccgccgcc catgatgctc   1920

atcaaaaaca cgccggtgcc cggcaacatc accagcttct cggacgtgcc cgtcagcagc   1980

ttcatcaccc agtacagcac cgggcaggtc accgtggaga tggaatggga gctcaaaaag   2040

gaaaactcca agaggtggaa cccagagatc cagtacacca acaactacaa cgacccccag   2100

tttgtggact ttgctccaga cggctccggc gaatacagaa ccaccagagc catcggaacc   2160

cgatacctca cccgacccct t                                               2181
```

```
<210> SEQ ID NO 16
<211> LENGTH: 724
<212> TYPE: PRT
<213> ORGANISM: adeno-associated virus 5

<400> SEQUENCE: 16

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205
```

-continued

```
Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620
```

-continued

```
Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 17
<211> LENGTH: 726
<212> TYPE: PRT
<213> ORGANISM: adeno-associated virus 5

<400> SEQUENCE: 17

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270
```

-continued

```
Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Gly Asp Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Ser Phe Glu Glu Val Pro Phe His Cys Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Ser Ala Thr Gly Ala Ile Gln
        435                 440                 445

Phe Gln Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Thr Ser Ser Gly
465                 470                 475                 480

Ser Ser Thr Asn Arg Val Ser Val Asn Asn Phe Ser Val Ser Asn Arg
                485                 490                 495

Met Asn Leu Glu Gly Ala Ser Tyr Gln Val Asn Pro Gln Pro Asn Gly
            500                 505                 510

Met Thr Asn Thr Leu Gln Gly Ser Asn Arg Tyr Ala Leu Glu Asn Thr
        515                 520                 525

Met Ile Phe Asn Ala Gln Asn Ala Thr Pro Gly Thr Thr Ser Val Tyr
    530                 535                 540

Pro Glu Asp Asn Leu Leu Leu Thr Ser Glu Ser Glu Thr Gln Pro Val
545                 550                 555                 560

Asn Arg Val Ala Tyr Asn Thr Gly Gly Gln Met Ala Thr Asn Ala Gln
                565                 570                 575

Asn Ala Thr Thr Ala Pro Thr Val Gly Thr Tyr Asn Leu Gln Glu Val
            580                 585                 590

Leu Pro Gly Ser Val Trp Met Glu Arg Asp Val Tyr Leu Gln Gly Pro
        595                 600                 605

Ile Trp Ala Lys Ile Pro Glu Thr Gly Ala His Phe His Pro Ser Pro
    610                 615                 620

Ala Met Gly Gly Phe Gly Leu Lys His Pro Pro Pro Met Met Leu Ile
625                 630                 635                 640

Lys Asn Thr Pro Val Pro Gly Asn Ile Thr Ser Phe Ser Asp Val Pro
                645                 650                 655

Val Ser Ser Phe Ile Thr Gln Tyr Ser Thr Gly Gln Val Thr Val Glu
            660                 665                 670

Met Glu Trp Glu Leu Lys Lys Glu Asn Ser Lys Arg Trp Asn Pro Glu
        675                 680                 685

Ile Gln Tyr Thr Asn Asn Tyr Asn Asp Pro Gln Phe Val Asp Phe Ala
```

-continued

```
    690                 695                 700

Pro Asp Gly Ser Gly Glu Tyr Arg Thr Thr Arg Ala Ile Gly Thr Arg
705                 710                 715                 720

Tyr Leu Thr Arg Pro Leu
                725


<210> SEQ ID NO 18
<211> LENGTH: 736
<212> TYPE: PRT
<213> ORGANISM: adeno-associated virus 3B

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Pro Pro Gln Pro
            20                  25                  30

Lys Ala Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

-continued

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Val Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 19
<211> LENGTH: 736
<212> TYPE: PRT

-continued

<213> ORGANISM: adeno-associated virus 6

<400> SEQUENCE: 19

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

-continued

```
Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 20
<211> LENGTH: 736
<212> TYPE: PRT
<213> ORGANISM: adeno-associated virus 1

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

-continued

```
Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460
```

-continued

```
Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 21
<211> LENGTH: 738
<212> TYPE: PRT
<213> ORGANISM: adeno-associated virus 8

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525
```

-continued

His Lys Asp Asp Glu Glu Arg Phe Phe Pro Ser Asn Gly Ile Leu Ile
530 535 540

Phe Gly Lys Gln Asn Ala Ala Arg Asp Asn Ala Asp Tyr Ser Asp Val
545 550 555 560

Met Leu Thr Ser Glu Glu Glu Ile Lys Thr Thr Asn Pro Val Ala Thr
565 570 575

Glu Glu Tyr Gly Ile Val Ala Asp Asn Leu Gln Gln Gln Asn Thr Ala
580 585 590

Pro Gln Ile Gly Thr Val Asn Ser Gln Gly Ala Leu Pro Gly Met Val
595 600 605

Trp Gln Asn Arg Asp Val Tyr Leu Gln Gly Pro Ile Trp Ala Lys Ile
610 615 620

Pro His Thr Asp Gly Asn Phe His Pro Ser Pro Leu Met Gly Gly Phe
625 630 635 640

Gly Leu Lys His Pro Pro Pro Gln Ile Leu Ile Lys Asn Thr Pro Val
645 650 655

Pro Ala Asn Pro Ser Thr Thr Phe Ser Ala Ala Lys Phe Ala Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Ser Val Asp Phe Ala Val Asn Thr Glu
705 710 715 720

Gly Val Tyr Ser Glu Pro Arg Pro Ile Gly Thr Arg Tyr Leu Thr Arg
725 730 735

Asn Leu

<210> SEQ ID NO 22
<211> LENGTH: 733
<212> TYPE: PRT
<213> ORGANISM: adeno-associated virus 4

<400> SEQUENCE: 22

Met Thr Asp Gly Tyr Leu Pro Asp Trp Leu Glu Asp Asn Leu Ser Glu
1 5 10 15

Gly Val Arg Glu Trp Trp Ala Leu Gln Pro Gly Ala Pro Lys Pro Lys
20 25 30

Ala Asn Gln Gln His Gln Asp Asn Ala Arg Gly Leu Val Leu Pro Gly
35 40 45

Tyr Lys Tyr Leu Gly Pro Gly Asn Gly Leu Asp Lys Gly Glu Pro Val
50 55 60

Asn Ala Ala Asp Ala Ala Ala Leu Glu His Asp Lys Ala Tyr Asp Gln
65 70 75 80

Gln Leu Lys Ala Gly Asp Asn Pro Tyr Leu Lys Tyr Asn His Ala Asp
85 90 95

Ala Glu Phe Gln Gln Arg Leu Gln Gly Asp Thr Ser Phe Gly Gly Asn
100 105 110

Leu Gly Arg Ala Val Phe Gln Ala Lys Lys Arg Val Leu Glu Pro Leu
115 120 125

Gly Leu Val Glu Gln Ala Gly Glu Thr Ala Pro Gly Lys Lys Arg Pro
130 135 140

Leu Ile Glu Ser Pro Gln Gln Pro Asp Ser Ser Thr Gly Ile Gly Lys
145 150 155 160

-continued

```
Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Thr Thr Leu Asn
        435                 440                 445

Ala Gly Thr Ala Thr Thr Asn Phe Thr Lys Leu Arg Pro Thr Asn Phe
    450                 455                 460

Ser Asn Phe Lys Lys Asn Trp Leu Pro Gly Pro Ser Ile Lys Gln Gln
465                 470                 475                 480

Gly Phe Ser Lys Thr Ala Asn Gln Asn Tyr Lys Ile Pro Ala Thr Gly
                485                 490                 495

Ser Asp Ser Leu Ile Lys Tyr Glu Thr His Ser Thr Leu Asp Gly Arg
            500                 505                 510

Trp Ser Ala Leu Thr Pro Gly Pro Pro Met Ala Thr Ala Gly Pro Ala
        515                 520                 525

Asp Ser Lys Phe Ser Asn Ser Gln Leu Ile Phe Ala Gly Pro Lys Gln
    530                 535                 540

Asn Gly Asn Thr Ala Thr Val Pro Gly Thr Leu Ile Phe Thr Ser Glu
545                 550                 555                 560

Glu Glu Leu Ala Ala Thr Asn Ala Thr Asp Thr Asp Met Trp Gly Asn
                565                 570                 575

Leu Pro Gly Gly Asp Gln Ser Asn Ser Asn Leu Pro Thr Val Asp Arg
```

-continued

```
            580                 585                 590

Leu Thr Ala Leu Gly Ala Val Pro Gly Met Val Trp Gln Asn Arg Asp
        595                 600                 605

Ile Tyr Tyr Gln Gly Pro Ile Trp Ala Lys Ile Pro His Thr Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Ser Ser Thr Pro Val Asn Ser Phe Ile Thr Gln Tyr Ser
            660                 665                 670

Thr Gly Gln Val Ser Val Gln Ile Asp Trp Glu Ile Gln Lys Glu Arg
        675                 680                 685

Ser Lys Arg Trp Asn Pro Glu Val Gln Phe Thr Ser Asn Tyr Gly Gln
    690                 695                 700

Gln Asn Ser Leu Leu Trp Ala Pro Asp Ala Ala Gly Lys Tyr Thr Glu
705                 710                 715                 720

Pro Arg Ala Ile Gly Thr Arg Tyr Leu Thr His His Leu
                725                 730


<210> SEQ ID NO 23
<211> LENGTH: 44
<212> TYPE: DNA
<213> ORGANISM: Artificial Sequence
<220> FEATURE:
<223> OTHER INFORMATION: chemically synthesized forward primer 1

<400> SEQUENCE: 23

gtgcccttct acggctgcgt caactggacc aatgagaact ttcc                      44


<210> SEQ ID NO 24
<211> LENGTH: 32
<212> TYPE: DNA
<213> ORGANISM: Artificial Sequence
<220> FEATURE:
<223> OTHER INFORMATION: chemically synthesized reverse primer 2

<400> SEQUENCE: 24

ggaatcgcaa tgccaatttc ctgaggcatt ac                                   32


<210> SEQ ID NO 25
<211> LENGTH: 2211
<212> TYPE: DNA
<213> ORGANISM: adeno-associated virus C1

<400> SEQUENCE: 25

atgtcttttg ttgaccaccc tccagattgg ttggaatcga tcggcgacgg ctttcgtgaa     60

tttctcggcc ttgaggcggg tcccccgaaa cccaaggcca atcaacagaa gcaagataac    120

gctcgaggtc ttgtgcttcc tgggtacaag tatcttggtc ctgggaacgg ccttgataag    180

ggcgatcctg tcaattttgc tgacgaggtt gcccgagagc acgacctctc ctaccagaaa    240

cagcttgagg cgggcgataa cccttacctc aagtacaacc acgcggacgc agagtttcag    300

gagaaactcg cttctgacac ttcttttgga ggaaaccttg ggaaggctgt tttccaggct    360

aaaaagagga ttctcgaacc tcttggcctg gttgagacgc cggataaaac ggcgcctgcg    420

gcaaaaaaga ggcctctaga gcagagtcct caagagccag actcctcgag cggagttggc    480

aagaaaggca aacagcctgc cagaaagaga ctcaactttg acgacgaacc tggagccgga    540
```

-continued

```
gacgggcctc ccccagaagg accatcttcc ggagctatgt ctactgagac tgaaatgcgt    600

gcagcagctg gcggaaatgg tggcgatgcg ggacaaggtg ccgagggagt gggtaatgcc    660

tccggtgatt ggcattgcga ttccacttgg tcagagagcc acgtcaccac cacctcaacc    720

cgcacctggg tcctgccgac ctacaacaac cacctgtacc tgcggctcgg ctcgagcaac    780

gccagcgaca ccttcaacgg attctccacc ccctggggat actttgactt taaccgcttc    840

cactgccact tctcgccaag agactggcaa aggctcatca acaaccactg gggactgcgc    900

cccaaaagca tgcaagtccg catcttcaac atccaagtta aggaggtcac gacgtctaac    960

ggggagacga ccgtatccaa caacctcacc agcacggtcc atatctttgc ggacagcacg   1020

tacgagctcc cgtacgtgat ggatgcaggt caggagggca gcttgcctcc tttccccaac   1080

gacgtgttca tggtgcctca gtacgggtac tgcggactgg taaccggagg cagctctcaa   1140

aaccagacag acagaaatgc cttctactgt ctggagtact ttcccagcca gatgctgaga   1200

accggaaaca actttgagat ggtgtacaag tttgaaaacg tgcccttcca ctccatgtac   1260

gctcacagcc agagcctgga taggctgatg aacccgctgc tggaccagta cctgtgggaa   1320

ctccagtcta ccacctctgg aggaactctc aaccagggca attcagccac caactttgcc   1380

aagctgacca acaaaaactt ttctggctac cgcaaaaact ggctcccggg gcccatgatg   1440

aagcagcaga gattctccaa gactgccagt caaaactaca agattcccca gggaggaaac   1500

aacagtctgc tccattatga gaccagaact accctcgaca gaagatggag caattttgcc   1560

ccgggaacgg ccatggcaac cgcagccaac gacgccaccg acttctctca ggcccagctc   1620

atctttgcgg ggcccaacat caccggcaac accaccacag atgccaataa tctgatgttc   1680

acttcagaag atgaacttag ggccaccaac ccccgggaca ctgacctgtt tggccacctg   1740

gcaaccaacc agcaaaacgc caccaccgtt cctaccgtag acgacgtgga cggagtcggc   1800

gtgtacccgg gaatggtgtg gcaggacaga gacatttact accaagggcc catttgggcc   1860

aaaattccac acacggatgg acactttcac ccgtctcctc tcattggcgg atttggactg   1920

aaaagcccgc ctccacaaat attcatcaaa aacactcctg tacccgccaa tcccgcaacg   1980

accttctctc cggccagaat caacagcttc atcacccagt acagcaccgg acaggtggct   2040

gtcaaaatag aatgggaaat ccagaaggag cggtccaaga gatggaaccc agaggtccag   2100

ttcacgtcca actacggagc acaggactcg cttctctggg ctcccgacaa cgccggagcc   2160

tacaaagagc ccagggccat tggatcccga tacctcacca accacctcta g            2211
```

<210> SEQ ID NO 26
<211> LENGTH: 736
<212> TYPE: PRT
<213> ORGANISM: adeno-associated virus C1

<400> SEQUENCE: 26

```
Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80
```

-continued

```
Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Ala Lys Lys Arg
    130                 135                 140

Pro Leu Glu Gln Ser Pro Gln Glu Pro Asp Ser Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Pro Glu Gly Pro Ser Ser Gly Ala
            180                 185                 190

Met Ser Thr Glu Thr Glu Met Arg Ala Ala Ala Gly Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
    290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val His Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Gly Ser Ser Gln Asn Gln Thr Asp
    370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
            420                 425                 430

Leu Leu Asp Gln Tyr Leu Trp Glu Leu Gln Ser Thr Thr Ser Gly Gly
        435                 440                 445

Thr Leu Asn Gln Gly Asn Ser Ala Thr Asn Phe Ala Lys Leu Thr Asn
    450                 455                 460

Lys Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
                485                 490                 495

Gln Gly Gly Asn Asn Ser Leu Leu His Tyr Glu Thr Arg Thr Thr Leu
```

-continued

```
                500                 505                 510

Asp Arg Arg Trp Ser Asn Phe Ala Pro Gly Thr Ala Met Ala Thr Ala
        515                 520                 525

Ala Asn Asp Ala Thr Asp Phe Ser Gln Ala Gln Leu Ile Phe Ala Gly
    530                 535                 540

Pro Asn Ile Thr Gly Asn Thr Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
        595                 600                 605

Asp Arg Asp Ile Tyr Tyr Gln Gly Pro Ile Trp Ala Lys Ile Pro His
    610                 615                 620

Thr Asp Gly His Phe His Pro Ser Pro Leu Ile Gly Gly Phe Gly Leu
625                 630                 635                 640

Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
        675                 680                 685

Lys Glu Arg Ser Lys Arg Trp Asn Pro Glu Val Gln Phe Thr Ser Asn
    690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735


<210> SEQ ID NO 27
<211> LENGTH: 29
<212> TYPE: DNA
<213> ORGANISM: Artificial Sequence
<220> FEATURE:
<223> OTHER INFORMATION: chemically synthesized forward primer

<400> SEQUENCE: 27

aaatcaggta tgtcttttgt tgatcaccc                                         29


<210> SEQ ID NO 28
<211> LENGTH: 43
<212> TYPE: DNA
<213> ORGANISM: Artificial Sequence
<220> FEATURE:
<223> OTHER INFORMATION: chemically synthesized reverse primer

<400> SEQUENCE: 28

acacgaatta accggtttat tgagggtatg cgacatgaat ggg                         43
```

AAV VIRIONS WITH DECREASED IMMUNOREACTIVITY AND USES THEREFOR

CROSS-REFERENCE TO RELATED APPLICATION

This application is related to U.S. application Ser. Nos. 60/480,395, filed Jun. 19, 2003; 60/567,310, filed Apr. 30, 2004; and 60/576,501, filed Jun. 3, 2004, from which applications priority is claimed under 35 USC §119(e)(1) and which applications are incorporated herein by reference in their entireties.

TECHNICAL FIELD

The present invention relates generally to compositions and methods for delivering recombinant adeno-associated virus (rAAV) virions to cells. In particular, the present invention pertains to rAAV virions with decreased immunoreactivity, such as mutant rAAV virions, and methods of making and using the same.

BACKGROUND

Scientists are continually discovering genes that are associated with human diseases such as diabetes, hemophilia, and cancer. Research efforts have also uncovered genes, such as erythropoietin (which increases red blood cell production), that are not associated with genetic disorders but instead code for proteins that can be used to treat numerous diseases. Despite significant progress in the effort to identify and isolate genes, however, a major obstacle facing the biopharmaceutical industry is how to safely and persistently deliver therapeutically effective quantities of gene products to patients.

Generally, the protein products of these genes are synthesized in cultured bacterial, yeast, insect, mammalian, or other cells and delivered to patients by direct injection. Injection of recombinant proteins has been successful but suffers from several drawbacks. For example, patients often require weekly, and sometimes daily, injections in order to maintain the necessary levels of the protein in the bloodstream. Even then, the concentration of protein is not maintained at physiological levels—the level of the protein is usually abnormally high immediately following the injection, and far below optimal levels prior to the injection. Additionally, injected delivery of recombinant protein often cannot deliver the protein to the target cells, tissues, or organs in the body. And, if the protein successfully reaches its target, it may be diluted to a non-therapeutic level. Furthermore, the method is inconvenient and often restricts the patient's lifestyle.

These shortcomings have fueled the desire to develop gene therapy methods for delivering sustained levels of specific proteins into patients. These methods are designed to allow clinicians to introduce deoxyribonucleic acid (DNA) coding for a nucleic acid, such as a therapeutic gene, directly into a patient (in vivo gene therapy) or into cells isolated from a patient or a donor (ex vivo gene therapy). The introduced nucleic acid then directs the patient's own cells or grafted cells to produce the desired protein product. Gene delivery, therefore, obviates the need for frequent injections. Gene therapy may also allow clinicians to select specific organs or cellular targets (e.g., muscle, blood cells, brain cells, etc.) for therapy.

DNA may be introduced into a patient's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery vectors include those based on retrovirus, adenovirus, herpes virus, pox virus, and adeno-associated virus (AAV). Like the retroviruses, and unlike adenovirus, AAV has the ability to integrate its genome into a host cell chromosome.

Adeno-Associated Virus-Mediated Gene Therapy

AAV is a parvovirus belonging to the genus Dependovirus, and has several attractive features not found in other viruses. For example, AAV can infect a wide range of host cells, including non-dividing cells. AAV can also infect cells from different species. Importantly, AAV has not been associated with any human or animal disease, and does not appear to alter the physiological properties of the host cell upon integration. Furthermore, AAV is stable at a wide range of physical and chemical conditions, which lends itself to production, storage, and transportation requirements.

The AAV genome, a linear, single-stranded DNA molecule containing approximately 4700 nucleotides (the AAV-2 genome consists of 4681 nucleotides), generally comprises an internal non-repeating segment flanked on each end by inverted terminal repeats (ITRs). The ITRs are approximately 145 nucleotides in length (AAV-1 has ITRs of 143 nucleotides) and have multiple functions, including serving as origins of replication, and as packaging signals for the viral genome.

The internal non-repeated portion of the genome includes two large open reading frames (ORFs), known as the AAV replication (rep) and capsid (cap) regions. These ORFs encode replication and capsid gene products, respectively: replication and capsid gene products (i.e., proteins) allow for the replication, assembly, and packaging of a complete AAV virion. More specifically, a family of at least four viral proteins are expressed from the AAV rep region: Rep 78, Rep 68, Rep 52, and Rep 40, all of which are named for their apparent molecular weights. The AAV cap region encodes at least three proteins: VP1, VP2, and VP3.

In nature, AAV is a helper virus-dependent virus, i.e., it requires co-infection with a helper virus (e.g., adenovirus, herpesvirus, or vaccinia virus) in order to form functionally complete AAV virions. In the absence of co-infection with a helper virus, AAV establishes a latent state in which the viral genome inserts into a host cell chromosome or exists in an episomal form, but infectious virions are not produced. Subsequent infection by a helper virus "rescues" the integrated genome, allowing it to be replicated and packaged into viral capsids, thereby reconstituting the infectious virion. While AAV can infect cells from different species, the helper virus must be of the same species as the host cell. Thus, for example, human AAV will replicate in canine cells that have been co-infected with a canine adenovirus.

To construct infectious recombinant AAV (rAAV) containing a nucleic acid, a suitable host cell line is transfected with an AAV vector containing a nucleic acid. AAV helper functions and accessory functions are then expressed in the host cell. Once these factors come together, the HNA is replicated and packaged as though it were a wild-type (wt) AAV genome, forming a recombinant virion. When a patient's cells are infected with the resulting rAAV, the HNA enters and is expressed in the patient's cells. Because the patient's cells lack the rep and cap genes, as well as the adenovirus accessory function genes, the rAAV are replication defective; that is, they cannot further replicate and package their genomes. Similarly, without a source of rep and cap genes, wtAAV cannot be formed in the patient's cells.

There are several AAV serotypes that infect humans as well as other primates and mammals. Eight major serotypes have been identified, AAV-1 through AAV-8, including two serotypes recently isolated from rhesus monkeys. Gao et al. (2002) *Proc. Natl. Acad. Sci. USA* 99: 11854-11859. Of those serotypes, AAV-2 is the best characterized, having been used to successfully deliver transgenes to several cell lines, tissue types, and organs in a variety of in vitro and in vivo assays. The various serotypes of AAV can be distinguished from one another using monoclonal antibodies or by employing nucleotide sequence analysis; e.g., AAV-1, AAV-2, AAV-3, and AAV-6 are 82% identical at the nucleotide level, while AAV-4 is 75 to 78% identical to the other serotypes (Russell et al. (1998) *J. Virol.* 72: 309-319). Significant nucleotide sequence variation is noted for regions of the AAV genome that code for capsid proteins. Such variable regions may be responsible for differences in serological reactivity to the capsid proteins of the various AAV serotypes.

After an initial treatment with a given AAV serotype, anti-AAV capsid neutralizing antibodies are often made which prevent subsequent treatments by the same serotype. For example, Moskalenko et al. *J. Virol.* (2000) 74: 1761-1766 showed that mice with pre-existing anti-AAV-2 antibodies, when administered Factor IX in a recombinant AAV-2 virion, failed to express the Factor IX transgene, suggesting that the anti-AAV-2 antibodies blocked transduction of the rAAV-2 virion. Halbert et al. *J. Virol.* (1998) 72: 9795-9805 reported similar results. Others have demonstrated successful readministration of rAAV-2 virions into experimental animals, but only after immune suppression is achieved (see, e.g., Halbert et al., supra).

Thus, using rAAV for human gene therapy is potentially problematic because anti-AAV antibodies are prevalent in human populations. Infection of humans by a variety of AAV serotypes occurs in childhood, and possibly even in utero. In fact, one study estimated that at least 80% of the general population has been infected with AAV-2 (Bems and Linden (1995) *Bioessays* 17: 237-245). Neutralizing anti-AAV-2 antibodies have been found in at least 20-40% of humans. Our studies have shown that out of a group of 50 hemophiliacs, approximately 40% had AAV-2 neutralizing capacities exceeding 1e13 viral particles/ml, or about 6e16 viral particles/total blood volume. Furthermore, the majority of the group with high anti-AAV-2 titers also had significant titers against other AAV serotypes, such as AAV-1, AAV-3, AAV-4, AAV-5 and AAV-6. Therefore, identification of AAV mutants with reduced immunoreactivity, such as mutants that are not neutralized by pre-existing anti-AAV antibodies, would be a significant advancement in the art. Such AAV mutants are described herein.

SUMMARY OF THE INVENTION

The present invention is based on the discovery of novel AAV sequences, such as mutated AAV sequences, that provide for recombinant AAV virions with decreased immunoreactivity as compared with the corresponding native serotype but which retain the ability to efficiently transduce cells and tissues. The rAAV virions with decreased immunoreactivity are especially useful for delivering heterologous nucleic acid molecules (HNAs) to subjects that have been previously exposed to AAV, either by natural infection or due to previous gene therapy or nucleic acid immunization treatments, and have therefore developed anti-AAV antibodies. The rAAV virions described herein are therefore useful for treating or preventing a wide variety of disorders, as described further below, in vertebrate subjects that have been previously exposed to any of the various AAV serotypes. In accordance with the present invention, then, methods and AAV vectors for use therein are provided for the efficient delivery of HNAs to the cells or tissue of a vertebrate subject, such as a mammal, using recombinant AAV virions.

In certain preferred embodiments, the present invention provides for the use of AAV virions containing altered capsid proteins to deliver an HNA encoding antisense RNA, ribozymes, or one or more genes that express proteins, wherein expression of said antisense RNA, ribozymes, or one or more genes provides for a biological effect in a mammalian subject. In one embodiment, the rAAV virions containing an HNA are injected directly into a muscle (e.g., cardiac, smooth and/or skeletal muscle). In another embodiment, the rAAV virions containing an HNA are administered into the vasculature via injection into veins, arteries, or other vascular conduits, or by using techniques such as isolated limb perfusion.

In additional embodiments, the virions contain a gene encoding a blood coagulation protein which, when expressed at a sufficient concentration, provides for a therapeutic effect, such as improved blood-clotting efficiency of a mammal suffering from a blood-clotting disorder. The blood-clotting disorder can be any disorder adversely affecting the organism's ability to coagulate the blood. Preferably, the blood clotting disorder is hemophilia. In one embodiment, then, the gene encoding a blood coagulation protein is a Factor VIII gene, such as the human Factor VIII gene or a derivation thereof. In another embodiment, the gene encoding a blood coagulation protein is a Factor IX gene, such as the human Factor IX (hF.IX) gene.

Accordingly, in one embodiment, the present invention is directed to a mutated AAV capsid protein that when present in an AAV virion imparts decreased immunoreactivity to the virion as compared to the corresponding wild-type virion. The mutation may comprise at least one amino acid substitution, deletion or insertion to the native protein, such as a substitution is in the spike or plateau region of the AAV virion surface.

In certain embodiments, the amino acid substitution comprises a substitution of one or more of the amino acids occurring at a position corresponding to a position of the AAV-2 VP2 capsid selected from the group consisting of amino acid 126, 127, 128, 130, 132, 134, 247, 248, 315, 334, 354, 357, 360, 361, 365, 372, 375, 377, 390, 393, 394, 395, 396, 407, 411, 413, 418, 437, 449, 450, 568, 569, and 571. In additional embodiments, the naturally occurring amino acid at one or more of these positions is substituted with an alanine. In further embodiments, the protein further comprises a substitution of histidine for the amino acid occurring at the position corresponding to the amino acid found at position 360 of AAV-2 VP2 and/or a substitution of lysine for the amino acid occurring at the position corresponding to the amino acid found at position 571 of AAV-2 VP2.

In additional embodiments, the invention is directed to a polynucleotide encoding any of the mutated proteins described above.

In further embodiments, the invention is directed to a recombinant AAV virion comprising any of the mutated proteins described above. The recombinant AAV virion can comprise a heterologous nucleic acid molecule encoding an antisense RNA or a ribozymes, or a heterologous nucleic acid molecule encoding a therapeutic protein operably linked to control elements capable of directing the in vivo transcription and translation of said protein.

In yet further embodiments, the invention is directed to a method of delivering a recombinant AAV virion to a cell or tissue of a vertebrate subject. The method comprises:

(a) providing a recombinant AAV virion as above;

(b) delivering the recombinant AAV virion to the cell or tissue, whereby the protein is expressed at a level that provides a therapeutic effect.

In certain embodiments, the cell or tissue is a muscle cell or tissue. The muscle cell or tissue can be derived from skeletal muscle.

In further embodiments, the recombinant AAV virion is delivered into the cell or tissue in vivo.

In certain embodiments, the recombinant AAV virion is delivered by intramuscular injection, or into the bloodstream, such as intravenously or intraarterially. In additional embodiments, the recombinant AAV virion is delivered to the liver or to the brain.

In further embodiments, the recombinant AAV virion is delivered into said cell or tissue in vitro.

In yet an additional embodiment, the invention is directed to a method of delivering a recombinant AAV virion to a cell or tissue of a vertebrate subject. The method comprises:

(a) providing a recombinant AAV virion, wherein the AAV virion comprises
   (i) a non-primate, mammalian adeno-associated virus (AAV) capsid protein that when present in an AAV virion imparts decreased immunoreactivity to the virion as compared to immunoreactivity of primate AAV-2; and
   (ii) a heterologous nucleic acid molecule encoding a therapeutic protein operably linked to control elements capable of directing the in vivo transcription and translation of the protein;

(b) delivering the recombinant AAV virion to the cell or tissue, whereby the protein is expressed at a level that provides a therapeutic effect.

In certain embodiments, the cell or tissue is a muscle cell or tissue, such as a muscle cell or tissue is derived from skeletal muscle.

The recombinant AAV virion is delivered into said cell or tissue in vivo or in vitro and can be delivered to the subject by intramuscular injection, or into the bloodstream, such as intravenously or intraarterially. In additional embodiments, the recombinant AAV virion is delivered to the liver or to the brain.

These and other embodiments of the subject invention will readily occur to those of skill in the art in view of the disclosure herein.

BRIEF DESCRIPTION OF THE FIGURES

FIG. 9 shows the amino acid sequence of an AAV-2 VP2 (SEQ ID NO:12).

FIG. 10 shows the amino acid sequence of an AAV-2 VP1 (SEQ ID NO:13).

FIGS. 12A-12B show a comparison of the nucleotide sequence encoding the AAV VP1 protein from a primate AAV-5 (SEQ ID NO:14) and a caprine AAV (SEQ ID NO:15). Numbering is relative to the AAV-5 full-length sequence.

FIG. 13 shows a comparison of the amino acid sequence of VP1 from a primate AAV-5 (SEQ ID NO:16) and a caprine AAV (SEQ ID NO:17). Amino acid differences are shaded. Conservative changes are shown in light grey; non-conservative changes are shown in dark grey.

FIGS. 14A-14H show a comparison of the amino acid sequence of VP1s from AAVs that are sensitive or resistant to antibody neutralization as follows: primate AAV-2 (SEQ ID NO:13), primate AAV-3B (SEQ ID NO:18), primate AAV-6 (SEQ ID NO:19), primate AAV-1 (SEQ ID NO:20), primate AAV-8 (SEQ ID NO:21), primate AAV-4 (SEQ ID NO:22), primate AAV-5 (SEQ ID NO:16) and caprine (goat) AAV (SEQ ID NO:17). Parvovirus line: *, conserved in almost all parvoviruses. Neutralization line: #, location of single mutations in AAV-2 capsid identified as resistant to neutralization by human sera. Accessibility line: B, amino acid is buried between the inside and outside surface; I, amino acid is found on the inside surface; O, amino acid is found on the outside surface. Surface feature line: C, cylinder; P, plateau; S, spike; Y, canyon. DNA line: B, possible base contact; D, likely required for DNA binding but may not directly contact DNA; P, possible phosphate contact; R, possible ribose contact. Other line: A, location of single mutations that decrease binding and neutralization by mouse monoclonal antibody A20; H, heparin contact in AAV-2; M, possible Mg2+ contact; P, phospholipase A2 domain.

FIG. 15 (SEQ ID NOS: 16 and 17) shows the positions of the amino acid differences between AAV-5 and caprine AAV, relative to the surface of the AAV capsid.

FIGS. 20A (SEQ ID NO:25) and 20B (SEQ ID NO:26) show the nucleotide sequence and amino acid sequence respectively, of a bovine AAV VP1, from AAV-C1.

FIGS. 21A-21H show a comparison of the amino acid sequence of VP1s from AAVs that are sensitive or resistant to antibody neutralization as follows: primate AAV-2 (SEQ ID NO:13), primate AAV-3B (SEQ ID NO:18), primate AAV-6 (SEQ ID NO:19), primate AAV-1 (SEQ ID NO:20), primate AAV-8 (SEQ ID NO:21), primate AAV-4 (SEQ ID NO:22), bovine (cow) AAV ("AAV-C1" (SEQ ID NO:26), primate AAV-5 (SEQ ID NO:16) and caprine (goat) AAV ("AAV-C1" SEQ ID NO:17). Parvovirus line: *, conserved in almost all parvoviruses. Neutralization line: #, location of single mutations in AAV-2 capsid identified as resistant to neutralization by human sera. Accessibility line: B, amino acid is buried between the inside and outside surface; I, amino acid is found on the inside surface; O, amino acid is found on the outside surface. Surface feature line: C, cylinder; P, plateau; S, spike; Y, canyon. DNA line: B, possible base contact; D, likely required for DNA binding but may not directly contact DNA; P, possible phosphate contact; R, possible ribose contact. Other line: A, location of single mutations that decrease binding and neutralization by mouse monoclonal antibody A20; H, heparin contact in AAV-2; M, possible Mg2+ contact; P, phospholipase A2 domain.

DETAILED DESCRIPTION OF THE INVENTION

Figure 1:
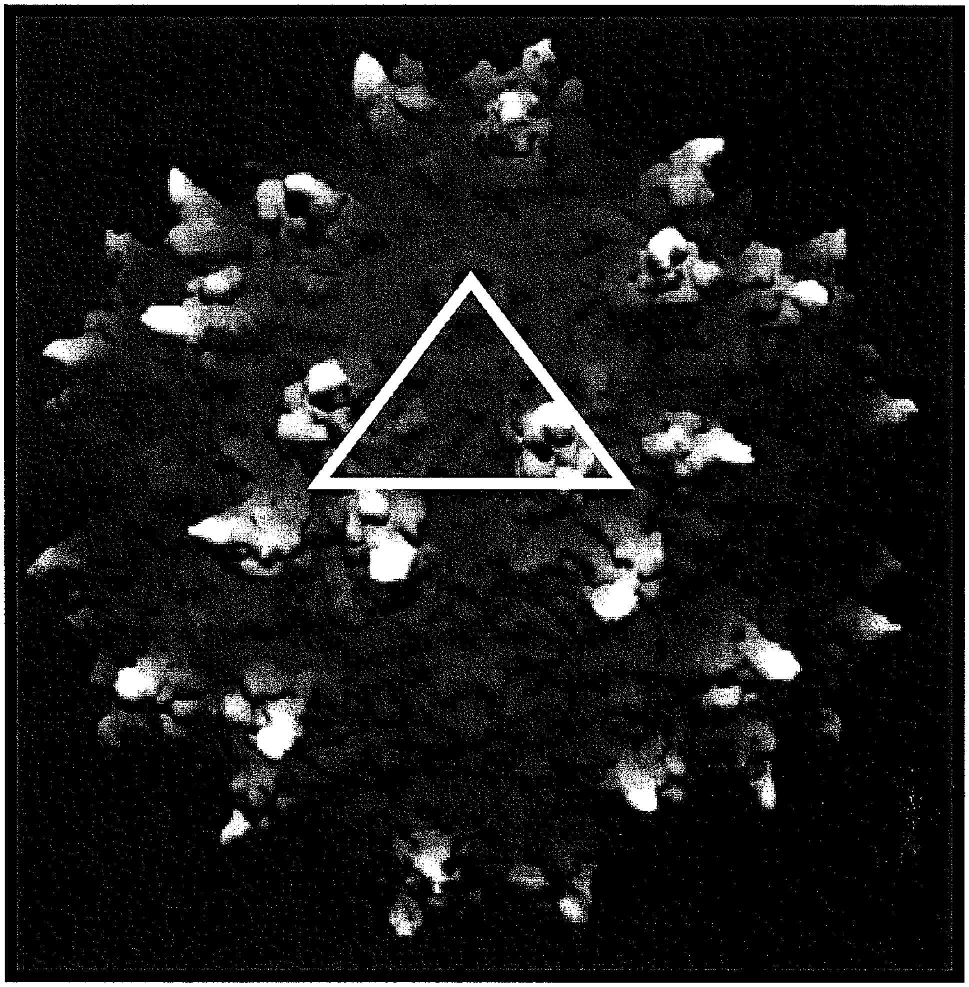
FIG. 1 illustrates the location of an asymmetrical structural unit (white triangle) of AAV-2 on the surface of the entire virus (taken from FIG. 3*a* of Xie et al. *Proc. Natl. Acad. Sci. USA* (2002) 99: 10405-10410). There are 60 identical asymmetric structural units per AAV virion. At least 145 amino acids out of a total of 735 in each AAV-2 capsomere are exposed, to varying degrees, on the surface.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology,* 2nd Edition, vol. I & II (B. N. Fields and D. M. Knipe, eds.); *Handbook of Experimental Immunology,* Vols. I-IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By an "AAV vector" is meant a vector derived from any adeno-associated virus serotype isolated from any animal species, including without limitation, AAV-1, AAV-2, AAV-3, AAV-4, AAV-5, AAV-6, AAV-7, AAV-8, AAV-G1 and AAV-C1. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs and vectors that encode Rep and/or Cap expression products have been described. See, e.g., U.S. Pat. Nos. 6,001,650, 5,139,941 and 6,376,237, all incorporated herein by reference in their entireties; Samulski et al. (1989) *J. Virol.* 63: 3822-3828; and McCarty et al. (1991) *J. Virol.* 65: 2936-2945.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

It has been demonstrated that the full-complement of adenovirus genes are not required for accessory helper functions. In particular, adenovirus mutants incapable of DNA replication and late gene synthesis have been shown to be permissive for AAV replication. Ito et al., (1970) *J. Gen. Virol.* 9: 243; Ishibashi et al, (1971) *Virology* 45: 317. Similarly, mutants within the E2B and E3 regions have been shown to support AAV replication, indicating that the E2B and E3 regions are probably not involved in providing accessory functions. Carter et al., (1983) *Virology* 126: 505. However, adenoviruses defective in the E1 region, or having a deleted E4 region, are unable to support AAV replication. Thus, E1A and E4 regions are likely required for AAV replication, either directly or indirectly. Laughlin et al., (1982) *J. Virol.* 41: 868; Janik et al., (1981) *Proc. Natl. Acad. Sci. USA* 78: 1925; Carter et al., (1983) *Virology* 126: 505. Other characterized Ad mutants include: E1B (Laughlin et al. (1982), supra; Janik et al. (1981), supra; Ostrove et al., (1980) *Virology* 104: 502); E2A (Handa et al., (1975) *J. Gen. Virol.* 29: 239; Strauss et al., (1976) *J. Virol.* 17: 140; Myers et al., (1980) *J. Virol.* 35: 665; Jay et al., (1981) *Proc. Natl. Acad. Sci. USA* 78: 2927; Myers et al., (1981) *J. Biol. Chem.* 256: 567); E2B (Carter, *Adeno-Associated Virus Helper Functions, in I CRC Handbook of Parvoviruses* (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) *J. Virol.* 62: 206-210, recently reported that E1B55k is required for AAV virion production, while E1B19k is not. In addition, International Publication WO 97/17458 and Matshushita et al., (1998) *Gene Therapy* 5: 938-945, describe accessory function vectors encoding various Ad genes. Particularly preferred accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such vectors are described in International Publication No. WO 01/83797.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus including an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

A "caprine recombinant AAV virion" or "caprine rAAV virion" is a rAAV virion as described above that has been produced using AAV helper functions that include a gene encoding a caprine capsid protein, such as caprine VP1.

A "bovine recombinant AAV virion" or "bovine rAAV virion" is a rAAV virion as described above that has been produced using AAV helper functions that include a gene encoding a bovine capsid protein, such as a bovine VP1.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52 : 456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13: 197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3: 353-358, National Biomedical Research Foundation, Washington, D.C., which adapts the local homology algorithm of Smith and Waterman *Advances in Appl. Math.* 2: 482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* supra; *Nucleic Acid Hybridization,* supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta -D-mannosylqueosine, 5'-methoxycarbonylmethyluracil, 5-methoxyuracil, 2-methylthio -N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3 prime (3')" or "5 prime (5')" relative to another sequence, it is to be understood that it is the position of the sequences in the "sense" or "coding" strand of a DNA molecule that is being referred to as is conventional in the art.

A "functional homologue," or a "functional equivalent" of a given AAV polypeptide includes molecules derived from the native polypeptide sequence, as well as recombinantly produced or chemically synthesized polypeptides which function in a manner similar to the reference AAV molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

By "capable of efficient transduction" is meant that the mutated constructs of the invention provide for rAAV vectors or virions that retain the ability to transfect cells in vitro and/or in vivo at a level that is within 1-10% of the transfection efficiency obtained using the corresponding wild-type sequence. Preferably, the mutant retains the ability to transfect cells or tissues at a level that is within 10-100% of the corresponding wild-type sequence. The mutated sequence may even provide for a construct with enhanced ability to transfect cells and tissues. Transduction efficiency is readily determined using techniques well known in the art, including the in vitro transduction assay described in the Examples.

By "reduced immunoreactivity" is meant that the mutated AAV construct reacts with anti-AAV antibodies at a reduced level as compared to the corresponding wild-type AAV construct. The term "antibody" as used herein includes antibodies obtained from both polyclonal and monoclonal preparations, as well as, the following: hybrid (chimeric) antibody molecules (see, for example, Winter et al. (1991) *Nature* 349:293-299; and U.S. Pat. No. 4,816,567); F(ab')2 and F(ab) fragments; Fv molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain immunological binding properties of the parent antibody molecule.

The mutated constructs of the present invention can have reduced immunoreactivity as determined using in vitro and/or in vivo assays using any of the above types of antibodies that have been generated against the corresponding wild-type AAV construct. Preferably, the mutated AAV construct will react with such antibodies at a level at least 1.5 times lower than the corresponding wild-type construct, preferably at a level at least 2 times lower, such as at least 5-10 times lower, even at a level at least 50-100 times or at least 1000 times lower than the corresponding wild-type construct.

Preferably, the mutated AAV construct reacts at a reduced level with anti-AAV neutralizing antibodies. For example, the mutated constructs will preferably be at least 1.5 times more neutralization-resistant than the corresponding wild-type, preferably at least 2 times more neutralization-resistant, even more preferably at least 5-10 times or more, such as at least 50-100 times or more neutralization-resistant than the corresponding wild-type, as determined using standard assays, such as the in vitro neutralization assays described herein The terms "subject", "individual" or "patient" are used interchangeably herein and refer to a vertebrate, preferably a mammal. Mammals include, but are not limited to, murines, rodents, simians, humans, farm animals, sport animals and pets.

The terms "effective amount" or "therapeutically effective amount" of a composition or agent, as provided herein, refer to a nontoxic but sufficient amount of the composition or agent to provide the desired response. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

"Treating" or "treatment" of a disease includes: (1) preventing the disease, i.e. causing the clinical symptoms of the disease not to develop in a subject that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery of novel mutant AAV sequences useful in the production of rAAV virions that display reduced immunoreactivity as compared to the corresponding wild-type virions. Furthermore, the mutants preferably retain other properties of the corresponding wild-type, such as DNA packaging, receptor binding, chromatographic purification, and the ability to transduce cells in vitro and in vivo. Preferably, such properties are within at least 1-10% of the values measured for the corresponding AAV wild-type. More preferably such properties are within 10-100% of the values measured for the corresponding AAV wild-type. Most preferably such properties are at least 100% or more of the values measured for the corresponding AAV wild-type. Thus, for example, if the mutation is in an AAV-2 capsid sequence, the comparison of these attributes would be between an AAV-2 virion with the mutated capsid sequence versus an AAV-2 virion with the same components as the mutated virion except with the AAV-2 wild-type capsid protein sequence.

As explained above, the AAV mutants of the subject invention preferably display decreased immunoreactivity relative to neutralizing antibodies that may be present in the host to which the mutant virions are administered. In this way, cells and tissues of subjects that have either been naturally infected with AAV (i.e., due to previous natural infection) or artificially infected with AAV (i.e., due to previous gene therapy or nucleic acid immunization) may be more efficiently transfected with recombinant AAV virions in order to treat or prevent new or on-going disease.

A well-studied mechanism for neutralization is that a neutralizing antibody physically blocks a region on the virus required to bind to receptors that are required for infection. Previous studies with other viruses have shown that the receptors and neutralizing antibodies bind to a distinct set of amino acids and that it is possible to identify mutants at particular positions on viral capsids that affect the binding of neutralizing antibodies, but not receptors or other functions needed for viral infection. Experiments in which wild-type replicating viruses are selected to be resistant to neutralizing antibodies have shown that mutations, even in single amino acids, such as those described here, can result in significant increases in resistance to antibody neutralization.

The ability or inability of an AAV mutant virion to bind AAV antisera is partially a function of the sequence of the capsid proteins (encoded by AAV cap gene). Thus, the invention contemplates single, double, triple, quadruple and more amino acid changes made on the surface of the AAV virion, as well as deletions and/or insertions, in order to decrease immunoreactivity, e.g., to alter the ability of the AAV virion to bind AAV antisera. Such mutants may be assessed for resistance to neutralization and, if necessary, more drastic or multiple changes can be made.

Figure 11:
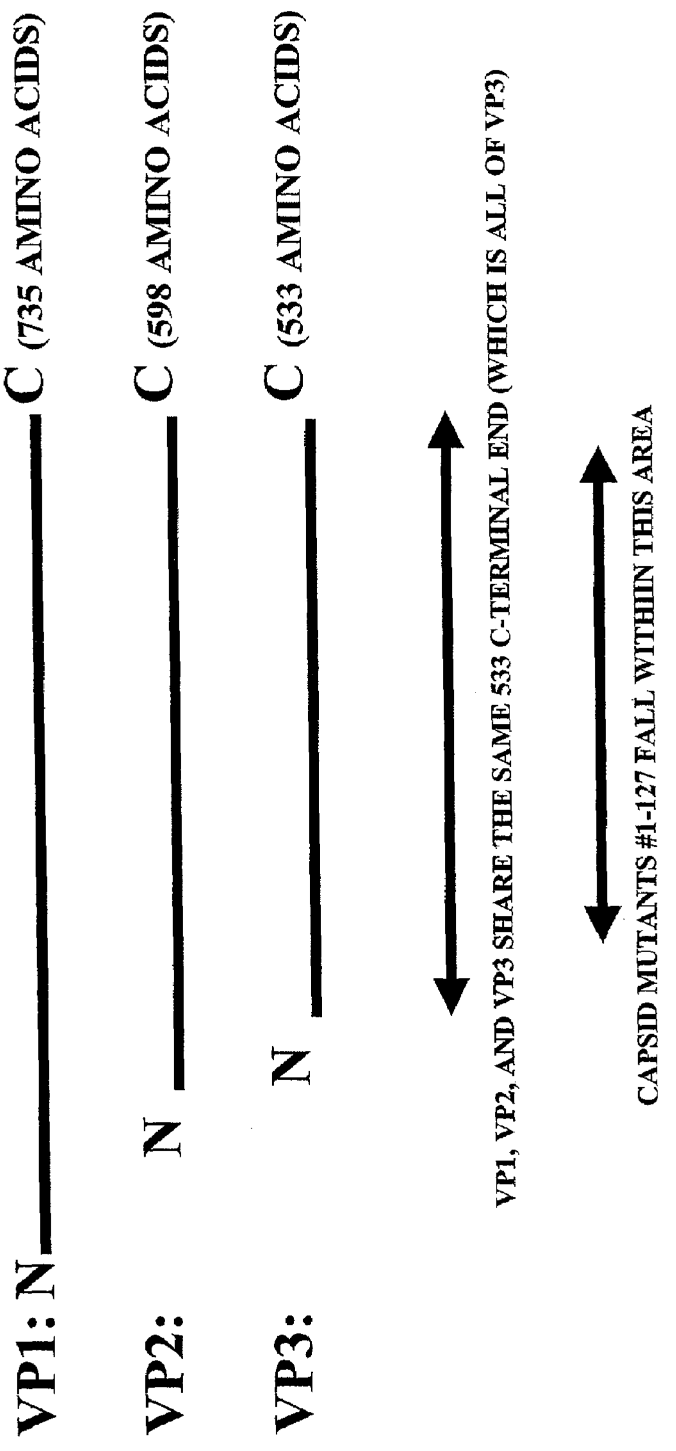
FIG. 11 shows the relative positions of AAV-2 capsid proteins VP1, VP2 and VP3. As shown in the figure, VP1, VP2 and VP3 share the same 533 C-terminal amino acids which make up VP3. As shown in the figure, all capsid mutants described herein fall within the shared area.

Methods of identifying portions of the AAV virion amenable to mutation with a resulting functional rAAV virion are described in the examples below. As detailed therein, mutations to amino acids on the viral surface, such as mutations to protruding features of the capsid, including portions of the capsid known as the "spike," "cylinder" and "plateau" are preferred. Mutations are preferably to the VP2 region, more preferably to the VP3 region, and in particular, within the region of overlap between VP1, VP2 and VP3 as shown in FIG. 11. Particularly preferred mutations are found within positions 80-598 of VP2 (corresponding to amino acids 217-735 of VP1 and amino acids 15-533 of VP3).

The sequence of a representative VP2 is shown in FIG. 9 herein (SEQ ID NO:12). The major coat protein, VP3 spans amino acids 203-735 of VP1. The mutation comprises at least one amino acid substitution, deletion or insertion to the native protein. Representative mutations include one or more substitutions of the amino acids occurring at a position corresponding to a position of the AAV-2 VP2 capsid protein selected from the group consisting of amino acids 126, 127, 128, 130, 132, 134, 247, 248, 315, 334, 354, 357, 360, 361, 365, 372, 375, 377, 390, 393, 394, 395, 396, 407, 411, 413, 418, 437, 449, 450, 568, 569, and 571.

Generally, the naturally occurring amino acid is substituted with an amino acid that has a small side-chain and/or is uncharged and is therefore less immunogenic. Such amino acids include, without limitation, alanine, valine, glycine, serine, cysteine, proline, as well as analogs thereof, with alanine preferred. Moreover, additional mutations can be present. Representative combinations include any combination of the amino acids identified immediately above, such as but not limited to a mutation of amino acid 360 to histidine and amino acid 361 to alanine; amino acid 334 to alanine and amino acid 449 to alanine; amino acid 334 to alanine and amino acid 568 to alanine, amino acid 568 to alanine and amino acid 571 to alanine; amino acid 334 to alanine, amino acid 449 to alanine and amino acid 568 to alanine; amino acid 571 to lysine and any of the amino acids specified above. The above combinations are merely illustrative and of course numerous other combinations are readily determined based on the information provided herein.

As described further in the examples, certain amino acids in the capsid are adjacent to the heparin-binding site. This region is termed the "dead zone" or "DZ" herein and includes amino acids G128, N131, D132, H134, N245, N246, D356, D357, H372, G375, D391, D392, E393 and E394. Amino acids in the dead zone are important for function of AAV and are thus also targets for the binding of neutralizing antibodies. As this region is important for AAV function, conservative amino acid substitutions, such as Q for H, D for E, E or N for D, and the like, are preferred in the dead zone region and result in a more functional dead zone mutant.

The various amino acid positions occurring in the capsid protein are numbered herein with reference to the AAV-2 VP2 sequence described in NCBI Accession No. AF043303 and shown in FIG. 9 herein. FIG. 10 shows the amino acid sequence of AAV-2 VP1. However, it is to be understood that mutations of amino acids occurring at corresponding positions in any of the AAV serotypes are encompassed by the present invention. The sequences for the capsid from various AAV serotypes isolated from multiple species are known and described in, e.g., Gao et al. (2002) *Proc. Natl. Acad. Sci. USA* 99:11854-11859; Rutledge et al. (1998) *J. Virol.* 72:309-319; NCBI Accession Nos. NC001863; NC004828; NC001862; NC002077; NC001829; NC001729; U89790; U48704; AF369963; AF028705; AF028705; AF028704; AF513852; AF513851; AF063497; AF085716; AF43303; Y18065; AY186198; AY243026; AY243025; AY243024; AY243023; AY243022; AY243021; AY243020; AY243019; AY243018; AY243017; AY243016; AY243015; AY243014; AY243013; AY243012; AY243011; AY243010; AY243009; AY243008; AY243007; AY243006; AY243005; AY243004; AY243003; AY243002; AY243001; AY243000; AY242999; AY242998; and AY242997, all of which are incorporated herein in their entireties.

Moreover, the inventors herein have discovered a new caprine AAV, isolated from goat, termed "AAV-G1" herein. The caprine AAV VP1 sequence is highly homologous to the VP1 sequence of AAV-5, but is approximately 100 times more resistant to neutralization by existing AAV antibodies than the native AAV-5 sequence. More particularly, a 2805 bp PCR fragment of the caprine AAV described herein, encoding 603 bp of rep, the central intron, and all of cap, shows 94% homology to the corresponding AAV-5 sequence. The DNA and protein homologies for the partial rep are 98% and 99%, respectively. A comparison of the caprine VP1 coding sequence with a primate AAV-5 VP1 coding sequence is shown in FIGS. 12A-12B. The DNA for the cap region of the caprine AAV is 93% homologous to that of AAV-5. The amino acid sequences for the caprine VP1 versus a primate AAV-5 is shown in FIG. 13. The caprine sequence encodes a VP1 protein of 726 amino acids, while AAV-5 VP1 is 724 amino acids in length. Additionally, the sequences display 94% sequence identity and 96% sequence similarity. There are 43 amino acid differences between the caprine and the primate AAV-5 VP1 sequence. With respect to the linear amino acid sequence of VP1, the distribution of the amino acid differences between AAV-5 and caprine AAV is highly polar. All of the amino acid differences occur exclusively in the C-terminal hypervariable region of VP1 in a scattered fashion. This region relative to AAV-5 and caprine includes approximately 348 amino acids from amino acid 386 to the C-terminus, numbered relative to AAV-5 VP1. The corresponding hypervariable regions in other AAV serotypes are readily identifiable and the region from a number of AAV serotypes is shown in the figures herein.

Without being bound by a particular theory, the fact that all of the amino acid differences in VP1 of AAV-5 and caprine AAV occur in regions that are probably surface exposed, implies that capsid evolution is being driven primarily by the humoral immune system of the new host and/or by adaptation to ruminant receptors.

A comparison of the VP1 sequence from caprine AAV with a number of other primate VP1 sequences, including AAV-1, AAV-2, AAV-3B, AAV-4, AAV-6, AAV-8 and AAV-5, is shown in FIGS. 14A-14H. The accessibility of the various amino acid positions based on the crystal structure is also shown in the figures. Moreover, the surface features of the amino acids, the location of single mutations that decrease binding and neutralization; the heparin binding sites; possible Mg2+ contact; the phospholipase A2 domain; as well as positions likely for base contact and DNA binding, possible phosphate and ribose contact are also shown. As can be seen in the figure, AAV-5 and caprine AAV are identical to each other at 17 positions that differ in both AAV-2 and AAV-8.

Similarly, the inventors herein have discovered a new bovine AAV, isolated from cow, termed "AAV-C1" herein. The AAV-C1 VP1 nucleotide and amino acid sequences are shown in FIGS. 20A and 20B, respectively. FIGS. 21A-21H show a comparison of the amino acid sequence of VP1 from AAV-C1 with primate AAV-1, AAV-2, AAV-3B, AAV-4, AAV-6, AAV-8, AAV-5 and caprine AAV (AAV-G1). The accessibility of the various amino acid positions based on the crystal structure is also shown in the figures. Moreover, the surface features of the amino acids, the location of single mutations that decrease binding and neutralization; the heparin binding sites; possible Mg2+ contact; the phospholipase A2 domain; as well as positions likely for base contact and DNA binding, possible phosphate and ribose contact are also shown.

As can be seen in the figure, VP1 from AAV-C1 shows approximately 76% identity with AAV-4. The sequence differences between AAV-4 and AAV-C1 are scattered throughout the capsid. AAV-C1 VP1 displays approximately 54% identity with AAV-5 VP1, with high homology in the Rep protein, the first 137 amino acids of AAV-5 VP1 and the non translated region after the stop of AAV-5 VP1 (not shown). Thus, AAV-C1 appears to be a natural hybrid between AAV-5 and AAV-4. AAV-C1 also displayed approximately 58% sequence identity with VP1s from AAV-2 and AAV-8, approximately 59% sequence identity with VP1s from AAV-1 and AAV-6, and approximately 60% sequence identity with VP1 from AAV-3B.

As described in more detail in the examples, the bovine AAV is approximately 16 times more resistant to neutralization by existing AAV antibodies than the native AAV-2 sequence. Thus, the caprine and bovine sequences, and other such non-primate mammalian sequences, can be used to produce recombinant AAV virions with decreased immunoreactivity relative to primate AAV sequences, such as relative to AAV-2 and AAV-5. Additionally, regions of AAV capsids that can be mutated to provide AAV virions with reduced immunoreactivity from non-caprine and non-bovine AAV isolates and strains, such as any of the AAV serotypes, can be reasonably predicted based on the caprine and bovine AAV sequences provided herein and a comparison of these sequences and immunoreactive properties with those of other isolates and serotypes.

Based on the above discussion, and the examples provided herein, one of skill in the art can reasonably predict mutations that can be made to wild-type AAV sequences in order to generate AAV virions with decreased immunoreactivity. Amino acid changes to amino acids found on the AAV capsid surface, and especially those in the hypervariable region, are expected to provide AAV virions with decreased immunoreactivity. Moreover, based on the knowledge provided by the caprine and bovine AAV sequences, other non-primate mammalian AAVs can be identified to provide non-mutated AAV sequences for use in preparing recombinant AAV virions with decreased immunoreactivity relative to primate AAVs, such as AAV-2 and AAV-5. For example, as shown in the examples below, positions in AAV-2 mutants that correlate to neutralization resistance and that are in common between the AAV-2 mutants and caprine AAV include changes to positions 248, 354, 360, 390, 407, 413 and 449 of AAV-2.

The AAV mutants of the present invention can be generated by site-directed mutagenesis of the AAV cap gene region. The mutated cap region can then be cloned into a suitable helper function vector, and rAAV virions generated using the mutated helper function vector and any suitable transfection method, including the triple transfection method described herein. Mutants suitable for use with the present invention are identified by their reduced immunoreactivity, as defined above. Preferably, the mutants of the present invention have a reduced ability to be neutralized by anti-AAV antisera, preferably anti-AAV-2 antisera, while maintaining other biological functions such as the ability to assemble intact virions, package viral DNA, bind cellular receptors, and transduce cells.

Thus, the present invention involves the identification and use of mutated AAV sequences, as well as wild-type non-primate mammalian AAV sequences, displaying decreased immunoreactivity for incorporation into rAAV virions. Such rAAV virions can be used to deliver a "heterologous nucleic acid" (an "HNA") to a vertebrate subject, such as a mammal. As explained above, a "recombinant AAV virion" or "rAAV virion" is an infectious virus composed of an AAV protein shell (i.e., a capsid) encapsulating a "recombinant AAV (rAAV) vector," the rAAV vector comprising the HNA and one or more AAV inverted terminal repeats (ITRs). AAV vectors can be constructed using recombinant techniques that are known in the art and include one or more HNAs flanked by functional ITRs. The ITRs of the rAAV vector need not be the wild-type nucleotide sequences, and may be altered, e.g., by the insertion, deletion, or substitution of nucleotides, so long as the sequences provide for proper function, i.e., rescue, replication, and packaging of the AAV genome.

Recombinant AAV virions may be produced using a variety of techniques known in the art, including the triple transfection method (described in detail in U.S. Pat. No. 6,001,650, the entirety of which is incorporated herein by reference). This system involves the use of three vectors for rAAV virion production, including an AAV helper function vector, an accessory function vector, and a rAAV vector that contains the HNA. One of skill in the art will appreciate, however, that the nucleic acid sequences encoded by these vectors can be provided on two or more vectors in various combinations. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

The AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Examples of vectors suitable for use with the present invention include pHLP19, described in U.S. Pat. No. 6,001,650 and pRep6cap6 vector, described in U.S. Pat. No. 6,156,303, the entirety of both incorporated by reference herein.

The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. In a preferred embodiment, the accessory function plasmid pladeno5 is used (details regarding pLadeno5 are described in U.S. Pat. No. 6,004,797, the entirety of which is hereby incorporated by reference). This plasmid provides a complete set of adenovirus accessory functions for AAV vector production, but lacks the components necessary to form replication-competent adenovirus.

The rAAV vector containing the heterologous nucleic acid (HNA) may be constructed using ITRs from any of the various AAV serotypes. The HNA comprises nucleic acid sequences joined together that are otherwise not found together in nature, this concept defining the term "heterologous." To illustrate the point, an example of an HNA is a gene flanked by nucleotide sequences not found in association with that gene in nature. Another example of an HNA is a gene that itself is not found in nature (e.g., synthetic sequences having codons different from the native gene). Allelic variation or naturally occurring mutational events do not give rise to HNAs, as used herein. An HNA can comprise an anti-sense RNA molecule, a ribozyme, or a gene encoding a polypeptide.

The HNA is operably linked to a heterologous promoter (constitutive, cell-specific, or inducible) such that the HNA is capable of being expressed in the patient's target cells under appropriate or desirable conditions. Numerous examples of constitutive, cell-specific, and inducible promoters are known in the art, and one of skill could readily select a promoter for a specific intended use, e.g., the selection of the muscle-specific skeletal α-actin promoter or the muscle-specific creatine kinase promoter/enhancer for muscle cell-specific expression, the selection of the constitutive CMV promoter for strong levels of continuous or near-continuous expression, or the selection of the inducible ecdysone promoter for induced expression. Induced expression allows the skilled artisan to control the amount of protein that is synthesized. In this manner, it is possible to vary the concentration of therapeutic product. Other examples of well known inducible promoters are: steroid promoters (e.g., estrogen and androgen promoters) and metallothionein promoters.

The invention includes novel mutant virions comprising HNAs coding for one or more anti-sense RNA molecules, the rAAV virions preferably administered to one or more muscle cells or tissue of a mammal. Antisense RNA molecules suitable for use with the present invention in cancer anti-sense therapy or treatment of viral diseases have been described in the art. See, e.g., Han et al., (1991) *Proc. Natl. Acad. Sci. USA* 88:4313-4317; Uhlmann et al., (1990) *Chem. Rev.* 90:543-584; Helene et al., (1990) *Biochim. Biophys. Acta.* 1049:99-125; Agarawal et al., (1988) *Proc. Natl. Acad. Sci. USA* 85:7079-7083; and Heikkila et al., (1987) *Nature* 328:445-449. The invention also encompasses the delivery of ribozymes using the methods disclosed herein. For a discussion of suitable ribozymes, see, e.g., Cech et al., (1992) *J. Biol. Chem.* 267:17479-17482 and U.S. Pat. No. 5,225,347.

The invention preferably encompasses mutant rAAV virions comprising HNAs coding for one or more polypeptides, the rAAV virions preferably administered to one or more cells or tissue of a mammal. Thus, the invention embraces the delivery of HNAs encoding one or more peptides, polypeptides, or proteins, which are useful for the treatment or prevention of disease states in a mammalian subject. Such DNA and associated disease states include, but are not limited to: DNA encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain alpha-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding omithine transcarbamylase, associated with omithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotinidase, associated with biotinidase deficiency; DNA encoding beta-glucocerebrosidase, associated with Gaucher disease; DNA encoding beta-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding alpha-1 antitrypsin for treatment of alpha-1 antitrypsin deficiency (emphysema); DNA encoding erythropoietin for treatment of anemia due to thalassemia or to renal failure; DNA encoding vascular endothelial growth factor, DNA encoding angiopoietin-1, and DNA encoding fibroblast growth factor for the treatment of ischemic diseases; DNA encoding thrombomodulin and tissue factor pathway inhibitor for the treatment of occluded blood vessels as seen in, for example, atherosclerosis, thrombosis, or embolisms; DNA encoding aromatic amino acid decarboxylase (AADC), and DNA encoding tyrosine hydroxylase (TH) for the treatment of Parkinson's disease; DNA encoding the beta adrenergic receptor, DNA encoding anti-sense to, or DNA encoding a mutant form of, phospholamban, DNA encoding the sarco (endo)plasmic reticulum adenosine triphosphatase-2 (SERCA2), and DNA encoding the cardiac adenylyl cyclase for the treatment of congestive heart failure; DNA encoding a tumor suppessor gene such as p53 for the treatment of various cancers; DNA encoding a cytokine such as one of the various interleukins for the treatment of inflammatory and immune disorders and cancers; DNA encoding dystrophin or minidystrophin and DNA encoding utrophin or miniutrophin for the treatment of muscular dystrophies; and, DNA encoding insulin for the treatment of diabetes.

The invention also includes novel mutant virions comprising a gene or genes coding for blood coagulation proteins, which proteins may be delivered, using the methods of the present invention, to the cells of a mammal having hemophilia for the treatment of hemophilia. Thus, the invention includes: delivery of the Factor IX gene to a mammal for treatment of hemophilia B, delivery of the Factor VIII gene to a mammal for treatment of hemophilia A, delivery of the Factor VII gene for treatment of Factor VII deficiency, delivery of the Factor X gene for treatment of Factor X deficiency, delivery of the Factor XI gene for treatment of Factor XI deficiency, delivery of the Factor XIII gene for treatment of Factor XIII deficiency, and, delivery of the Protein C gene for treatment of Protein C deficiency. Delivery of each of the above-recited genes to the cells of a mammal is accomplished by first generating a rAAV virion comprising the gene and then administering the rAAV virion to the mammal. Thus, the invention includes rAAV virions comprising genes encoding any one of Factor IX, Factor VIII, Factor X, Factor VII, Factor XI, Factor XIII or Protein C.

Delivery of the recombinant virions containing one or more HNAs to a mammalian subject may be by intramuscular injection or by administration into the bloodstream of the mammalian subject. Administration into the bloodstream may be by injection into a vein, an artery, or any other vascular conduit the mutant virions into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403 and herein incorporated by reference, can also be employed by the skilled artisan to administer the mutant virions into the vasculature of an isolated limb to potentially enhance transduction into muscle cells or tissue. Moreover, for certain conditions, it may be desirable to deliver the mutant virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAV virions or cells transduced in vitro may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

The dose of rAAV virions required to achieve a particular "therapeutic effect," e.g., the units of dose in vector genomes/per kilogram of body weight (vg/kg), will vary based on several factors including, but not limited to: the route of rAAV virion administration, the level of gene (or anti-sense RNA or ribozyme) expression required to achieve a therapeutic effect, the specific disease or disorder being treated, a host immune response to the rAAV virion, a host immune response to the gene (or anti-sense RNA or ribozyme) expression product, and the stability of the gene (or anti-sense RNA or ribozyme) product. One of skill in the art can readily determine a rAAV virion dose range to treat a patient having a particular disease or disorder based on the aforementioned factors, as well as other factors that are well known in the art.

Generally speaking, by "therapeutic effect" is meant a level of expression of one or more HNAs sufficient to alter a component of a disease (or disorder) toward a desired outcome or clinical endpoint, such that a patient's disease or disorder shows clinical improvement, often reflected by the amelioration of a clinical sign or symptom relating to the disease or disorder. Using hemophilia as a specific disease example, a "therapeutic effect" for hemophilia is defined herein as an increase in the blood-clotting efficiency of a mammal afflicted with hemophilia, efficiency being determined, for example, by well known endpoints or techniques such as employing assays to measure whole blood clotting time or activated prothromboplastin time. Reductions in either whole blood clotting time or activated prothromboplastin time are indications of an increase in blood-clotting efficiency. In severe cases of hemophilia, hemophiliacs having less than 1% of normal levels of Factor VIII or Factor IX have a whole blood clotting time of greater than 60 minutes as compared to approximately 10 minutes for non-hemophiliacs. Expression of 1% or greater of Factor VIII or Factor IX has been shown to reduce whole blood clotting time in animal models of hemophilia, so achieving a circulating Factor VIII or Factor IX plasma concentration of greater than 1% will likely achieve the desired therapeutic effect of an increase in blood-clotting efficiency.

The constructs of the present invention may alternatively be used to deliver an HNA to a host cell in order to elucidate its physiological or biochemical function(s). The HNA can be either an endogenous gene or heterologous. Using either an ex vivo or in vivo approach, the skilled artisan can administer the mutant virions containing one or more HNAs of unknown function to an experimental animal, express the HNA(s), and observe any subsequent functional changes. Such changes can include: protein-protein interactions, alterations in biochemical pathways, alterations in the physiological functioning of cells, tissues, organs, or organ systems, and/or the stimulation or silencing of gene expression.

Alternatively, the skilled artisan can of over-express a gene of known or unknown function and examine its effects in vivo. Such genes can be either endogenous to the experimental animal or heterologous in nature (i.e., a transgene).

By using the methods of the present invention, the skilled artisan can also abolish or significantly reduce gene expression, thereby employing another means of determining gene function. One method of accomplishing this is by way of administering antisense RNA-containing rAAV virions to an experimental animal, expressing the antisense RNA molecule so that the targeted endogenous gene is "knocked out," and then observing any subsequent physiological or biochemical changes.

The methods of the present invention are compatible with other well-known technologies such as transgenic mice and knockout mice and can be used to complement these technologies. One skilled in the art can readily determine combinations of known technologies with the methods of the present invention to obtain useful information on gene function.

Once delivered, in many instances it is not enough to simply express the HNA; instead, it is often desirable to vary the levels of HNA expression. Varying HNA expression levels, which varies the dose of the HNA expression product, is frequently useful in acquiring and/or refining functional information on the HNA. This can be accomplished, for example by incorporating a heterologous inducible promoter into the rAAV virion containing the HNA so that the HNA will be expressed only when the promoter is induced. Some inducible promoters can also provide the capability for refining HNA expression levels; that is, varying the concentration of inducer will fine-tune the concentration of HNA expression product. This is sometimes more useful than having an "on-off" system (i.e., any amount of inducer will provide the same level of HNA expression product, an "all or none" response). Numerous examples of inducible promoters are known in the art including the ecdysone promoter, steroid promoters (e.g., estrogen and androgen promoters) and metallothionein promoters.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Recombinant AAV-LACZ Mutant Virion Preparation and Properties Thereof

Recombinant AAV-2 virions containing the β-galactosidase gene (rAAV-2 lacZ) were prepared using a triple-transfection procedure described in U.S. Pat. No. 6,001,650, incorporated herein by reference in its entirety. The complete cDNA sequence for β-gal is available under GenBank Accession No. NC 000913 REGION: complement (362455 . . . 365529).

I. Vector Construction

A. Mutant AAV Helper Function Vector

Based on the structure of AAV-2 (see, Xie et al. *Proc. Natl. Acad. Sci. USA* (2002) 99:10405-10410), 61 mutants were constructed by oligonuecleotide-directed, site-specific mutagenesis. The entire surface of AAV is composed of 60 identical asymmetrical structural units arranged in an icosahedral shape. This has two important implications. First, any single amino acid mutation that is made will be found at 60 places on the virus all at the same position relative to other amino acids within the asymmetrical structural unit. Second, by studying a single asymmetrical structural unit one can understand the entire surface of the virus.

AAV-2 structure was determined as follows. Coordinates for the monomeric AAV-2 capsid protein (VP1 amino acids 217-735; VP2 amino acids 80-598) were obtained from the Protein Data Bank (identification number 1LP3). The structure was analyzed using Swiss PDB Viewer version 3.7, Vector NTI 3D-Mol version 8.0 (Invitrogen, Inc.), or Chime (MDL Information Systems, Inc. Multimeric structures of the AAV-2 capsid were generated using the oligomer generator program on the Virus Particle Explorer (VIPER) website, using the coordinate transformation functions of Swiss PDB viewer in conjunction with matrix coordinates in the PBD (1LP3) file, or downloaded from the protein quaternary structure database at the European Bioinformatics Institute (filename=1lp3). Possible antibody binding sites on AAV-2 capsid multimers were analyzed by constructing the asymmetric structural unit of AAV-2 capsid and then manually docking an IgG structure (murine IgG2a monoclonal antibody; PDB ID number 1IGT) to that structure or to other multimeric units of the AAV-2 capsid using Swiss PDB Viewer. Distances, amino acid clashes, and contact areas between the IgG and the AAV-2 capsid could be assessed using the appropriate tools within the Swiss PDB Viewer program.

Figure 2:
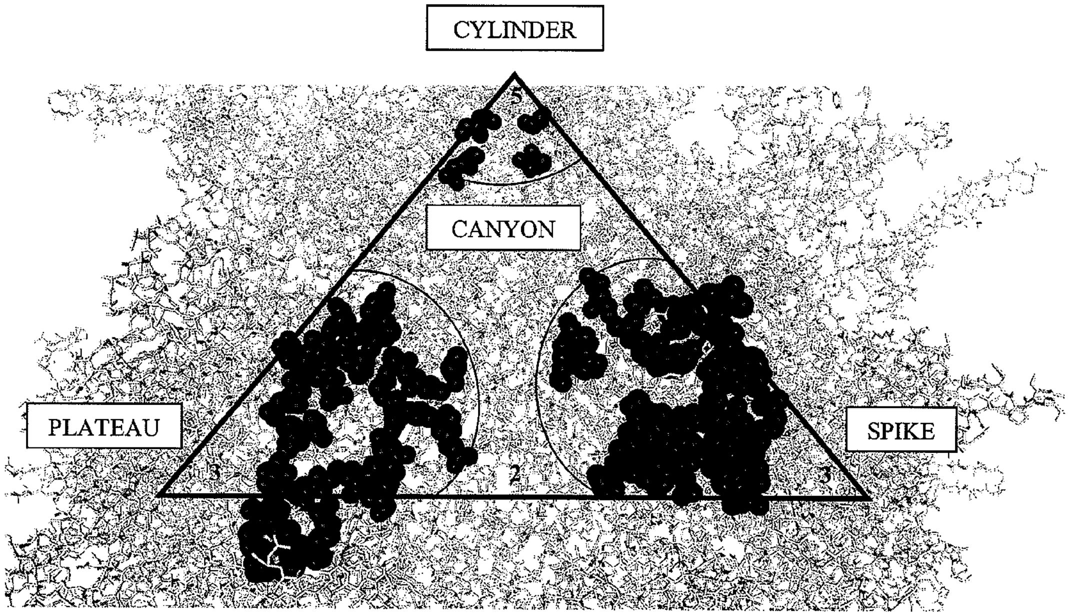
FIG. 2 illustrates the location of some of the amino acids that were mutated as described in the examples within an asymmetric unit (black triangle) of the AAV-2 structure. The amino acids that were mutated are shown as black space-filling models, while those that were not mutated are shown as white stick models. The location of major surface features (spike, cylinder, plateau, canyon) is indicated and the approximate boundaries of these features are shown by thin circular black lines. The "canyon" regions, predicted to be relatively inaccessible to antibody binding, are located in the areas between the spike, cylinder, and plateau. The numbers 2, 3 and 5 represent the 2-, 3-, and 5-fold axes of symmetry, respectively.

Several criteria were applied to select which amino acids out of a total of about 145 external, surface-exposed amino acids (within each of the 60 identical asymmetric structural units, see FIG. 1) to mutate. Mutations were made only in external "surface-exposed" amino acids, although it is possible for amino acids under the external surface or on the internal surface to influence antibody binding. The amino acids that were mutated were those with side-chains predicted to be the most accessible to antibody binding. This included amino acids on protruding features of the capsid, known as the "spike", "cylinder", and "plateau." Such protruding features are often targets for the binding of neutralizing antibodies. Amino acids in areas that were not wide enough to accommodate an antibody ("canyon", "dimple", center of 3-fold symmetry axis, center of 5-fold symmetry axis) were not mutated. Furthermore the amino acid side-chain was selected based on an exposed area of at least 20 Å$^2$, because decreases of 20 Å$^2$ or more in the contact area between an antigen and an antibody (out of a total contact area of approximately 600 Å$^2$ to 900 Å$^2$) can have a measurable effect on antibody-antigen affinity and therefore on the neutralizing titer of the antibody. Amino acids selected were those with the side-chain (and not just the peptide backbone) exposed. It was assumed that if only the peptide backbone was exposed then an antibody that bound to such an amino acid may not be able to discriminate various amino acids well, since all amino acids have the same peptide backbone. Finally, relatively flat areas of protein antigens often interact with relatively flat areas of antibodies so amino acids chosen for mutation were in a relatively flat area (side of spike, top of cylinder, top of plateau). Applying all of the above criteria to the approximately 145 capsid amino acids located on the external surface of AAV-2 resulted in the selection of 72 positions that would be most likely to affect the binding of neutralizing antibodies when changed to other amino acids. The location of these amino acids is indicated in FIG. 2 and listed in Tables 1, 4 and 5.

Most of the 127 mutants (at 72 positions) that were made changed single amino acids to alanine, using techniques known by those skilled in the art of molecular biology. Alanine was chosen because it has been determined that, of all mutations that could be made, alanine is the least disruptive to protein structure. Also, since alanine only has a methyl side-chain, changing most other amino acids to alanine are likely to disrupt antibody binding. That is, compared to other amino acids, alanine is less immunogenic because it lacks a side-chain that significantly contributes to antigen/antibody contact areas and hence to antigen/antibody affinity. Note that the numbering that follows is based on the AAV-2 VP2 sequence as depicted in FIG. 9. A few positions were changed to an amino acid other than alanine. For example at position 356 where there already is an alanine, an arginine was inserted. Arginine is polar enough to remain on the AAV surface and large enough that it could interfere with binding of antibodies. There are five glycines that may be accessible to antibodies. Glycines are often found where a peptide chain turns and thus can be a critical component of structure. Mutation of glycines can be problematic because of the possibility that structure may be dramatically altered. Therefore each of the five glycines on the AAV-2 surface were considered on a case-by-case basis in order to decide what to change them to. G128 was changed to aspartate because glycine 128 is found in AAV-1 through 6 except for AAV-5 where position 128 is an aspartic acid. G191 was changed to serine because glycine 191 is found in AAV-1 through 6 except for AAV-5 where position 191 is a serine. G329 was changed to arginine because glycine 329 is found in AAV-1 through 6 except for AAV-4 where position 329 is an arginine. G375 was changed to proline because glycine 375 is conserved in AAV-1 through 6 and it was thought that proline might preserve a turn in the peptide chain found at that position. G449 was changed to alanine because, although it is serine or asparagine in other AAVs, it is between R448 and R451 in AAV-2, which are critical for heparin binding and transduction. Therefore position 449 was mutated to an amino acid closest in size to glycine (i.e., alanine). In some cases double mutants were isolated (S130A/N131A, N360H/S361A, S361A/N358K, S361A/S494P, S361A/R592K) in addition to the desired mutant. These were presumably a result of polymerase errors introduced during the mutagenesis, but were assayed like the other mutants.

AAV helper function vectors were constructed using pHLP19 (described in U.S. Pat. No. 6,001,650, incorporated herein by reference in its entirety), 116 mutagenic oligodeoxynucleotides, and an in vitro mutagenesis kit (Quik Change XL, Stratagene, San Diego, Calif.). Briefly, two complementary oligodeoxynucleotides that contain each desired mutant sequence and have a melting temperature between 74-83° C. (calculated using the equation: Tm=81.5+0.41 (% G+C)−(675/N)−% mismatch, where G is guanosine, C is cytosine, N is primer length in nucleotides) were mixed separately with pHLP19. Three cycles of PCR were done using the following conditions: denaturation was performed at 95° C. for 1 min, annealing was performed at 60° C. for 1 min, and extension was performed at 68° C. for 1 min. Then the two separate reactions were mixed and subjected to 18 additional cycles of PCR using the following conditions: denaturation was performed at 95° C. for 1 min, annealing was performed at 60° C. for 1 min, and extension was performed at 68° C. for 15 min. The PCR products were digested with the Dpn I restriction enzyme to destroy fully methylated or hemi-methylated (i.e., non-mutant) plasmids, and then transformed into the *E. coli* strain XL-10 (Stratagene). One colony was picked from each mutagenesis reaction, 500 ng of plasmid DNA were prepared, and subjected to DNA sequencing. A subset of the mutagenic oligodeoxynucleotides were used as sequencing primers to confirm the sequences of mutants. The entire capsid gene was sequenced in each case. Most mutants could be isolated in this manner. If a mutant was not isolated by the first round of DNA sequencing, 1-3 more colonies were picked and 500 ng of plasmid DNA was prepared and subjected to DNA sequencing.

B. pLadeno5 Accessory Function Vector

The accessory function vector pLadeno5 was constructed as follows. DNA fragments encoding the E2a, E4, and VA RNA regions isolated from purified adenovirus serotype-2 DNA (obtained from Gibco/BRL) were ligated into a plasmid called pAmpscript. The pAmpscript plasmid was assembled as follows. Oligonucleotide-directed mutagenesis was used to eliminate a 623-bp region including the polylinker and alpha complementation expression cassette from pBSII s/k+ (obtained from Stratagene), and replaced with an EcoRV site. The sequence of the mutagenic oligo used on the oligonucleotide-directed mutagenesis was (SEQ ID NO:1)
5'-CCGCTACAGGGCGCGATATCAGCTCACTCAA-3'.

A polylinker (containing the following restriction sites: Bam HI; KpnI; SrfI; XbaI; ClaI; Bst1107I; SalI; PmeI; and NdeI) was synthesized and inserted into the EcoRV site created above such that the BamHI side of the linker was proximal to the f1 origin in the modified plasmid to provide the pAmpscript plasmid. The sequence of the polylinker was (SEQ ID NO:2)
5'-GGATCCGGTACCGCCCGGGCTCTAGAATCGATGTATACGTCGACGTT

TAAACCATATG-3'.

DNA fragments comprising the adenovirus serotype-2 E2a and VA RNA sequences were cloned directly into pAmpscript. In particular, a 5962-bp SrfI-KpnI(partial) fragment containing the E2a region was cloned between the SrfI and KpnI sites of pAmpscript. The 5962-bp fragment comprises base pairs 21,606-27,568 of the adenovirus serotype-2 genome. The complete sequence of the adenovirus serotype-2 genome is accessible under GenBank No. 9626158.

The DNA comprising the adenovirus serotype-2 E4 sequences was modified before it was inserted into the pAmpscript polylinker. Specifically, PCR mutagenesis was used to replace the E4 proximal, adenoviral terminal repeat with a SrfI site. The location of this SrfI site is equivalent to base pairs 35,836-35,844 of the adenovirus serotype-2 genome. The sequences of the oligonucleotides used in the mutagenesis were: 5'-AGAGGCCCGGGCGTTTTAGGGCGGAGTAACTTGC-3' (SEQ ID NO:3) and 5'-ACATACCCGCAGGCGTAGAGAC-3' (SEQ ID NO:4). A 3,192 bp E4 fragment, produced by cleaving the above-described modified E4 gene with SrfI and SpeI, was ligated between the SrfI and XbaI sites of pAmpscript which already contained the E2a and VA RNA sequences to result in the pLadeno5 plasmid. The 3,192-bp fragment is equivalent to base pairs 32,644-35,836 of the adenovirus serotype-2 genome.

C. rAAV-2 hF.IX Vector

The rAAV-2 hF.IX vector is an 11,442-bp plasmid containing the cytomegalovirus (CMV) immediate early promoter, exon 1 of hF.IX, a 1.4-kb fragment of hF.IX intron 1, exons 2-8 of h.FIX, 227 bp of h.FIX 3' UTR, and the SV40 late polyadenylation sequence between the two AAV-2 inverted terminal repeats (see, U.S. Pat. No. 6,093,392, herein incorporated by reference). The 1.4-kb fragment of hF.IX intron 1 consists of the 5' end of intron 1 up to nucleotide 1098 and the sequence from nucleotide 5882 extending to the junction with exon 2. The CMV immediate early promoter and the SV40 late polyadenylation signal sequences can be obtained from the published sequence of pCMV-Script®, which is available from the Stratagene catalog, Stratagene, La Jolla, Calif.

D. rAAV-2 lac Z Vector

Construction of the Recombinant AAV Plasmid pVmLacZ

1. A 4311 bp Xba I DNA fragment was excised from pSUB201 which contains AAV rep/cap sequences. The Xba I ends were reannealed with a 10 bp Not I synthetic oligonucleotide (5'-AGCGGCCGCT-3') (SEQ ID NO:5) to give a plasmid intermediate pUC/ITR-Not I that has both AAV ITR's (inverted terminal repeats) separated by 116 bp of residual AAV sequence and Not I linker DNA.

2. A 1319 bp Not I DNA fragment was excised from p1.1c containing CMV promoter and hGH intron sequences. This DNA sequence was inserted into the Not I site of pUC/ITR-Not I, to give the intermediate pSUB201N.

3. A 1668 bp Pvu II (5131-1493) ITR bound CMV expression cassette was excised from pSUB201N and inserted at the Pvu II site (position 12) of pWee.1a, to give the plasmid intermediate pWee.1b. The excision of the 1668bp PvuII fragment from pSUB201N removed 15 bp from the outside of each ITR, in the "A" palindromic region.

4. A 4737 bp Not I/Eco RV "AAVrep/cap" DNA sequence was excised from pGN1909 and the ends were rendered blunt by filling in the 3' recessed ends using Klenow DNA polymerase. Asc I linkers were ligated to both ends, followed by cloning this "pGN1909/AscI" DNA fragment into the backbone of pWee.1b at an Asc I site (2703), to give the intermediate pWee1909 (8188bp). This plasmid has the ITR-bound CMV expression cassette with an AAV rep/cap gene backbone.

5. A 3246 bp Sma I/Dra I LacZ gene was excised from pCMV-beta and Asc I linkers were ligated to the blunt-ended fragment. This LacZ/Asc I fragment was cloned into p1.1c between Bss HII sites, to give p1.1cADHLacZ, that has the LacZ gene driven by the CMV promoter.

6. A 4387 bp Not I DNA fragment was excised from p1.1cADHLacZ, that has the LacZ gene driven by the CMV promoter. This fragment was inserted between the Not I sites of pWee1909, after removing a 1314bp "CMV promoter/hGH intron" expression cassette. The resulting construct, pW1909ADHLacZ, has the β-galactosidase gene under the control of the CMV promoter and bounded by ITRs. The backbone of the plasmid carries the "rep" and "cap" genes providing AAV helper functions and the β-lactamase (ampicillin) gene confers antibiotic resistance.

7. A 4772 bp Sse I DNA fragment containing a "CMV/LacZ" cassette was excised from pW1909ADHLacZ and inserted into the Sse I site of pUC19, to give Pre-pVLacZ. This construct still contains approximately 50 bp of remnant 5' and 3' pSUB201 sequences internal to each ITR.

8. The remnant pSUB201 sequences were removed by excising a 2912 bp Msc I "pUC/ΔITR" DNA fragment from Pre-pVLacZ, that also removes approximately 35 bp of the "D" region of each ITR. A synthetic linker "145NA/NB" (5'-CCAACTCCATCACTAGGGGTTCCTGCGGCC-3') (SEQ ID NO:6) containing an Msc I restriction site, the ITR "D" region and a Not I site was used to clone in a 4384 bp Not I fragment from pW1909ADHLacZ, that has the "CMV/LacZ" expression cassette. The resulting plasmid pVLacZ, is has the β-galactosidase gene under the control of an alcohol dehydrogenase enhancer sequence and the CMV promoter, all bounded by AAV ITRs.

9. pVLacZ was further modified by removing LacZ elements and polylinker sequence outside of the ITR bound LacZ expression cassette as follows. A 534 bp Ehe I/Afl III LacZ/polylinker sequence was excised from pUC119, the ends were blunted using Klenow DNA polymerase and the plasmid was ligated to a Sse I linker (5'-CCTGCAGG-3') (SEQ ID NO:7), to produce pUC119/SseI. The "AAVLacZ" DNA sequence was removed from pVLacZ by cutting out a 4666 bp Sse I fragment. This SseI fragment was cloned into the Sse I site of pUC119/SseI to generate pVmLacZ. pVmLacZ has the CMV promoter/ADH enhancer/β-galactosidase gene bounded by AAV ITRs in a pUC119-derived backbone that confers ampicillin resistance and has a high copy number origin of replication.

II. Triple Transfection Procedure

The various mutated AAV helper function vectors (described above), the accessory function vector pLadeno5 (described in U.S. Pat. No. 6,004,797, incorporated herein by reference in its entirety), and the rAAV2-lacZ vector, pVmLacZ (described above) were used to produce recombinant virions.

Briefly, human embryonic kidney cells type 293 (American Type Culture Collection, catalog number CRL-1573) were seeded in 10 cm tissue culture-treated sterile dishes at a density of $3\times10^6$ cells per dish in 10 mL of cell culture medium consisting of Dulbeco's modified Eagle's medium supplemented with 10% fetal calf serum and incubated in a humidified environment at 37° C. in 5% $CO_2$. After overnight incubation, 293 cells were approximately eighty-percent confluent. The 293 cells were then transfected with DNA by the calcium phosphate precipitate method, a transfection method well known in the art. 10 μg of each vector (mutated pHLP19, pLadeno5, and pVm lacZ.) were added to a 3-mL sterile, polystyrene snap cap tube using sterile pipette tips. 1.0 mL of 300 mM $CaCl_2$ (JRH grade) was added to each tube and mixed by pipetting up and down. An equal volume of 2×HBS (274 mM NaCl, 10 mM KCl, 42 mM HEPES, 1.4 mM $Na_2PO_4$, 12 mM dextrose, pH 7.05, JRH grade) was added with a 2-mL pipette, and the solution was pipetted up and down three times. The DNA mixture was immediately added to the 293 cells, one drop at a time, evenly throughout the dish. The cells were then incubated in a humidified environment at 37° C. in 5% $CO_2$ for six hours. A granular precipitate was visible in the transfected cell cultures. After six hours, the DNA mixture was removed from the cells, which were then provided with fresh cell culture medium without fetal calf serum and incubated for an additional 72 hours.

After 72 hours, the cells were lysed by 3 cycles of freezing on solid carbon dioxide and thawing in a 37° C. water bath. Such freeze-thaw lysates of the transfected cells were characterized with respect to total capsid synthesis (by Western blotting), DNA packaging (by Q-PCR), heparin binding, in vitro transduction (on HeLa or HepG2 cells plus adenovirus-2 or etoposide), and neutralization by antibodies.

III. Properties of the Mutant Virions

A. Capsid Synthesis Assay

Mutations in proteins can render them unstable and more susceptible than normal to degradation by proteases. In order to determine the level of capsids made by the mutants described herein, western blotting of crude lysates was performed. One microliter of each crude lysate was denatured by incubation in 20 mM Tris, pH 6.8, 0.1% SDS at 80° C. for 5 minutes. Proteins were fractionated by SDS-PAGE using 10% polyacrylamide gels (Invitrogen, Inc., Carlsbad, Calif.) and then detected by western blotting as follows. The proteins were electrophoretically blotted (Xcell II blot module, Invitrogen, Carlsbad, Calif.) onto nylon membranes (Hybond-P, Amersham Biosciences, Piscataway, N.J.). The membranes were probed with an anti-AAV antibody (monoclonal clone B1, Maine Biotechnology Services, Inc. Portland, Me.) at a dilution of 1:20 and then with a sheep anti-mouse antibody coupled to horseradish peroxidase (Amersham Biosciences, Piscataway, N.J.) at a dilution of 1:12000. The B1 antibody-binding proteins were detected using the ECL Plus western blotting detection system (Amersham Biosciences, Piscataway, N.J.). The membranes were exposed to x-ray film Biomax MS, Kodak, Rochester, N.Y.) for 1-5 minutes and the signals were quantified using an AlphaImager 3300 (Alpha Innotech Corp., San Leandro, Calif.)

B. DNA Packaging Assay.

Quantitative polymerase chain reaction (Q-PCR) was used to assess DNA packaging by AAV-2 virions with mutant capsids. In this procedure the crude lysate was digested with DNAse I prior to PCR amplification to remove any plasmid (used in transfection) that might result in a false positive signal. The crude lysates were diluted 100 fold (5 μl crude lysate plus 495 μl buffer) in 10 mM Tris, pH 8.0, 10 μg/ml yeast tRNA. An aliquot of the dilution (10 μl) was digested with 10 units DNAse I (Roche Molecular Biochemicals, Indianapolis, Ind.) in 25 mM Tris, pH 8.0, 1 mM $MgCl_2$ at 37° C. for 60 minutes in a final volume of 50 μl. The DNAse I was inactivated by heating at 95° C. for 30 minutes. One microliter (20 μg) of Proteinase K (Roche Molecular Biochemicals, Indianapolis, Ind.) was added and incubated 55° C. for 30 minutes. The Proteinase K was inactivated by heating at 95° C. for 20 minutes. At this point, the sample was diluted in 10 mM Tris, pH 8.0, 10 μg/ml yeast tRNA if necessary. Ten microliters of DNAse 1 and proteinase K-treated sample was added to 40 μl Q-PCR master mix, which consisted of:

4 μl $H_2O$

5 μl 9 μM lac Z primer #LZ-1883F (5'-TGCCACTCGCTTT AATGAT-3', (SEQ ID NO:8) Operon, Inc., Alameda, CA)

5 μl 9 μM lac Z primer #LZ-1948R (5'-TCGCCGCACATCT GAACTT-3', (SEQ ID NO:9) Operon, Inc., Alameda, CA)

1 μl 10 μM lacZ probe # LZ-1906T (5'-6FAM-AGCCTCCAGTACAGCGCGGCTGA-TAMRA-3', (SEQ ID NO:10) Applied Biosystems, Inc. Foster City, CA)

25 μl TaqMan Universal PCR Master Mix (Applied Biosystems, Inc. Foster City, CA)

Q-PCR amplification was done using an Applied Biosystems model 7000 Sequence Detection System according to the following program. There were two initial incubations at 50° C. for 2 minutes and 95° C. for 10 minutes to activate Taq polymerase and denature the DNA template, respectively. Then the DNA was amplified by incubation at 95° C. for 15 sec, then 60° C. for 60 seconds for 40 cycles. A standard curve was constructed using 4-fold dilutions of linearized pVm lac Z ranging from a copy number of 61 to 1,000,000. The copy number of packaged rAAV-lacZ genomes in each sample was calculated from the $C_t$ values obtained from the Q-PCR using the Applied Biosystems Prism 7000 Sequence Detection System version 1.0 software.

C. Heparin-Binding Assay

Heparin binding of viruses in crude lysates was performed as follows. Twenty microliters of crude cell lysate containing AAV-2 virions with wild-type or mutant capsids were mixed with 25 μl of a 50% slurry of heparin beads. The heparin beads (Ceramic Hyper-DM Hydrogel-Heparin, Biosepra, Cergy-Saint-Christophe, France) were 80 μm in diameter and had 1000 Å pores to allow AAV (which is ~300 Å in diamater) access to the heparin. The beads were washed thoroughly in phosphate-buffered saline prior to use. The beads and virions were incubated at 37° C. for 60 minutes. The beads were pelleted. The supernatant containing unbound virions was saved. The beads were washed 2 times with 500 μl PBS. The supernatants were combined and unbound capsid proteins were precipitated with trichloroacetic acid at a final concentration of 10%. Precipitated proteins were denatured by incubation in 20 mM Tris, pH 6.8, 0.1% SDS at 80° C. for 5 minutes. Virions bound to heparin beads were released by incubation of the beads in 20 mM Tris, pH 6.8, 0.1% SDS at 80° C. for 5 minutes. All protein samples prepared in this manner were fractionated by molecular weight by SDS-PAGE using 10% polyacrylamide gels (Invitrogen, Inc., Carlsbad, Calif.) and then detected by western blotting as follows. The proteins were electrophoretically blotted onto nylon membranes (Hybond-P, Amersham Biosciences, Piscataway, N.J.). The membranes were probes with an anti-AAV antibody (monoclonal clone B1, Maine Biotechnology Services, Inc. Portland, Me.) at a dilution of 1:20 and then with a sheep anti-mouse antibody coupled to horseradish peroxidase (Amersham Biosciences, Piscataway, N.J.) at a dilution of 1:12000. The B1 antibody-binding proteins were detected using the ECL Plus western blotting detection system (Amersham Biosciences, Piscataway, N.J.). The membranes were exposed to x-ray film Biomax MS, Kodak, Rochester, N.Y.) for 1-5 minutes and the signals were quantitated using an AlphaImager 3300 (Alpha Innotech Corp., San Leandro, Calif.)

D. In vitro Transduction Assay.

HeLa cells (American Type Culture Collection, catalog # CCL-2) were plated in 24-well dishes at 5e4 cells per well. Cells were grown for 24 hr in Dulbecco's Modified Eagle Medium (DMEM) (Gibco) supplemented with 10% fetal bovine serum (Gibco) and penicillin-streptomycin (Gibco) at 37° C. Ten-fold dilutions of crude lysates containing the control wild type and mutant viruses were made in DME/10% FBS. The virus dilutions were added to the cells along with wild type adenovirus-5 (American Type Culture Collection, catalog # VR-5). The amount of adenovirus used was 0.1 μl per well, which was titered previously and shown to maximally stimulate rAAV-2 lac Z transduction of HeLa cells. After 24 hours at 37° C. the cells were fixed using 2% formaldehyde and 0.2% glutaraldehyde and stained for β-galactosidase activity using 1 mg/ml (2.5 mM) 5-bromo-4-chloro-3-indolyl β-D galactopyranoside in PBS, 2 mM $MgCl_2$, 5 mM potassium ferricyanide, 5 mM potassium ferrocyanide, pH 7.2. After another 24 hours, the number of blue cells in four random microscopic fields were counted and averaged for each well. Instead of using HeLa cells and adenovirus-5, HepG2 cells and 20 μM etoposide could also be used and similar results were obtained.

E. Antibody and Serum Neutralization Assays.

Hep G2 cells (American Type Culture Collection, catalog # HB-8065) were plated in 24-well dishes at 1.5e5 cells per well. Cells were grown for 24 hr in Minimum Essential Medium (Eagle's) (KMEM) (ATCC) supplemented with 10% fetal bovine serum and penicillin-streptomycin at 37° C. Two-fold dilutions of the A20 antibody (Maine Biotechnology, Portland, Me.) were made using PBS. Wild-type and mutant virus was diluted by mixing 1 microliter of crude lysate of the viral preparation with 15 microliters of KMEM/0.1% Bovine Serum Albumin (BSA). Samples of KMEM/0.1% BSA and PBS were included as a negative controls. A total of 16 μL of A20 dilution was mixed with 16 μL of virus and incubated at 37° C. for one hour. Ten microliters of virus/A20 mixture was added to each of three wells of cells. After one hour incubation at 37° C., etoposide (20 mM stock solution in dimethyl sulfoxide, Calbiochem) was added to each well at a final concentration of 20 μM. After 24 hours the cells were fixed using 2% formaldehyde and 0.2% glutaraldehyde and stained for β-galactosidase activity using 1 mg/ml (2.5 mM) 5-bromo-4-chloro-3-indolyl β-D galactopyranoside in PBS, 2 mM $MgCl_2$, 5 mM potassium ferricyanide, 5 mM potassium ferrocyanide, pH 7.2. After another 24 hours, the number of blue cells in four random microscopic fields were counted and averaged for each well. The neutralizing titer of an antibody is defined as the dilution of antibody at which there is a 50% reduction in the number of viral transduction events (i.e., blue cells) compared to transduction in the absence of antibody.

Neutralization of mutants by human sera collected from hemophiliacs or to purified human IgG from >10,000 donors (Panglobulin, ZLB Bioplasma AG, Berne, Switzerland) was assayed in the same manner. For purified human IgG, a concentration of 10 mg/ml was considered to be equivalent to undiluted sera since the normal concentration of IgG in human sera varies from 5-13 mg/ml.

F. ELISAs.

(a) A20 ELISA:

An ELISA kit (American Research Products, Belmont, Mass.) that uses a monoclonal antibody (A20) to capture and detect AAV-2 was used to quantitate particle numbers. The kit was used according to the manufacturer's instructions. Optical density was measured in a Spectramax 340PC plate reader (Molecular Devices, Sunnyvale, Calif.) at 450 nm wavelength. The concentration of virus needed to result in a half maximal optical density reading was calculated and used to compare the results from different samples.

(b) IgG/A20 ELISA:

Microtiter plates (96-well EIA/RIA flat bottom, high-binding polystyrene, Costar, Corning, N.Y.) were coated using 100 μl (10 μg) Panglobulin in 0.1 M sodium bicarbonate buffer, pH 9.2 for 16 hours at 20° C. Plates were blocked with 200 μl PBS, 1% BSA, 0.05% Tween-20 for 1 hour at 20° C. Increasing amounts of CsCl gradient-purified native or mutant AAV-2 ranging from $3.0^8$ to $1.0^{10}$ vector genomes per well were added and incubated for 16 hours at 20° C. Unbound virus was washed off using 3-200 μl aliquots of PBS, 0.1% Tween-20 buffer. A20-biotin from the AAV-2 ELISA kit was diluted 1:50, 100 μl was added per well, and incubated for 1 hours at 37° C. Unbound A20-biotin was washed off using 3 200 μl aliquots of PBS, 0.1% Tween-20 buffer. Then streptavidin coupled to horseradish peroxidase was diluted 1:20 and incubated for 1 hours at 37° C. Unbound streptavidin-HRP was washed off using 3 200 μl aliquots of PBS, 0.1% Tween-20 buffer. Horseradish peroxidase substrates (Immunopure TMB substrate kit Pierce, Rockford, Ill.) were added and incubated for 15 min at 20° C. The reaction was stopped with 100 μl 2M sulfuric acid and optical density was measured in a Spectramax 340PC plate reader (Molecular Devices, Sunnyvale, Calif.) at 450 nm wavelength. The concentration of virus needed to result in a half maximal optical density reading was calculated and used to compare the results from different samples.

(c) IgG ELISA:

Microtiter plates (96-well EIA/RIA flat bottom, high-binding polystyrene, Costar, Corning, N.Y.) were coated with increasing amounts of CsCl gradient-purified native or mutant AAV-2 ranging from $3.0^8$ to $1.0^{10}$ vector genomes per well for 16 hours at 20° C. in 0.1 M sodium bicarbonate buffer, pH 9.2 for 16 hours at 20° C. Plates were blocked with 200 μl PBS, 1% BSA, 0.05% Tween-20 for 1 hour at 20° C. Unbound virus was washed off using 3-200 μl aliquots of PBS, 0.1% Tween-20 buffer. Panglobulin was added and incubated for 1 hour at 37° C. Unbound Panglobulin was washed off using 3-200 μl aliquots of PBS, 0.1% Tween-20 buffer. Then donkey, anti-human IgG coupled to horseradish peroxidase (Amersham Biosciences, Piscataway, N.J.) was added and incubated for 1 hours at 37° C. Unbound secondary antibody was washed off using 3-200 μl aliquots of PBS, 0.1% Tween-20 buffer. Horseradish peroxidase substrates (Immunopure TMB substrate kit Pierce, Rockford, Ill.) were added and incubated for 15 min at 20° C. The reaction was stopped with 100 μl of 2M sulfuric acid and optical density was measured in a Spectramax 340PC plate reader (Molecular Devices, Sunnyvale, Calif.) at 450 nm wavelength. The concentration of virus needed to result in a half maximal optical density reading was calculated and used to compare the results from different samples.

The DNA packaging, heparin-binding, and transduction properties of mutants described here are summarized in Table 1. The antibody neutralization properties of some of the mutants described here are summarized in Tables 2 and 3.

TABLE 1

Properties of AAV-2 capsid mutants.

| Mutant[1] | Capsid synthesis[2] | DNA packaging[3] | Heparin binding[4] | Transduction[5] |
|---|---|---|---|---|
| wild type | 100 | 100 | >95 | 100 |
| Q126A | 65 | 67 | >95 | 55 |
| Q126A/S127L | 78 | 4 | >95 | 0.02 |
| S127A | 68 | 98 | >95 | 53 |
| G128D | 100 | 674 | >95 | 0.02 |
| Δ128ins1 | 77 | 777 | >95 | 0.02 |
| S130A/N131A | 55 | nt | >95 | 0.02 |
| N131A | 67 | 563 | >95 | 0.005 |
| D132A | 75 | 23 | >95 | 0.04 |
| H134A | 44 | 540 | >95 | 2 |
| Q188A | 55 | 16 | >95 | 0.36 |
| D190A | 60 | 51 | >95 | 95 |
| G191S | 108 | 18 | >95 | 22 |
| T193A | 38 | 7 | >95 | 6 |
| S247A | 18 | 83 | >95 | 24 |
| Q248A | 60 | 374 | >95 | 280 |
| S315A | 101 | 122 | >95 | 232 |
| T317A | 101 | 111 | >95 | 208 |
| T318A | 100 | 132 | >95 | 224 |
| Q320A | 97 | 89 | >95 | 68 |
| R322A | 100 | 560 | >95 | 106 |
| G329R | 43 | 21 | >95 | 0.24 |
| S331A | 168 | 80 | >95 | 158 |
| D332A | 85 | 474 | >95 | 8 |
| R334A | 169 | 601 | >95 | 79 |
| D335A | 136 | 127 | >95 | 38 |
| T354A | 132 | 301 | >95 | 93 |
| S355A | 69 | 353 | >95 | 38 |
| S355T | 110 | 183 | >95 | 88 |
| A356R | 85 | 18 | 25 | 13 |
| D357A | 39 | 166 | >95 | 4 |
| N359A | 24 | 365 | >95 | 89 |
| N360A | 8 | 246 | >95 | 33 |
| N360H/S361A | 145 | 472 | >95 | 38 |
| S361A | 81 | 608 | >95 | 89 |
| S361A/N358K | 59 | nt | >95 | 0.45 |
| S361A/S494P | 87 | nt | 90 | 0.02 |
| S361A/R592K | 108 | nt | 90 | 180 |
| E362A | 149 | 56 | >95 | 12 |
| W365A | 195 | 60 | >95 | 4 |
| T366A | 151 | 8 | >95 | 0.01 |
| G375P | 221 | 82 | 50 | 0.01 |
| D377A | 211 | 80 | >95 | 20 |
| K390A | 155 | 267 | >95 | 189 |
| D392A | 98 | 48 | >95 | 0.01 |
| E393A | 54 | 81 | >95 | 2 |
| E394A | 29 | 108 | >95 | 22 |
| K395A | 34 | 2046 | >95 | 14 |
| F396A | 178 | nt | >95 | 148 |
| K407A | 220 | 112 | >95 | 32 |
| E411A | 90 | 513 | >95 | 20 |
| T413A | 233 | 34 | >95 | 252 |
| E418A | 264 | 74 | >95 | 37 |
| K419A | 81 | 806 | >95 | 160 |
| E437A | 239 | 94 | >95 | 24 |
| Q438A | 28 | 101 | >95 | 92 |
| G449A | 104 | 106 | >95 | 196 |
| N450A | 217 | 144 | >95 | 207 |
| Q452A | 313 | 533 | >95 | 473 |
| N568A | 439 | 412 | >95 | 536 |
| K569A | 831 | 333 | >95 | 20 |
| V571A | 98 | 251 | >95 | 142 |

[1]Mutants are named as follows: The first letter is the amino acid in wild type AAV-2 capsid, the number is the position in capsid that was mutated (numbered according to the AAV-2 VP2 sequence), and the last letter is the mutant amino acid. Δ128ins1 has amino acid 128 deleted and the sequence DASNDNLSSQSD inserted in its place.

[2]As determined by western blotting of crude lysates. Expressed as a percentage of wild type capsid synthesis.

[3]DNAse-resistant, vector-specific DNA, quantified by Q-PCR and expressed as a percentage of wild type, which was normalized to 100%. Average of 2 experiments, each done in triplicate. nt, not tested.

[3]Heparin-binding, expressed as a percentage of wild type. Single determinations except for wild type, which is an average of three determinations, normalized to 100%.

[4]Transduction on human 293 cells expressed as a percentage of wild type. Average of 2 experiments.

TABLE 2

Antibody neutralization properties of AAV-2 capsid mutants.

| Serum[1] | Mutant | Transduction (% of wt) | blue cells (−serum) | blue cells (+serum) | % Neut. | Fold neutralization resistant |
|---|---|---|---|---|---|---|
| HA2 | wild type | 100 | 13275 | 3 | 99.98 | 1.0 |
| | R334A | 114 | 15102 | 146 | 99.04 | 42.7 |
| | N450A | 89 | 11802 | 14 | 99.88 | 5.2 |
| | wild type | 100 | 25960 | 8 | 99.97 | 1.0 |

TABLE 2-continued

Antibody neutralization properties of AAV-2 capsid mutants.

| Serum[1] | Mutant | Transduction (% of wt) | blue cells (−serum) | blue cells (+serum) | % Neut. | Fold neutralization resistant |
|---|---|---|---|---|---|---|
| | E394A | 6 | 1593 | 6 | 99.64 | 11.2 |
| | T413A | 21 | 5505 | 15 | 99.73 | 8.5 |
| | N360H/S361A | 41 | 10691 | 7 | 99.94 | 2.0 |
| HA151 | wild type | 100 | 11965 | 16 | 99.87 | 1.0 |
| | R334A | 185 | 22125 | 459 | 97.93 | 15.8 |
| | E394A | 16 | 1947 | 14 | 99.27 | 5.6 |
| | V571A | 73 | 8732 | 39 | 99.56 | 3.4 |
| | G449A | 218 | 26137 | 121 | 99.54 | 3.5 |
| | N568A | 122 | 14632 | 36 | 99.75 | 1.9 |
| | N450A | 95 | 11387 | 53 | 99.54 | 3.5 |
| | wild type | 100 | 15989 | 13 | 99.92 | 1.0 |
| | E411A | 18 | 2876 | 13 | 99.54 | 5.7 |
| | N360H/S361A | 100 | 15989 | 21 | 99.87 | 1.6 |
| HA165 | wild type | 100 | 22833 | 14 | 99.94 | 1.0 |
| | N360A | 16 | 3717 | 9 | 99.75 | 4.0 |
| | R334A | 74 | 16872 | 162 | 99.04 | 15.3 |
| | E394A | 11 | 2566 | 2 | 99.91 | 1.4 |
| | N568A | 102 | 23246 | 30 | 99.87 | 2.1 |
| | N450A | 64 | 14514 | 26 | 99.82 | 2.9 |
| | N360H/S361A | 49 | 9558 | 8 | 99.92 | 1.3 |

[1]Mutants were rapidly screened by comparing the number of transduced cells resulting from infection of HepG2 cells by rAAV-2 lac Z with mutant or wild type capsids in the presence or absence of a monoclonal (A20) antibody at a dilution of 1:80 or human polyclonal serum at a dilution of 1:100.

TABLE 3

Antibody titration properties of 4 antibodies against AAV-2 capsid mutants.

| Mutant[3] | Fold decrease in neutralizing titer[1] Antibody[2]: A20 | 151 | 165 | HA2 |
|---|---|---|---|---|
| wild type | 1.0 | 1.0 | 1.0 | 1.0 |
| Q126A | 2.5 | NR | NR | NR |
| S127A | 57.0 | NR | NR | NR |
| S247A | 2.8 | NR | NR | NR |
| Q248A | 5.7 | NR | NR | NR |
| R334A | NR | 3.6 | 2.4 | 2.0 |
| N360H/S361A | NR | 2.2 | 1.2 | 1.3 |
| E394A | NR | 2.1 | 1.2 | 1.9 |
| N450A | NR | 1.7 | 1.6 | 1.3 |
| Predicted multiplicative resistance: | | | | |
| | 2415 | 29 | 6 | 11 |

[1]Titers were determined by using 2-fold dilutions of monoclonal antibody and fitting the data to a four-parameter logistic curve using Sigma Plot graphing software. Values reported in the table are the fold decrease in titer of the mutant relative to wild type capsid. NR, not resistant to neutralization by indicated antibody.

[2]A20 is a protein A-purified anti-AAV-2 mouse monoclonal antibody. Sera 151, 165, and HA2 are 3 unpurified human sera.

[3]Mutants are named as follows: The first letter is the amino acid in wild type AAV-2 capsid, the number is the position in capsid that was mutated (numbered according to the AAV-2 VP2 sequence), and the last letter is the mutant amino acid. Δ128ins1 has amino acid 128 deleted and the sequence DASNDNLSSQSD (SEQ ID NO:11) inserted in its place.

As can be seen, by changing single amino acids on the surface of AAV-2 32 mutants out of 61 were identified that had nearly normal properties with respect to capsid synthesis, DNA packaging, heparin binding, and transduction of cells in vitro. Ten mutants were more resistant to neutralization by antibodies.

The mutants made capsid protein at a level between 5-fold lower to 8-fold higher than wild type. They packaged DNA at a level between 25-fold lower to 20-fold higher than wild type. With regard to transduction, 28 of the mutants transduced at least 50% as well as wild type, 16 transduced 10-50% of wild type, 6 transduced 1-10% of wild type, and 11 transduced less than 1% of wild type (Table 1). There were no significant differences in transduction of human cervical carcinoma-derived HeLa cells or human liver-derived Hep G2 cells, or when either adenovirus or etoposide was used to enhance transduction. Several mutants reproducibly had up to 5-fold more transducing activity than wild type (Table 1).

Figure 4:
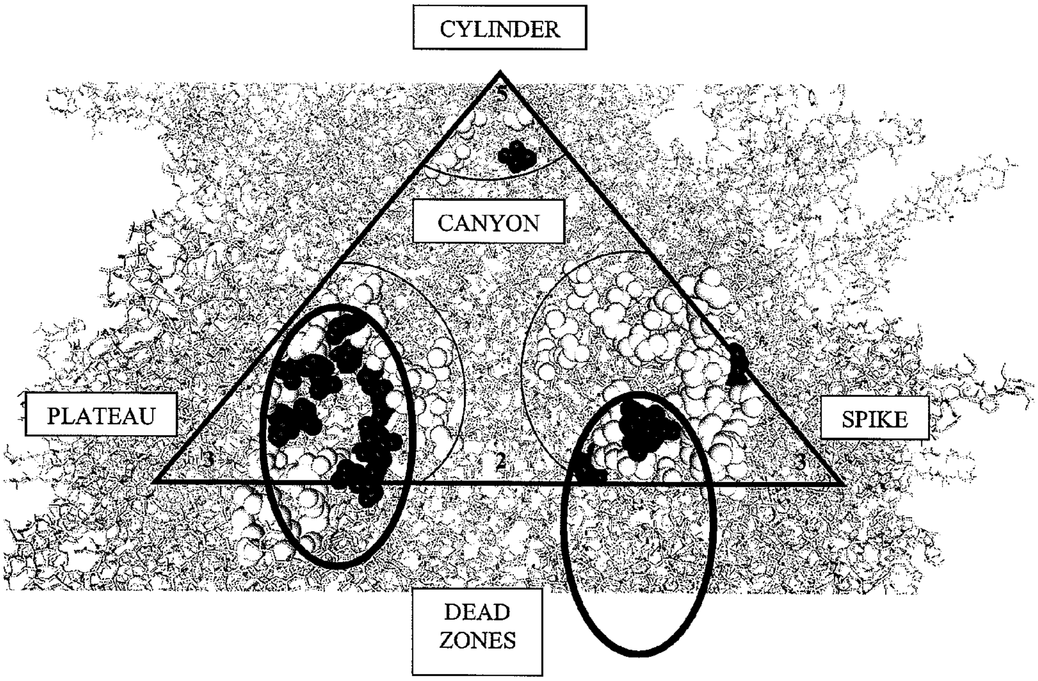
FIG. 4 indicates the location of mutations that have >10-fold effect on in vitro transduction. Mutations located at black space-filling amino acids, <10% wild type transduction. The numbers 2, 3 and 5 represent 2-, 3- and 5-fold axes of symmetry, respectively. The approximate boundaries of two dead zones spanning the 2-fold axis of symmetry is indicated.
Figure 5:
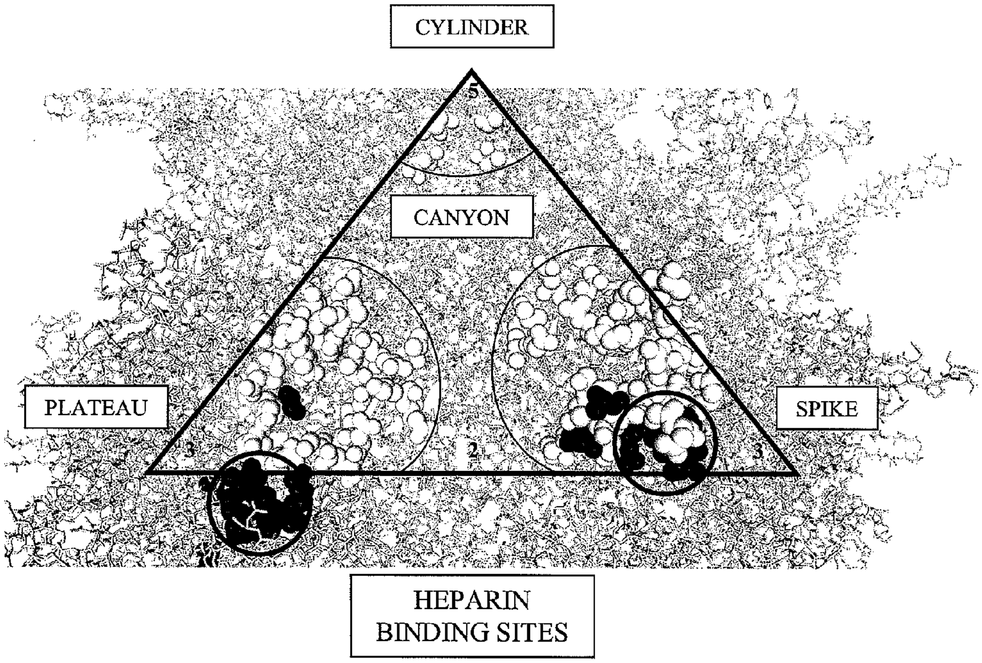
FIG. 5 illustrates the location of some of the AAV-2 capsid mutants defective in heparin binding. Black amino acids designate heparin-defective mutants identified herein. Black amino acids illustrated as space-filling models (347, 350, 356, 375, 395, 448, 451) are on the surface. Grey amino acids illustrated as space-filling models (495, 592) are just under the surface. The numbers 2, 3 and 5 represent the 2-, 3- and 5-fold axes of symmetry, respectively. Mutants that have more than a 100-fold effect on heparin binding are enclosed in circles.

Most of the mutants with <1% transduction activity were clustered in a single area, on one side of the (proposed) heparin-binding site (Table 1, compare FIG. 4 with FIG. 5). Without being bound by a particular theory, the mutations cover an area that may be a protein-binding site. The mutant that was most defective for transduction was N131A. A function for N131 has not been described, but it is conserved in 40 out of 42 known AAV subtypes.

Four mutations affected heparin binding more noticeably than the others (A356R, G375A, S361A/S494P, S361A/R592K). Each of these is near R347, R350, K390, R448 and R451, which have been previously identified as amino acids that are important for heparin binding (FIG. 5).

Figure 6:
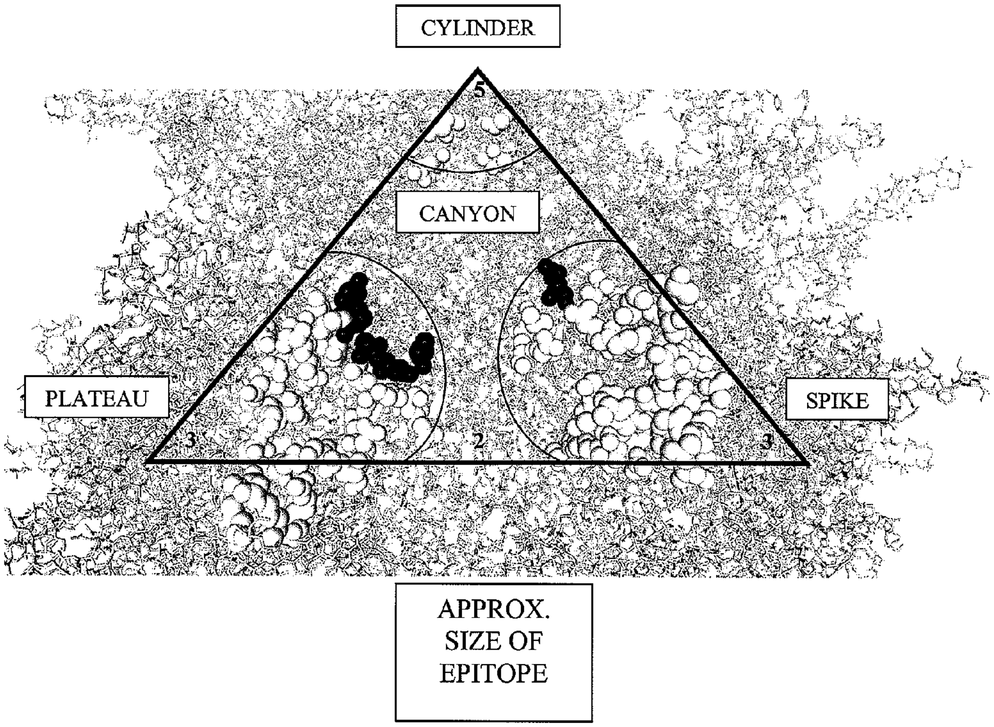
FIG. 6 illustrates the location of some of the amino acids (black space-filling model) on the surface of the AAV-2 capsid that confer resistance to neutralization by a mouse monoclonal antibody when they are individually mutated. The rectangular box represents the approximate size of an antibody binding site (25 Å×35 Å). The numbers 2, 3, and 5 represent the 2-, 3- and 5-fold axes of symmetry, respectively.
Figure 8:
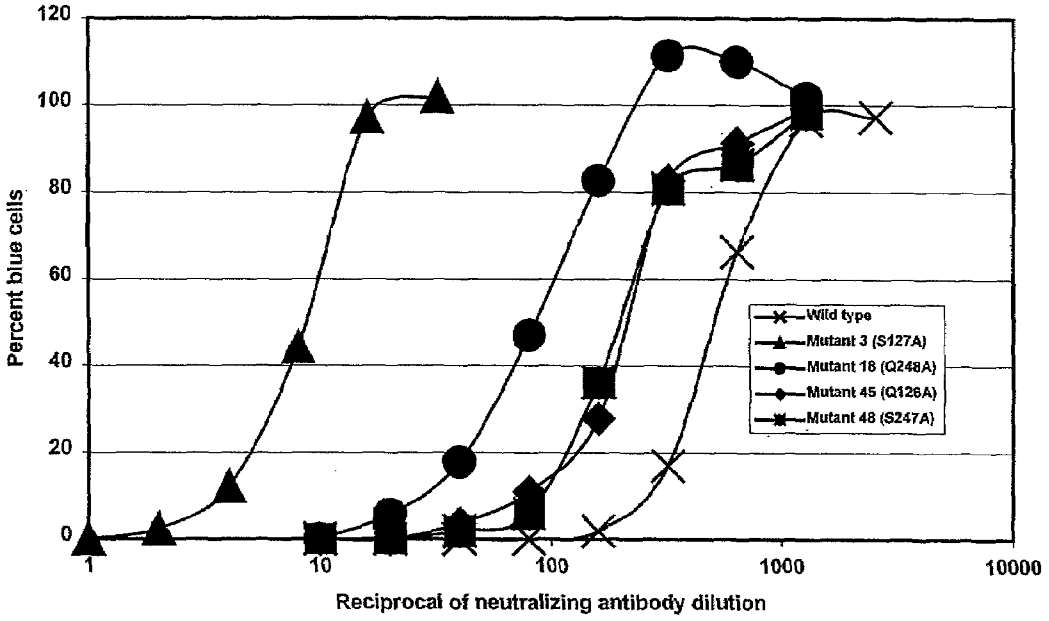
FIG. 8 shows mouse monoclonal antibody titration properties of four AAV-2 capsid mutants compared to AAV-2 with a wild-type capsid.

Forty five of the mutants (Q126A, S127A, D190A, G191S, S247A, Q248A, S315A, T317A, T318A, Q320A, R322A, S331A, D332A, R334A, D335A, T354A, S355A, S355T, A356R, D357A, N359A, N360A, N360H/S361A, S361A, S361A/R592K, E362A, D377A, K390A, E393A, E394A, K395A, F396A, K407A, E411A, T413A, E418A, K419A, E437A, Q438A, G449A, N450A, Q452A, N568A, K569A, V571A) with more than approximately 10% of the transduction activity of wild-type AAV-2 capsid were screened for neutralization by the murine A20 monoclonal antibody. Four mutants (Q126A, S127A, S247A, Q248A) were significantly more resistant to neutralization by A20 than was AAV2 with a wild type capsid (see Table 3). The titer of these mutants (Q126A, S127A, S247A, Q248A) was 1:203, 1:9, 1:180 and 1:89, respectively (FIG. 8), which is 2.5, 57, 2.8, and 5.7-fold greater than the neutralizing titer of the A20 monoclonal antibody against wild type AAV-2 capsid (1:509). These 4 mutants are located immediately adjacent to each other on the surface of the AAV-2 capsid (FIG. 6).

Three (Q126A, S 127A, Q248A) of the four mutations that reduce neutralization by A20 were essentially normal with regard to capsid synthesis, DNA packaging, heparin binding, and transduction. Capsid synthesis and transduction by mutant S247A was 4- to 5-fold less than wild-type AAV-2 capsid. Thus it is possible to have a virus that is normal in several important properties but has increased resistance to antibody neutralization.

The mutant rAAV virions Q126A, S127A, S247A, Q248A yielded an unexpected 2.5- to 57-fold resistance to neutralizing antibody while maintaining transduction efficiency in 2 different human cell lines (HeLa and HepG2). These four amino acids are immediately adjacent to each other on the surface of AAV-2 (FIG. 6). Furthermore, they are in an area that had been previously implicated in binding the A20 antibody, based on peptide competition and insertional mutagenesis experiments. Based on these observations it is possible the A20 antibody blocks one or more functions necessary for AAV-2 to transduce cells. In a previous study it has been shown that A20 does not block binding of AAV-2 to heparin (Wobus et al (2000) *J. Virol.* 74:9281-93). The results reported here support this data since mutations that affect heparin binding are located far from mutations that affect A20 binding. Although A20 does not block heparin binding, it does prevent AAV-2 from entering cells. It is possible that A20 does not interfere with binding to a "docking receptor" such as heparin, but instead interferes with binding of AAV-2 to an "entry receptor". Two proteins have been described that are required for AAV-2 transduction which may be entry receptors: the basic fibroblast growth factor receptor (bFGF$^R$) and $\alpha_v\beta_5$ integrin. The areas on AAV-2 that these receptors may bind have not been identified. It is possible $\alpha_v\beta_5$ integrin, bFGF$^R$, or both may bind to the localized area described herein that has a high concentration of mutants that are significantly defective in transduction (<1% of normal). Note that the area that is most defective for transduction is located adjacent to the mutants that affect A20 binding.

The same 45 mutants (Q126A, S 127A, D190A, G191 S, S247A, Q248A, S315A, T317A, T318A, Q320A, R322A, S331A, D332A, R334A, D335A, T354A, S355A, S355T, A356R, D357A, N359A, N360A, N360H/S361A, S361A, S361A/R592K, E362A, D377A, K390A, E393A, E394A, K395A, F396A, K407A, E411 A, T413A, E418A, K419A, E437A, Q438A, G449A, N450A, Q452A, N568A, K569A, V571A) with more than approximately 10% of the transduction activity of wild type AAV-2 capsid were screened for neutralization by 3 human neutralizing antisera. Four mutants (R334A, N360H/S361A, E394A, N450A) were identified in an initial screen that were more resistant to neutralization by all three human antisera, than was AAV2 with a wild-type capsid (see Table 2). The titer of antisera when tested on these mutants ranged from 1.3 to 3.6-fold greater than the neutralizing titer of the three human antisera against wild type AAV-2 capsid (Table 3). Six other mutants (N360A, E411 A, T413A, G449A, N568A, V571A) had increased levels of resistance to neutralization by 1 or 2 of the 3 sera tested (Table 2).

Figure 7:
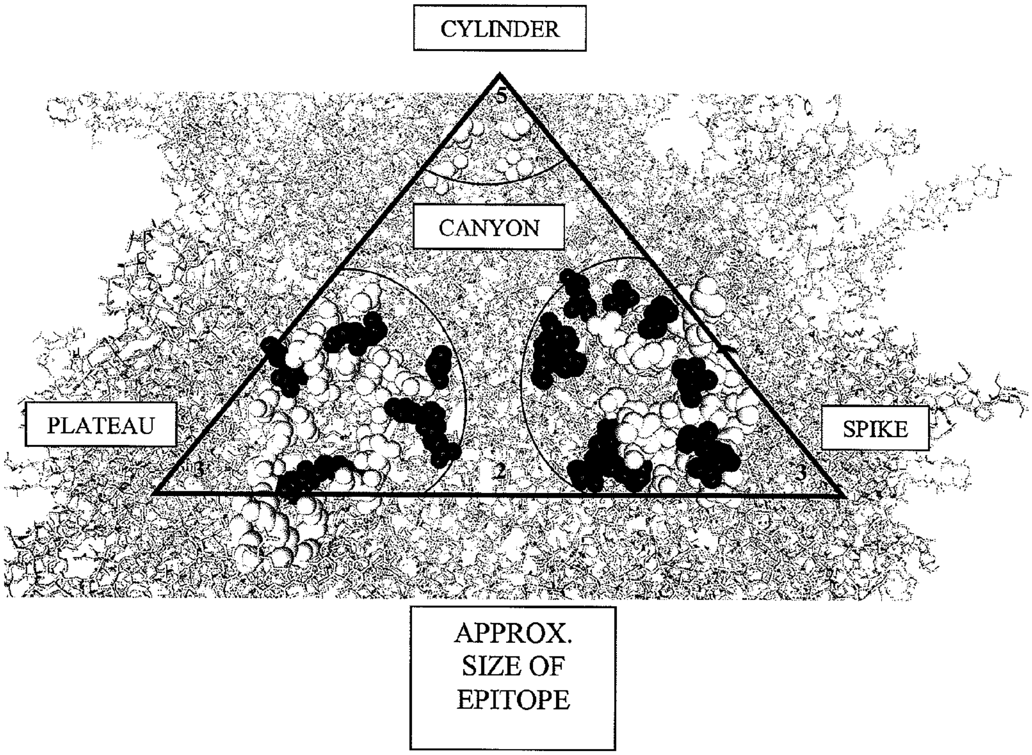
FIG. 7 illustrates the location of some of the amino acids (black space-filling model) on the surface of the AAV-2 capsid that confer resistance to neutralization by multiple human antisera. The rectangular box represents the approximate size of an antibody binding site (25 Å×35 Å). The numbers 2, 3, and 5 represent the 2-, 3- and 5-fold axes of symmetry, respectively.

The location of the mutations that confer antibody neutralization resistance is informative. First, mutants that confer resistance to a mouse monoclonal antibody are located immediately adjacent to each other on the surface of the AAV-2 capsid whereas those that confer resistance to human antisera are spread over a larger area (FIG. 7). This suggests the human antisera are polyclonal, which is not surprising. Second, both sets of mutants are located on the plateau and spike but not on the cylinder, even though the cylinder would be readily accessible to antibody binding. Third, mutations that affect neutralization are near areas important for AAV function. Several mutants that affect neutralization by human antisera (at positions 360, 394, 449, 450) are located within 2 amino acids of the heparin binding site, which is likely to be a functionally important target for binding by neutralizing antibodies. Other mutants (at positions 126, 127, 247, 248, 334, 568, 571) are located at the periphery of the large region on the plateau (dead zone) that contains most of the mutants that had <10% of wild type transduction activity (FIG. 4). Like the heparin-binding site, this area presumably has an important function and is likely to be a functionally important target for binding by neutralizing antibodies.

When multiple mutations that confer resistance to antibody neutralization are combined the cumulative resistance to antibody neutralization is often multiplicative, especially when the individual mutations result in low levels of resistance. Therefore, it is likely that if the mutants described here are combined into one capsid, those capsids could be 5-fold to over 1000-fold more resistant to neutralization compared to a wild-type capsid (Table 3). Dilutions of A20 greater than 1:1000 neutralize <3% of wild-type AAV-2. Thus a mutant with a combination of the 4 single amino acids that provide some resistance to neutralization by A20 could be almost completely resistant to neutralization even by undiluted A20 antisera.

Figure 3:
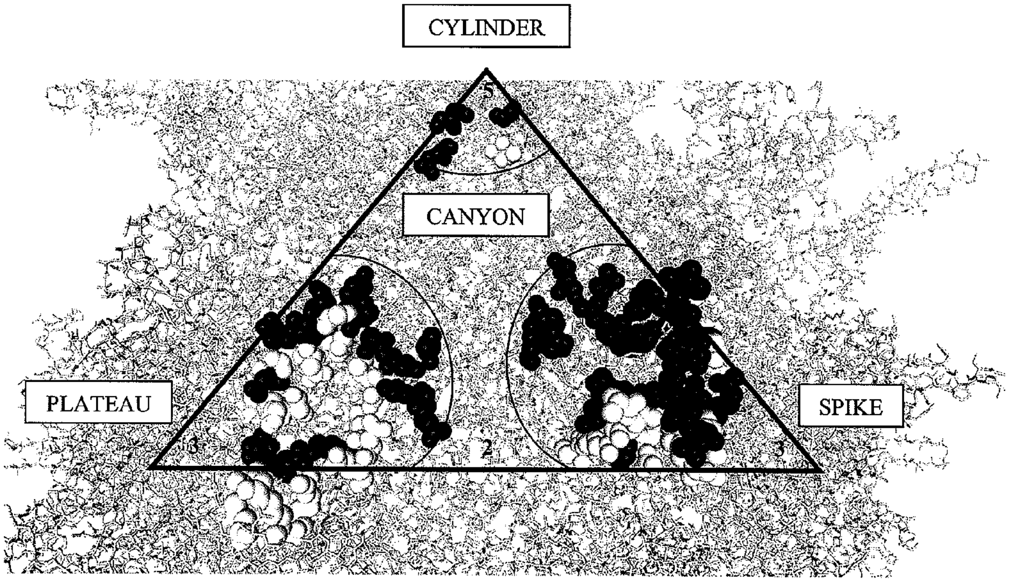
FIG. 3 indicates the location of mutations that have <10-fold effect on in vitro transduction. Mutations located at black space-filling amino acids, <10% wild type transduction. The numbers 2, 3 and 5 represent 2-, 3- and 5-fold axes of symmetry, respectively.

Although mutants with <10% wild type transduction activity may also be resistant to antibody neutralization they were not tested because the neutralization assay, as described here, works best when used to assay mutants that have >~10% of wild-type transduction activity (FIG. 3). This is because it is desirable to be able to detect neutralization over a wide range of antibody concentrations so that a titer can be accurately calculated. However, mutants with <10% wild-type transduction activity could still be tested for their ability to bind neutralizing antibody using a modification of the assay described here in which a transduction defective mutant would be used as a competitor. For example a wild-type "reporter" rAAV-2 lacZ virus could be mixed with a transduction defective "competititor" AAV-2 that lacks any genome ("empty virus") or with an AAV-2 virus that has packaged another gene (e.g., green fluorescent protein). If a "competititor" AAV-2 protects a reporter AAV-2 from neutralization then the "competititor" capsid should be able to bind neutralizing antibody and thus would not be resistant to neutralization. If a "competititor" AAV-2 does not protect a reporter AAV-2 from neutralization then the "competititor" capsid may not be able to bind neutralizing antibody and thus could be resistant to neutralization as long as it was shown to make a normal amount of capsid. In this way even mutants that are transduction defective but resistant to antibody neutralization could be identified. In order to make such mutants useful as vehicles for delivering genes in the presence of neutralizing antibodies, it would be desirable to find an amino acid substitution other than alanine that would restore normal transducing activity, but still retain decreased susceptibility to neutralization.

66 more mutants were made and tested using the protocols described above. The DNA packaging, heparin-binding, and transduction properties of the additional mutants are summarized in Table 4.

TABLE 4

Properties of Additional AAV-2 capsid mutants.

| Mutant | Capsid synthesis[2] | DNA packaging | Heparin binding | Transduction |
|---|---|---|---|---|
| G128A | + | 207 | >95% | 1.5 |
| S130A | + | 172 | >95% | 92 |
| S130T | + | 232 | >95% | 1164 |
| N131Q | + | 113 | >95% | 0.01 |
| D132E | + | 202 | >95% | 4 |
| D132N | + | 188 | >95% | 75 |
| N133A | + | 187 | >95% | 418 |
| H134F | + | 180 | >95% | 0.2 |
| H134Q | + | 340 | >95% | 17 |
| H134T | + | 102 | >95% | 0.4 |
| N245A | + | 145 | >95% | 1.8 |
| G246A | + | 353 | >95% | 0.6 |
| R350K | + | 52 | >95% | 16 |
| D357E | + | 222 | >95% | 427 |
| D357N | + | 157 | >95% | 28 |
| D357Q | + | 204 | >95% | 1.6 |
| N360H | + | 129 | >95% | 37 |
| N360K | + | 59 | >95% | 0.06 |
| W365F | + | 253 | >95% | 6 |
| T366S | + | 251 | >95% | 18 |
| H372F | + | 130 | >95% | 4.1 |
| H372K | + | 154 | >95% | 72 |
| H372N | + | 221 | >95% | 122 |
| H372Q | + | 248 | >95% | 73 |
| G375A | + | 55 | >95% | 2.4 |
| D391A | + | 140 | >95% | 1.21 |
| D392E | + | 158 | >95% | 15 |
| D392I | + | 411 | >95% | 0.5 |
| D392N | + | 236 | >95% | 0.2 |
| D392V | + | 247 | >95% | 0.001 |
| E393D | + | 218 | >95% | 80 |
| E393K | + | 123 | >95% | 0.02 |
| E393Q | + | 92 | >95% | 1.2 |
| E394K | + | 190 | >95% | 6.0 |
| E411K | + | 28 | >95% | 4.6 |
| T413K | + | 196 | >95% | 57 |
| R448A | + | 3255 | <1% | 0.3 |
| R448K | + | 768 | >95% | 80 |
| G449K | + | 270 | >95% | 3.1 |
| N450K | + | 281 | >95% | 0.7 |
| R451A | + | 2971 | <1% | 0.07 |
| R451K | + | 10 | >95% | 133 |
| N568K | + | 488 | >95% | 16 |
| V571K | + | 614 | >95% | 40 |
| R334A/N360K | + | 380 | >95% | 0.6 |
| R334A/G449A | + | 87 | >95% | 91 |
| R334A/N450A | + | 738 | >95% | 238 |
| R334A/N568A | + | 150 | >95% | 147 |
| N360K/N450A | + | 166 | >95% | 0.2 |
| E411A/T413A | + | 548 | >95% | 74 |
| G449A/N450A | + | 94 | >95% | 111 |
| G449A/N568A | + | 102 | >95% | 105 |
| G449K/N568K | + | 284 | >95% | 0.02 |
| N568A/V571A | + | 139 | >95% | 59 |
| R334A/N360K/ E394A | + | 38 | >95% | 0.8 |
| R334A/N360K/ E394A ins2[1] | + | 21 | >95% | 0.001 |
| R334A/N360K/ G449K | + | 320 | >95% | 0.01 |
| R334A/G449A/ N568A | + | 746 | >95% | 424 |
| R334A/G449K/ N568K | + | 50 | >95% | 2.0 |
| R347C/G449A/ N450A | + | 102 | 50% | 0.02 |
| R334A/N360K/ N450A | + | 26 | >95% | 0.3 |
| R334A/N360K/ | + | 445 | >95% | 0.9 |

TABLE 4-continued

Properties of Additional AAV-2 capsid mutants.

| Mutant | Capsid synthesis[2] | DNA packaging | Heparin binding | Transduction |
|---|---|---|---|---|
| E394A/N450A | | | | |
| R334A/N360K/ G449K/N568K | + | 26 | >95% | 0.001 |
| E411A/T413A/ G449A/N450A | + | 372 | >95% | 74 |
| E411A/T413A/ G449A/N450A/ N568A/V571A | + | 437 | >95% | 14 |
| R334A/N360K/ E394A/E411A/ T413A/G449A N450A/N568A/ V571A | + | 152 | >95% | 0.006 |

[1]ins2 is an insertion of the sequence HKDDEAKFFPQ after VP2 amino acid 399.
[2]+ = within 10-fold of wild type.

As shown in Table 4, several mutants were obtained with increased transduction as compared to wild-type capsids. For example, mutants S130T, N133A, D357E, H372N, R451K, G449A/N450A, R334A/N450A, R334A/G449A/N568A, R334A/N568A, G449A/N568A displayed increased transduction. Mutant S130T was the best transducer, with approximately 11 times over wild-type levels. This was remarkable because the only difference between S (serine) and T (threonine) is a $CH_2$ group. Also as seen in Table 4, combination mutants usually transduced at the same level as that of the single mutant with the lowest level of transduction.

Certain amino acids in the capsid overlap the heparin-binding site. This region is termed the "dead zone" or "DZ" herein. Mutations in the dead zone can result in capsids that still bind one of the AAV-2 receptors (e.g., heparin) but do not transduce cells. Amino acid substitutions were made in dead zone amino acids and these substitutions were compared to substitution of the same amino acid with alanine. Results are shown in Table 5.

TABLE 5

Effect of non-alanine substitutions in dead zone.

| Dead zone position | Substitution | Transduction (% of wild type) |
|---|---|---|
| G128 | A | 1.5 |
| | D | 0.02 |
| N131 | A | 0.005 |
| | Q | 0.01 |
| D132 | A | 0.04 |
| | E | 4 |
| | N | 75 |
| H134 | A | 2 |
| | F | 0.2 |
| | Q | 17 |
| | T | 0.4 |
| D357 | A | 4 |
| | E | 427 |
| | N | 128 |
| | Q | 1.6 |
| H372 | A | 0.008[a] |
| | F | 4 |
| | K | 72 |
| | N | 122 |
| | Q | 73 |
| G375 | A | 2.4 |
| | P | 0.01 |
| D392 | A | 0.01 |

TABLE 5-continued

| Effect of non-alanine substitutions in dead zone. | | |
|---|---|---|
| Dead zone position | Substitution | Transduction (% of wild type) |
| | E | 15 |
| | I | 0.5 |
| | N | 0.2 |
| | V | 0.001 |
| E393 | A | 2 |
| | D | 80 |
| | K | 0.2 |
| | Q | 1.2 |

[a]Data from Opie, S. R., et al., J. Virology 77, 6995-7006, (2003)

As shown above, the more conservative the substitution the more functional the dead zone mutant was. For example Q was a good substitute for H. D was a good substitute for E. E or N were good substitutes for D. It was not a surprise that glycine, which has several unique properties was difficult to substitute.

The heparin binding properties of mutant G375P (transduction 0.01% of wild-type) and G375A (transduction 2.4% of wild-type) were compared. Mutant G375P bound heparin at 50% and G375A at 95%. Position 375 might be required for both dead zone and heparin binding site function. Substitution of glycine with alanine in the G375A mutant results in a phenotype that is the same as other dead zone mutants—it binds heparin normally but displays <10% of normal transduction. However, substitution of glycine with proline in the G375P mutant results in a phenotype more similar to a mutant defective in heparin binding (such as R347C/G449A/N450A). Without being bound by a particular theory, the differences in structure between glycine, alanine, and proline imply that the side chain of glycine may be required for dead zone function, since substitution with alanine reduces transduction. The amine group may be required for heparin binding since substitution with proline, which does not have an amine group, affects heparin binding. Alternatively proline substitution may disrupt the structure of the heparin binding site from a distance. There were three mutants (R448A, R451A, R347C/G449A/N450A) that didn't bind heparin, but these were in positions previously known to be required for heparin binding (347, 448, 451).

Neutralization activity of several of these mutants by murine monoclonal antibody (A20) and also by a purified, pooled human IgG was determined. The pooled human IgG preparation was used as it is well characterized, commercially available, highly purified, and it is believed to represent nearly all antigen specificities that would be found in the United States which was the source of blood used to purify the IgG. Results are shown in Table 6.

TABLE 6

| Neutralization by purified, pooled human IgG and murine monoclonal antibody A20 | | |
|---|---|---|
| Mutant | Fold decrease in neutralizing titer[1] | Fold decrease in A20 titer |
| WT | 1.0 | |
| S127A | 2.2* | |
| G128A | 4.1* | |
| S130A | 1.4 | |
| S130T | 1.8 | |
| D132N | 3.8* | |
| N133A | 0.9 | |
| H134Q | 1.5 | |

TABLE 6-continued

| Neutralization by purified, pooled human IgG and murine monoclonal antibody A20 | | |
|---|---|---|
| Mutant | Fold decrease in neutralizing titer[1] | Fold decrease in A20 titer |
| R334A | 2.2* | |
| T354A | 2.9* | |
| D357E | 1.7 | |
| D357N | 1.8 | |
| N360H/S361A | 2.1* | |
| W365A | 10.4* | 0.5 |
| H372K | 1.1 | |
| G375P | 1.9 | |
| D377A | 1.9 | |
| K390A | 2.3* | |
| E394A | 1.5 | |
| E394K | 2.3* | 0.9 |
| K395A | 4.9* | 0.9 |
| F396A | 1.6 | |
| K407A | 3.3* | 1.6 |
| E411A | | 2.7* |
| T413K | 2.6* | |
| E418A | 1.5 | |
| E437A | 2.0* | 0.8* |
| Q438A | 1.3 | |
| R448K | 1.0 | |
| G449A | 2.5* | |
| N450A | 1.6 | |
| Q452A | 1.3 | |
| N568A | 2.0* | |
| K569A | 4.0* | 1.7 |
| V571A | 3.9* | 1.4 |
| V571K | 1.0 | 217* |
| R334A/G449A | 3.9* | |
| R334A/N568A | 2.4* | |
| G449A/N568A | 1.7 | |
| N568A/V571A | 2.5* | |
| R334A/G449A/N568A | 3.0* | |
| E411A/T413A/G449A/N450A | 1.0 | |
| E411A/T413A/G449A/N450A/N568A/V571A | 1.3 | |

[1]*= statistically significant, $p < 0.05$. Titers were determined by doing 2-fold dilutions of IgG. The data was plotted using Sigma Plot software and the reciprocal of the dilution at which 50% neutralization occurred is defined as the titer.

As shown in the table, 21 mutants (S127A, G128A, D132N, R334A, T354A, N360H/S361A, W365A, K390A, E394K, K395A, K407A, T413K, E437A, G449A, N568A, K569A,V571A, R334A/G449A, R334A/N568A, N568A/V571A, R334A/G449A/N568A) were from 2-10 fold more resistant to neutralization by a large pool of human IgG compared to native AAV-2 capsid. As would be expected, some of the mutants that were resistant to neutralization by pooled human IgG were also resistant to neutralization by individual human sera (e.g., R334A, N360H/S361A, G449A, N568A, V571A). Without being bound by a particular theory, epitopes that contain those amino acids may bind antibody with high affinity or at high frequency. However, some mutants resistant to neutralization by pooled human IgG were not identified as resistant to individual sera, possibly because epitopes that contain those amino acids are more rarely found in the human population. In addition, some mutants were resistant to neutralization by individual sera but not to pooled human IgG (e.g., E394A, N450A). In these cases it is possible the antibodies that bind to epitopes that contain these amino acids are low affinity or low abundance such that mutations that affect their binding are not detectable in the context of a large complex mixture of IgG.

As can be seen in FIG. 7, these mutations are scattered at various locations across the surface of AAV-2. The size of the area they cover is 2-3 times the size of an average epitope, implying there may be at least 2-3 epitopes involved in neutralization by the sum total of all human IgGs.

Combinations of single, neutralization resistance mutants sometimes resulted in a slightly higher degree of neutralization resistance compared to the single mutants that comprised a multiple mutant. However the degree of the effect clearly is not multiplicative for these mutants at these levels of neutralization resistance.

Two more mutants resistant to neutralization by the murine monoclonal antibody A20 were also identified: E411A which is 2.7-fold resistant and V571K which is 217-fold resistant to neutralization by A20. The V571K mutant provides evidence for a concept termed by the present inventors as "lysine scanning". Rather than removing part of an antibody binding site by changing an amino acid with a large side chain to one with a smaller side chain such as alanine, the concept of lysine scanning is to substitute an amino acid that has a small side chain (e.g., V571) with lysine which has a large side chain. Rather than removing part of an antibody binding site as might be the case for alanine substitutions, the aim of lysine scanning is to insert larger amino acids that could sterically interfere with antibody binding. Lysine was chosen since it is commonly found on the surface of AAV-2 and thus likely to be an accepted substitution. However, other large amino acids such as arginine, trytophan, phenylalanine, tyrosine, or glutamine may also result in a similar effect without compromising biological activity. Note that while V571A is not resistant to neutralization by the murine A20 antibody, V571K is 217 fold more resistant to neutralization by A20 than is native V571 AAV-2 capsid.

V571K is located on the plateau, immediately adjacent to the four other mutants identified as resistant to A20 neutralization (Q126A, S127A, S247A, Q248A; Table 3). However E411A is located on the spike, albeit close enough to Q126A, S127A, S247A, Q248A and V571K to be within the same epitope. Inclusion of E411 in the A20 epitope evidences that A20 may bind to both the plateau and the spike, i.e. across the canyon. Molecular modeling suggests that one of AAV-2 receptors, the basic FGF receptor (PDB ID: 1FQ9), could fit very well in the AAV-2 canyon (in a manner and location remarkably similar to the way the transferrin receptor is thought to bind to canine parvovirus). If the basic FGF receptor binds to the AAV-2 canyon, then binding of A20 across the canyon would block binding of the basic FGF receptor and explain the observation that A20 neutralizes AAV-2 by blocking entry, a step in transduction that the basic FGF receptor is likely to mediate.

The plateau and spike area may bind antibodies that neutralize other AAVs by preventing receptor binding. For example AAV-5 has been shown to require the PDGF receptor for entry into cells (Di Pasquale et al., *Nature Medicine* (2003) 9: 1306-1312). Although the structure of the PDGF receptor is not known, it is homologous in amino acid sequence to the basic FGF receptor. For example, both are composed of similar repetitive Ig-like sequence domains and thus would be expected to have similar 3-dimensional structures. Thus, it is possible that the PDGF receptor may bind to the AAV-5 canyon.

V571A, but not V571K is resistant to neutralization by pooled human IgG. Conversely V571K, but not V571A is resistant to neutralization by murine monoclonal A20. It is possible that antibodies in the human IgG pool bind directly to V571. Substitution of the valine side chain for the smaller alanine side chain may result in less binding by human IgG. The lysine side chain may still provide enough hydrophobic contacts to allow binding to occur, but not be so large as to prevent binding. A20 may not bind directly to V571 (explaining the absence of an effect of the V571A mutant on binding or neutralization by A20). However A20 clearly binds in the vicinity of V571. It is possible that V571K indirectly interferes with A20 binding, for example by steric interference.

An IgG ELISA was also done. There are many potential mechanisms of neutralization, especially in vivo. Binding of an IgG to AAV in a region that is not required for the function of AAV could still lead to reduction of the ability of AAV to deliver genes. For example, the primary function of macrophages is to bind foreign organisms that are bound to antibodies. When an antibody-bound organism is bound to a macrophage (via Fc receptors) the foreign organism is engulfed and destroyed. Another potential route that antibodies could use in order to neutralize AAV is by cross-linking. Antibodies are bivalent and AAV would likely have 60 antibody binding sites per epitope (and possibly multiple epitopes). Thus, as is well documented in the scientific literature, at certain antibody and virus concentrations, a cross-linked network of AAVs and antibodies can form. Such immune complexes can become so large that they precipitate or become lodged in the vasculature prior to reaching a target organ. For this reason, antibodies that bind AAV in vivo, on areas of AAV that are not functionally significant, can result in reduced transduction as much as antibodies that do bind to functionally significant areas. Results are shown in Table 7.

TABLE 7

| | IgG ELISA | |
|---|---|---|
| Mutant | Fold decrease in binding of human IgG | Fold decrease in binding of murine A20 |
| Wild type | 1 | 1 |
| S130A | 1 | 1 |
| S130T | 1 | 1 |
| D132N | 1 | 1 |
| H134Q | 1 | 1 |
| G246A | 1 | 1 |
| R334A | 1 | 1 |
| D357E | 1 | 1 |
| N360H | 1 | 1 |
| H372K | 1 | 1 |
| H372Q | 1 | 1 |
| E393D | 1 | 1 |
| T413K | 1 | 1 |
| G449A | 1 | 1 |
| N568K | 1 | 1 |
| N568A | 1 | 1 |
| V571K | 10 | 10 |
| E411A, T413A | 1 | 1 |
| N568A, N571A | 1 | 1 |
| E411A, T413A, G449A, N450A | 1 | 1 |
| R334A, G449A, N568A | 1 | 1 |
| R334A, G449A | 1 | 1 |
| R334A, N568A | 1 | 1 |
| G449A, N568A | 1 | 1 |

As shown in Table 7, one mutant (V571K) was identified that bound both A20 and a pool of human IgG 10 times worse than native AAV-2. In the all-A20 ELISA binding of mutant V571K was reduced 10-fold. In an all-human IgG ELISA binding of mutant V571K was reduced 10-fold. When an A20/IgG sandwich ELISA format was used, binding of mutant V571K was reduced 100-fold. Position (571)

is immediately adjacent to positions 126, 127, 247 and 248 on the surface of the AAV-2 capsid. Positions 126, 127, 247 and 248 were identified as important for neutralization by the mouse monoclonal antibody A20. Therefore this region may be antigenic in both mice and humans.

To summarize, several mutations to the external surface of AAV-2 capsid that reduced neutralization by antibodies, but had minimal effects on biological properties were identified. In particular, 127 mutations were made at 72 positions (55% of surface area) deemed most likely to be accessible to antibody binding based on manual docking of IgG and AAV-2 structures. Single alanine substitutions (57), single non-alanine substitutions (41), multiple mutations (27), and insertions (2) were made. All mutants made capsid proteins and packaged DNA at levels within 10-fold of wild type. All mutants bound heparin as well as wild-type, except for six which were close to or within the heparin binding site. 42 of 98 single mutants transduced at least as well as wild-type. Several mutants had increased transducing activity. One, an S to T mutant, had 11-fold greater transducing activity than wild type. Combination (up or down) mutants usually transduced at the same level as that of the single mutants with the lowest level of transduction.

13 of 15 single alanine substitution mutants with <10% transduction activity were adjacent to each other in an area (10% of surface) that overlaps the heparin-binding site. Although these "dead zone (DZ)" mutants had from 0.001%-10% of normal transduction activity, all of them bound heparin as efficiently as wild-type. Transduction by DZ mutants could be increased, and in three cases restored to wild-type levels, by making conservative substitutions.

Five mutants had reduced binding to a mouse monoclonal antibody (A20) in an ELISA and were 2.5-217 fold more resistant to neutralization by A20 in vitro. These 5 mutants were adjacent to each other and to the DZ. A total of 21 single mutants were 2-10 fold resistant to neutralization by three human sera or by a large pool of purified human IgG (IVIG, Panglobulin) compared to wild-type. Different sets of mutations conferred resistance to different human sera. The location of these mutations was widespread. The size of the area they covered suggested human sera neutralize AAV-2 by binding at least two epitopes. Three mutants were resistant to all sera tested, but combinations of these three mutants did not increase resistance to neutralization by IVIG. One (V to K) mutant was identified that bound IVIG 10-fold worse than wild-type in an all-IVIG ELISA. However, this mutant was not resistant to IVIG neutralization.

In summary, mutations in the "dead zone" affect transduction, but not heparin binding. Mutations around the DZ can increase transduction or decrease binding of antibodies. The DZ is very acidic (6 acidic, 0 basic amino acids). Without being bound by a particular theory, it may be a binding site for a basic protein, such as bFGF or the bFGF receptor. Since the dead zone is adjacent to the heparin binding site on AAV-2 it may be that if a protein binds to the dead zone, then that protein may also bind heparin. Both bFGF and the bFGF receptor bind heparin.

Example 2

Factor IX Expression in Mice Using Mutant AAV-hF.IX rAAV-F.IX is prepared using the rAAV-2 hF.IX vector and the methods described above. Freeze-thaw lysates of the transfected cells are precipitated, rAAV virions are purified by two cycles of isopycnic centrifugation; and fractions containing rAAV virions are pooled, dialysed, and concentrated. The concentrated virions are formulated, sterile filtered (0.22 μM) and aseptically filled into glass vials. Vector genomes are quantified by the "Real Time Quantitative Polymerase Chain Reaction" method (Real Time Quantitative PCR. Heid C. A., Stevens J., Livak K. J., and Williams P. M. 1996. Genome Research 6:986-994. Cold Spring Harbor Laboratory Press).

Female mice 4-6 weeks old are injected with mutant rAAV-hF.IX virions. Mice are anesthetized with an intraperitoneal injection of ketamine (70 mg/kg) and xylazine (10 mg/kg), and a 1 cm longitudinal incision is made in the lower extremity. Mutant recombinant AAV-hF.IX ($2\times10^{11}$ viral vector genomes/kg in HEPES-Buffered-Saline, pH 7.8) virions is injected into the tibialis anterior (25 μL) and the quadriceps muscle (50 μL) of each leg using a Hamilton syringe. Incisions are closed with 4-0 Vicryl suture. Blood samples are collected at seven-day intervals from the retro-orbital plexus in microhematocrit capillary tubes and plasma assayed for hF.IX by ELISA. Human F.IX antigen in mouse plasma is assessed by ELISA as described by Walter et al. (*Proc Natl Acad Sci USA* (1996) 3: 3056-3061). The ELISA does not cross-react with mouse F.IX. All samples are assessed in duplicate. Protein extracts obtained from injected mouse muscle are prepared by maceration of muscle in PBS containing leupeptin (0.5 mg/mL) followed by sonication. Cell debris is removed by microcentrifugation, and 1:10 dilutions of the protein extracts are assayed for hF.IX in the ELISA. Circulating plasma concentrations of hF.IX is measured by ELISA at various time points post-IM injection (e.g., zero, three, seven, and eleven weeks).

Example 3

Hemophilia B Treatment in Dogs with Mutant AAV-cF.IX

A colony of dogs having severe hemophilia B comprising males that are hemizygous and females that are homozygous for a point mutation in the catalytic domain of the canine factor IX (cF.IX) gene, is used to test the efficacy of cF.IX delivered by mutant rAAV virions (rAAV-cF.IX). The severe hemophilic dogs lack plasma cF.IX, which results in an increase in whole blood clotting time (WBCT) to >60 minutes (normal dogs have a WBCT between 6-8 minutes), and an increase in activated partial thromboplastin time (aPTT) to 50-80 seconds (normal dogs have an aPTT between 13-18 seconds). These dogs experience recurrent spontaneous hemorrhages. Typically, significant bleeding episodes are successfully managed by the single intravenous infusion of 10 mL/kg of normal canine plasma; occasionally, repeat infusions are required to control bleeding.

Under general anesthesia, hemophilia B dogs are injected intramuscularly with rAAV1-cF.IX virions at a dose of $1\times10^{12}$ vg/kg. The animals are not given normal canine plasma during the procedure.

Whole blood clotting time is assessed for cF.IX in plasma. Activated partial thromboplastin time is measured. A coagulation inhibitor screen is also performed. Plasma obtained from a treated hemophilic dog and from a normal dog is mixed in equal volumes and is incubated for 2 hours at 37° C. The inhibitor screen is scored as positive if the aPTT clotting time is 3 seconds longer than that of the controls (normal dog plasma incubated with imidazole buffer and pre-treatment hemophilic dog plasma incubated with normal dog plasma). Neutralizing antibody titer against AAV vector is assessed.

Example 4

Hemophilia B Treatment in Humans with Mutant AAV-hF.IX

A. Muscle Delivery

On Day 0 of the protocol patients are infused with hF.IX concentrate to bring factor levels up to ~100%, and, under ultrasound guidance, mutant rAAV-h.FIX virions are injected directly into 10-12 sites in the *vastus lateralis* of either or both anterior thighs. Injectate volume at each site is 250-500 μL, and sites are at least 2 cm apart. Local anesthesia to the skin is provided by ethyl chloride or eutectic mixture of local anesthetics. To facilitate subsequent muscle biopsy, the skin overlying several injection sites is tattooed and the injection coordinates recorded by ultrasound. Patients are observed in the hospital for 24 h after injection; routine isolation precautions will be observed during this period to minimize any risk of horizontal transmission of virions. Patients are discharged and seen daily in outpatient clinic daily for three days after discharge, then weekly at the home hemophilia center for the next eight weeks, then twice monthly up to five months, them monthly for the remainder of the year, then annually in follow-up. Circulating plasma levels of hF.IX are quantified using ELISA as described above.

B. Liver Delivery

Using the standard Seldinger technique, the common femoral artery is cannulated with an angiographic introducer sheath. The patient is then heparinized by IV injection of 100 U/kg of heparin. A pigtail catheter is then advanced into the aorta and an abdominal aortogram is performed. Following delineation of the celiac and hepatic arterial anatomy, the proper HA is selected using a standard selective angiography catheter (Simmons, Sos-Omni, Cobra or similar catheters). Prior to insertion into the patient, all catheters are flushed with normal saline. Selective arteriogram is then performed using a non-ionic contrast material (Omnipaque or Visipaque). The catheter is removed over a 0.035 wire (Bentsen, angled Glide, or similar wire). A 6F Guide-sheath (or guide catheter) is then advanced over the wire into the common HA. The wire is then exchanged for a 0.018 wire (FlexT, Microvena Nitenol, or similar wire) and a 6X2 Savvy balloon is advanced over the wire into the proper HA distal to the gastrodoudenal artery. The wire is then removed, the catheter tip position confirmed by hand injection of contrast into the balloon catheter, and the lumen flushed with 15 ml of heparinized normal saline (NS) to fully clear the contrast. Prior to infusion of the AAV-hFIX, the balloon is inflated to 2 atm to occlude the flow lumen of the HA. AAV-hFIX, at a dose of 8×10E10=2×10E12, is brought to a final volume of approximately less than or equal to 40 ml (depending on dose and weight of patient) and is then infused over 10-12 minutes using an automatic volumetric infusion pump. Three milliliters (ml) of normal saline (NS) are then infused (at the same rate as the AAV-hFIX), to clear the void volume of the catheter. The balloon remains inflated for 2 minutes at which time the balloon is deflated and the catheter removed. A diagnostic arteriogram of the femoral puncture site is then performed in the ipsilateral anterior oblique projection. The puncture site is closed by standard methods, e.g., utilizing a percutaneous closure device using either a 6 F Closer (Perclose Inc., Menlo Park, Calif.) or a 6 F Angioseal, or by manual compression applied for 15 to 30 minutes at the site of catheter removal.

Example 5

Isolation and Characterization of a New Caprine AAV

A. Cell Culture and Virus Isolation

Ovine adenovirus preparations with evidence of parvovirus contamination were isolated from caprine ileum as follows. Tissue was homogenized in Eagle's MEM medium containing Earles salts (PH 7.2) and gentomycin. The homogenate was clarified by low speed centrifugation (1,500×g) for 20 minutes and filter-sterilized though a 0.45 μm device. Supernatant (500 μl) was inoculated onto a 25 $cm^2$ flask containing primary cultures of fetal lamb kidney cells at passage 3 and incubated with fetal bovine serum (USA) and lactalbumin hydrolysate (USA) at 37° C. in humid, 5% $CO_2$ incubator for one week. Cells were trypsinized, split, and incubated again as described above and finally assayed for typical adenoviral cytophatic effect (CPE). Flasks showing CPE were frozen at −70° C., thawed and layered onto other cell types. These flasks were later incubated and tested for CPE.

Other cell types used included non-immortalized (passage 8) ovine fetal turbinate cells derived from fetal ovine tissue and Maden Darby bovine kidney cells, maintained by long-term passage (used at passage 160). Porcine trypsine (USA) was used in all tissue culture processes and no human cell cultures or products were used.

B. Viral DNA Isolation and AAV Sequence Identification and Comparison

Four preparations from different cell cultures and passages were processed individually for DNA extraction. Virus-containing supernatant was treated with proteinase K (200 μg) in digestion buffer (10 mM Tris-HCl (PH 8.0), 10 mM EDTA (PH 8.0) and 0.5% SDS) and incubated at 37° C. for 1 hour. Following phenol chloroform extraction and ethanol precipitation the viral DNA was resuspended in TE. The DNA content of each preparation was determined by PicoGreen DNA quantitation (Molecular Probes, Eugene, Oreg.) and the preparations were diluted to 20 ng/μl to standardize DNA concentration for subsequent PCR assays.

Oligonucleotide Primers

Oligonucleotide primers were selected on the basis of sequence alignments from segments that were highly conserved among known AAVs.

The forward primer 1 (GTGCCCTTCTACGGCTGCGTCAACTGGACCAATGAGAACTTTCC) (SEQ ID NO:23), was complementary to the helicase domain and the reverse primer 2 (GGAATCGCAATGCCAATTTCCTGAGGCATTAC) (SEQ ID NO:24), was complementary to the DNA binding domain. The expected size of PCR fragments was 1.5 kb.

PCR Amplifications

All reactions were performed in 50 μl in an automated Eppendorf Mastercycler Gradient thermocycler (PerkinElmer, Boston, Mass.). Each reaction mixture contained 200 ng of template DNA, 1 μM each oligonucleotide primer, 1 mM $Mn(Oac)_2$, 200 μM each deoxynucleoside triphosphate (dATP, dCTP, dGTP, and dTTP), and 1.0 unit of rTth polymerase, XL (Applied Biosystems, Foster City, Calif.) in 1×XL Buffer II. Ampliwax PCR gem 100 was used to facilitate hot start (Applied Biosystems, Foster City, Calif.). Cycling conditions were as follows: 2 min of denaturation at 94° C., followed by 35 cycles of 15 s of denaturation at 94° C., 30 s of annealing at 45° C., and 2 min of elongation at 72° C.

PCR products (10 μl) were electrophoretically separated in a 1% NuSieve agarose gel (FMC BioProducts, Rockland, Minn.), stained with ethidium bromide, and visualized by UV light. DNA molecular markers were used on each gel to facilitate the determination of the sizes of the reaction products.

To control for specificity of the assay, PCR was also performed with 100 ng of DNA from a plasmid containing AAV2 sequences.

DNA Sequencing

PCR products were purified on 1% low-melting agarose gels (FMC Bioproducts, Rockland, Me.), and the sequences were determined using primers designed from AAV-5 sequences.

Sequence data was analyzed with the NTI vector suite software package (InforMax, Frederick, Md.).

Figure 16:
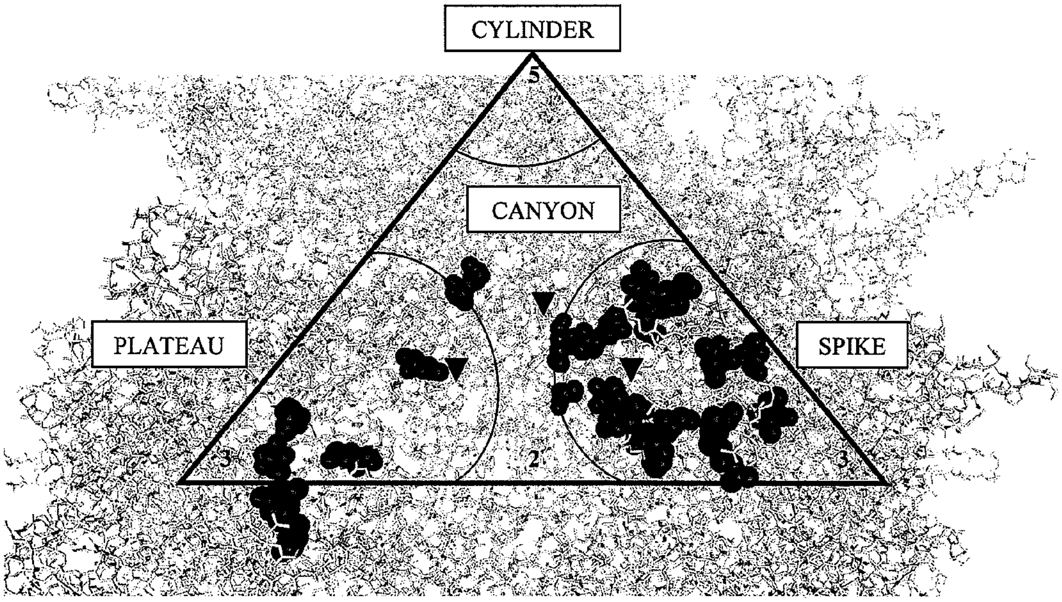
FIG. 16 shows the predicted location of the surface amino acids that differ between AAV-5 and caprine AAV, based on the surface structure of the AAV-2 capsid. The 3 filled triangles represent insertions in caprine AAV, relative to AAV-2, that are likely to be located on the surface.

Virus preparations from different cell cultures and passages were processed individually for DNA extraction and PCR analysis. PCR amplification using primers forward 1 and reverse 2 revealed the presence of parvovirus-like sequences in all four preparations. Sequence analysis revealed the presence of AAV sequences. The VP1 ORF of caprine AAV, corresponding to nucleotides 2,207 to 4,381 of AAV-5 genome, has 93% nucleotide identity (2,104/2,266, Gaps 6/2,266) with primate AAV-5 (see FIGS. 12A-12B) isolated from humans (*J. Virol* 1999; 73: 1309-1319). Protein comparison showed 94% identity (682/726) and 96% similarity (698/726) between the primate AAV-5 and caprine AAV VP1 proteins (see, FIG. 13). Most if not all mutations appeared to be on the surface (see, FIG. 15). FIG. 16 shows the predicted location of the surface amino acids that differ between AAV-5 and caprine AAV, based on the surface structure of the AAV-2 capsid. The 3 filled triangles represent insertions in caprine AAV, relative to AAV-2, that are likely to be located on the surface.

Without being bound by a particular theory, surface mutations were probably driven by selective pressure due to the humoral immune system and/or adaptation to ruminant receptors. The lack of changes in non-surface exposed areas may imply a lack of pressure from the cellular immune response. These mutated regions in the caprine virus may improve the resistance to pre-existing human anti-AAV5 antibodies.

The caprine AAV sequence was compared to other AAV serotypes and these serotypes were compared with each other in order to analyze the differences in the non-conserved region. In particular, FIGS. 14A-14H show a comparison of the amino acid sequence of VP1 from primate AAV-1, AAV-2, AAV-3B, AAV-4, AAV-6, AAV-8, AAV-5 and caprine AAV. Conserved amino acids in the sequences are indicated by * and the accessibility of the various amino acid positions based on the crystal structure is shown. B indicates that the amino acid is buried between the inside and outside surface. I indicates the amino acid is found on the inside surface and O indicates the amino acid is found on the outside surface.

The non-conserved region between AAV-5 and caprine AAV includes 43 mutations. 17 of these 43 mutations are non-conserved between AAV-2 and AAV-8. Only one of these mutations originated in the same amino acid in caprine AAV and AAV-8. The non-conserved region between AAV-5 and caprine AAV includes 348 amino acids. This non-conserved region is compressed to 157 amino acids when analyzing the region containing the 17 joint mutations.

Tables 8-11 show the results of the comparisons.

TABLE 8

Mutations in surface (O) residues of AAV-2 vs. AAV-8 and AAV-5 vs. Caprine-AAV

| Region | AAV-2 vs. AAV-8 mutations (x)/surface residues (O) | AAV-5 vs. Caprine-AAV mutations (*)/surface residues (O) |
|---|---|---|
| 100-200 | 04/19 (+2 insertions) | 00/19 |
| 200-300 | 01/20 | 01/20 |
| 300-400 | 16/31 | 03/30 |
| 400-500 | 20/46 (+1 insertion) | 11/43 (+1 insertion) |
| 500-600 | 13/27 | 04/30 |
| 700-750 | 05/24 | 01/24 |
| 100-750 | 59/167 (35%) 65% identity | 20/167 (12%) 88% identity |

TABLE 9

Mutations in surface (O) residues of AAV-2 vs. all AAVs.

| Region | AAV2 vs. AAV1 mut/surface | AAV2 vs. AAV3a mut/surface | AAV2 vs. AAV4 mut/surface | AAV2 vs. AAV5 mut/surface | AAV2 vs. AAV6 mut/surface | AAV2 vs. AAV7 mut/surface | AAV2 vs. AAV8 mut/surface | AAV2 vs. Caprine AAV mut/surface |
|---|---|---|---|---|---|---|---|---|
| 100-200 | 01/19 (1 ins) | 00/19 | 08/19 (3 del) | 10/19 (1 ins) | 01/19 | 05/19 (1 ins) | 04/19 (2 ins) | 10/19 (1 ins) |
| 200-300 | 02/20 | 02/20 | 07/20 (3 ins) | 06/20 (2 ins) | 01/20 | 03/20 (1 ins) | 01/20 | 06/20 (2 ins) |
| 300-400 | 15/31 | 11/31 | 24/31 | 17/30 (6 del) | 17/31 | 14/31 | 16/31 | 18/30 (6 del) |
| 400-500 | 21/46 | 14/46 | 36/46 (ins, 1del) | 36/44 (3 ins) | 21/46 | 22/46 (1 del) | 20/46 (1 ins) | 37/44 (3 ins) |
| 500-600 | 10/27 | 07/27 | 15/27 | 15/30 | 10/27 | 10/27 | 13/27 | 17/30 |
| 700-750 | 06/24 | 00/24 | 13/24 | 11/24 | 06/24 | 07/24 | 05/24 | 11/24 |
| 100-750 | 55/167 (33%) 67% identity | 34/167 (20%) 80% identity | 103/167 (62%) 38% identity | 95/167 (57%) 43% identity | 56/167 (34%) 66% identity | 61/167 (37%) 63% identity | 59/167 (35%) 65% identity | 99/167 (59%) 41% identity |

TABLE 10

| Surface identity (%) | AAV1 | AAV3a | AAV4 | AAV5 | AAV6 | AAV7 | AAV8 | Caprine AAV |
|---|---|---|---|---|---|---|---|---|
| AAV2 | 67 | 80 | 38 | 43 | 66 | 63 | 65 | 41 |
| AAV5 | | | | | | | | 88 |

TABLE 11

| Capsid similarity (%) | AAV1 | AAV3a | AAV4 | AAV5 | AAV6 | AAV7 | AAV8 | Caprine AAV |
|---|---|---|---|---|---|---|---|---|
| AAV2 | 83 | 87 | 59 | 56 | 83 | 82 | 83 | 56 |

Example 6

Immunoreactivity of Caprine AAV and Comparison to Other AAVS

A. Neutralization Activity of Primate AAV Serotypes

The neutralization activity of the primate AAV serotypes indicated in Table 12 was assessed using the methods described above. Immunoreactivity was determined using a purified pooled human IgG (designated IVIg 8 in Tables 12 and 13).

As shown in Tables 12 and 13, most serotypes were neutralized by the pooled human IgG at clinically relevant concentrations. AAV-4 and AAV-8 were more resistant to neutralization than AAV-1, AAV-2 and AAV-6, which were more resistant to neutralization than AAV-3, which was more resistant to neutralization than AAV-5.

B. Neutralization Activity of Caprine AAV vs. Primate AAV Serotypes

The neutralization activity of goat AAV was compared to primate AAV-5 using the methods described above. Immunoreactivity was determined using a purified pooled human IgG (designated IVIg 8 in Table 14). As shown in Table 14, caprine AAV displayed more resistance to neutralization than AAV-5. Table 14 also shows the neutralization activity of AAV-1, AAV-2, AAV-3, AAV-4, AAV-5, AAV-6 and AAV-8, as determined in the above example, relative to the caprine AAV.

In another experiment, the neutralization activity of caprine AAV relative to AAV-8 was examined using three different purified pools of human IgG, designated IVIg 3, IVIg 6 and IVIg 8, respectively, in Tables 15 and 16. As shown in the tables, caprine AAV was more resistant to neutralization than AAV-8 using all three pools of human IgG.

TABLE 12

| | IVIg 8 (ug/ul) | | | | |
|---|---|---|---|---|---|
| Vector | 50 | 10 | 1 | 0.1 | 0.01 |
| AAV 1 | 0 | 14 | 69 | 86 | 100 |
| AAV 2 | 0 | 2 | 82 | 100 | 100 |

TABLE 12-continued

| | IVIg 8 (ug/ul) | | | | |
|---|---|---|---|---|---|
| Vector | 50 | 10 | 1 | 0.1 | 0.01 |
| AAV 3 | 0 | 0 | 45 | 62 | 92 |
| AAV 4 | 49 | 87 | 100 | 100 | 100 |
| AAV 5 | 0 | 1 | 1 | 17 | 95 |
| AAV 6 | 0 | 14 | 66 | 81 | 100 |
| AAV 8 | 0 | 83 | 77 | 88 | 90 |

The first concentration for each serotype showing >50% blue cells compared to the control is highlighted.

TABLE 13

| Vector | Lowest concentration of IVIG (mg/ml) showing >50% neutralization of the virus IVIG (Panglobulin, ZLB Bioplasma, lot# 1838-00351)) |
|---|---|
| AAV1 | 10 |
| AAV2 | 10 |
| AAV3B | 1 |
| AAV4 | 50 |
| AAV5 | 0.1 |
| AAV6 | 10 |
| AAV8 | 50 |

TABLE 14

| Vector | Lowest concentration of IVIG (mg/ml) showing >50% neutralization of the virus IVIG (Panglobulin, ZLB Bioplasma, lot# 1838-00351)) |
|---|---|
| AAV5 | 0.1 |
| Caprine-AAV | 50 |

TABLE 15

| | IVIg 3 (ug/ul) | | | | | |
|---|---|---|---|---|---|---|
| Vector | 50 | 40 | 20 | 10 | 1 | 0.1 |
| AAV 8 | 1 | 2 | 32 | 33 | 115 | 105 |
| Goat AAV | 16 | 32 | 81 | 69 | 92 | 102 |
| | IVIg 6 (ug/ul) | | | | | |
| Vector | 50 | 40 | 20 | 10 | 1 | 0.1 |
| AAV 8 | 0 | 0 | 32 | 22 | 88 | 110 |
| Goat AAV | 10 | 14 | 68 | 113 | 125 | 126 |
| | IVIg 8 (ug/ul) | | | | | |
| Vector | 50 | 40 | 20 | 10 | 1 | 0.1 |
| AAV 8 | 0 | 0 | 11 | 44 | 95 | 105 |
| Goat AAV | 8 | 14 | 72 | 80 | 93 | 120 |

TABLE 16

| | Lowest concentration of IVIG (mg/ml) showing >50% neutralization of the virus. | | |
|---|---|---|---|
| Vector | IVIG (Panglobulin, ZLB Bioplasma, lot # 1838-00299) | IVIG (Panglobulin, ZLB Bioplasma, lot# 1838-00351) | IVIG (Baxter, Polygam S/D, lot# 02J06AX11) |
| AAV8 | 10 | 10 | 10 |
| Caprine-AAV | 40 | 40 | 40 |

Example 7

Ability of Caprine AAV to Transduce Striatal Neurons and Glial Cells and Comparison to Other AAVS In order to examine the ability of the various AAVs to transduce striatal neurons and glial cells, the following experiment was done. Primary cultures of dissociated striatal neurons were prepared from embryonic day 18 Sprague-Dawley rat embryos. Dissected striatal tissue was minced into small pieces and was incubated in trypsin for 30 min. The tissue was then triturated through a Pasteur pipette and cells were plated at a density of 350,000 per well in 12-well culture dishes containing round glass 18 mm coverslips coated with poly-D-lysine. The culture medium was neurobasal medium supplemented with 2% B-27, 0.5 mM L-glutamine and 25 mM L-glutamic acid. Cultures were maintained at 37° C. in 5% $CO_2$ and were used in experiments two to three weeks after dissociation. At this stage, dopaminegic and striatal neurons are distinguished both morphologically and by expression of biological markers.

The striatal cultures were incubated for five days with $10^4$ MOI rAAV virions derived from AAV-2, AAV-4, AAV-5, AAV-6, AAV-8, and caprine AAV that contained the β-galactosidase gene (LacZ), prepared using the triple transfection method described in Example 1. For caprine AAV, the capsid coding sequence present in pHLP19 (described in U.S. Pat. No. 6,001,650, incorporated herein by reference in its entirety) was substituted with the caprine VP1 coding sequence as follows. Briefly, plasmid pHLP19 was digested with SwaI and AgeI (New England Biolabs, Beverly, Mass. 01915-5599), the fragment of interest was purified on a 1% low-melting agarose gel (FMC Bioproducts, Rockland, Me.), and used for ligation with the PCR fragment containing the caprine capsid. The caprine capsid PCR fragment was amplified using a forward primer: AAATCAGGTATGTCTTTTGTTGATCACCC (SEQ ID NO:27) and a reverse primer: ACACGAATTAACCGGTTTATTGAGGGTATGCGACATGAATGGG (SEQ ID NO:28). The PCR fragment was digested with the enzyme AgeI (New England Biolabs, Beverly, Mass. 01915-5599) and used for ligation with the digested plasmid.

Efficient and sustained expression of the β-gal protein was seen in striatal neurons following transduction with the vectors. Expression efficiency was highest in AAV6 followed by AAV8, AAV2, AAV5, caprine AAV and AAV4. AAV6 transduced neurons exclusively, whereas AAV5-mediated gene transfer was inefficient in neurons but transduced the glial cells. All other vectors transduced both neurons and glial cells.

Example 8

Ability of Caprine AAV to Transduce Muscle and Comparison to Other AAVS

In order to determine the ability of the various AAVs to transduce muscle in the presence or absence of IVIG, the following experiment was done. Male SCID mice (15-25 g) were injected intramuscularly with 2e11 vector genomes of caprine rAAV virions, rAAV-1 virions, or rAAV-8 virions (5 mice per group), each of said virions encoding human factor IX. These virions were made using the triple transfection method described in Example 1. The capsid coding sequence present in pHLP19 was substituted with the caprine VP1 coding sequence as described above. Retro-orbital blood was collected 1, and 2 weeks after vector injection and plasma was extracted. Mice tested with IVIG (Carimune: purified immunoglobulin from a pool of human serum, ZLB Bioplasma, lot# 03287-00117) were injected via the tail vein (250 μl), 24 hours before the vector injection. Human FIX was measured in the plasma samples using a hFIX ELISA.

Figure 17:
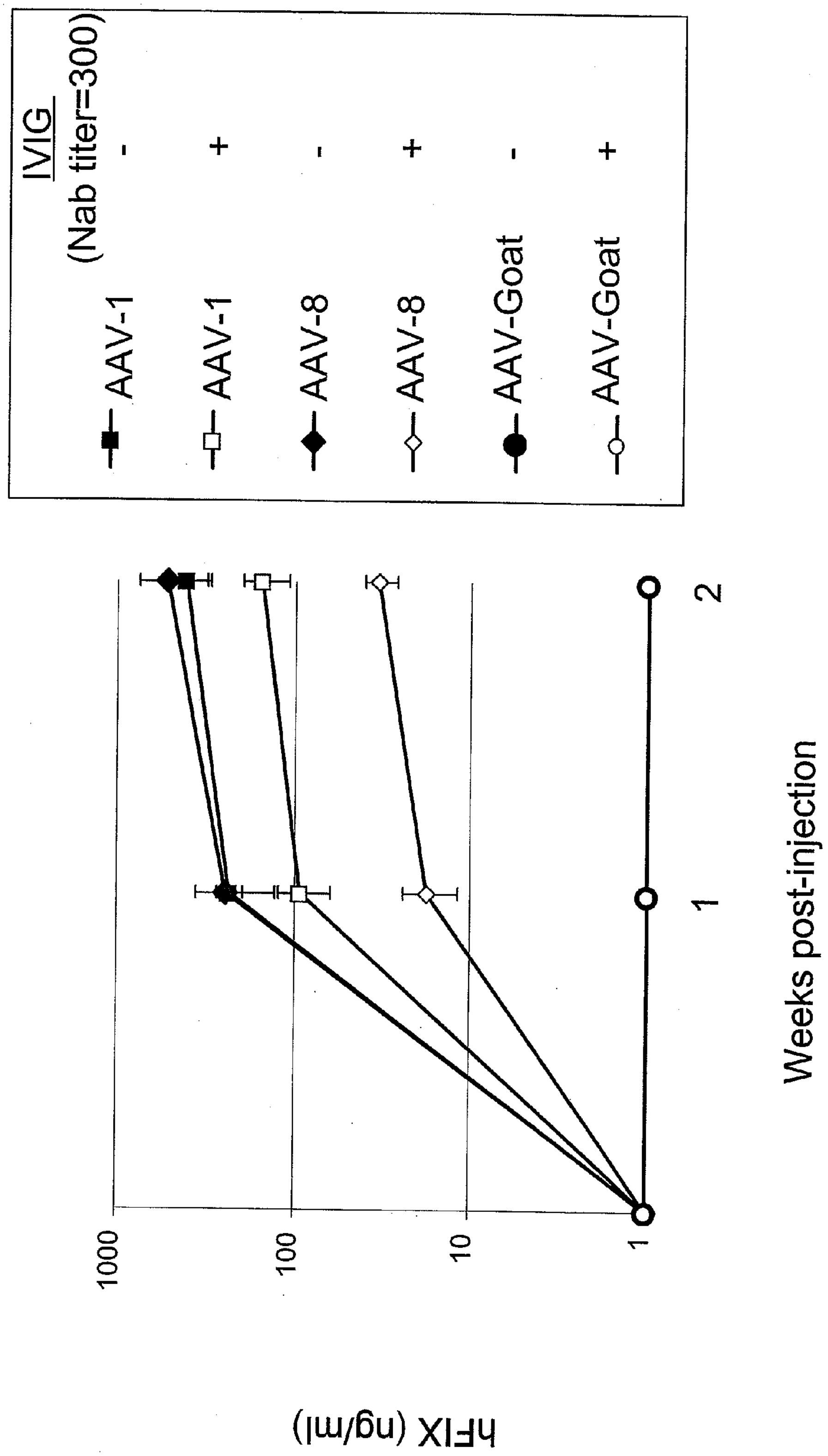
FIG. 17 shows transduction of muscle in IVIG-treated SCID mice following intramuscular administration of various rAAV hFIX virions.

As shown in FIG. 17, caprine rAAV virions did not transduce muscle. the rAAV-8 and rAAV-1 virions displayed similar levels of expression of hFIX. AAV-1 was more resistant to neutralization than AAV-8 in vivo.

Example 9

Ability of Caprine AAV to Transduce Liver and Comparison to other AAVS and Biodistribution of Proteins Expressed From Genes Delivered by Caprine AAV Virions In order to determine the ability of the various AAVs to transduce liver in the presence or absence of IVIG, the following experiment was done. Male SCID mice (15-25 g) were injected via the tail vein with 5e11 vector genomes of caprine rAAV virions or rAAV-8 virions (5 mice per group). The virions included the gene encoding human factor IX (hFIX). The rAAV-2 virion data below was from another experiment. In particular, the virions were generated using plasmid pAAV-hFIX16, containing the human factor IX gene under the control of a liver-specific promoter (described in Miao et al., *Mol. Ther.* (2000) 1: 522-532). Plasmid pAAV-hFIX16 is an 11,277 bp plasmid encoding a human Factor IX minigene. In this construct, the FIX cDNA is interrupted between exons 1 and 2 with a deleted form of intron 1 which has been shown to increase expression of FIX. FIX expression is under the transcriptional control of the ApoE hepatic control region (HCR) and the human alpha 1 antitrypsin promoter (hAAT), as well as a bovine growth hormone polyadenylation signal (gGH PA). The backbone of plasmid pAAV-hFIX16 contains the β-lactamase gene, conferring ampicillin resistance, a bacterial origin of replication, a M13/F1 origin of replication, and a fragment of bacteriophage lambda DNA. The lambda DNA increases the size of the plasmid backbone to 6,966 bp, which prevents its packaging during AAV vector production.

The recombinant AAV virions were produced using the triple transfection method described above. For the caprine rAAV virions, the VP1 coding sequence present in plasmid pHLP19 was substituted with the caprine VP1 coding sequence as described above.

After injection, retro-orbital blood was collected 1, 2, 4 (5 mice per group) and 8 weeks (2 mice per group) after injection and plasma was extracted. Mice tested with IVIG (Panglobulin: purified immunoglobulin from a pool of human serum, ZLB Bioplasma, lot# 1838-00299) were injected via the tail vein (250 μl), 24 hours before the vector injection. Human FIX was measured in the plasma samples by a hFIX ELISA.

Figure 18:
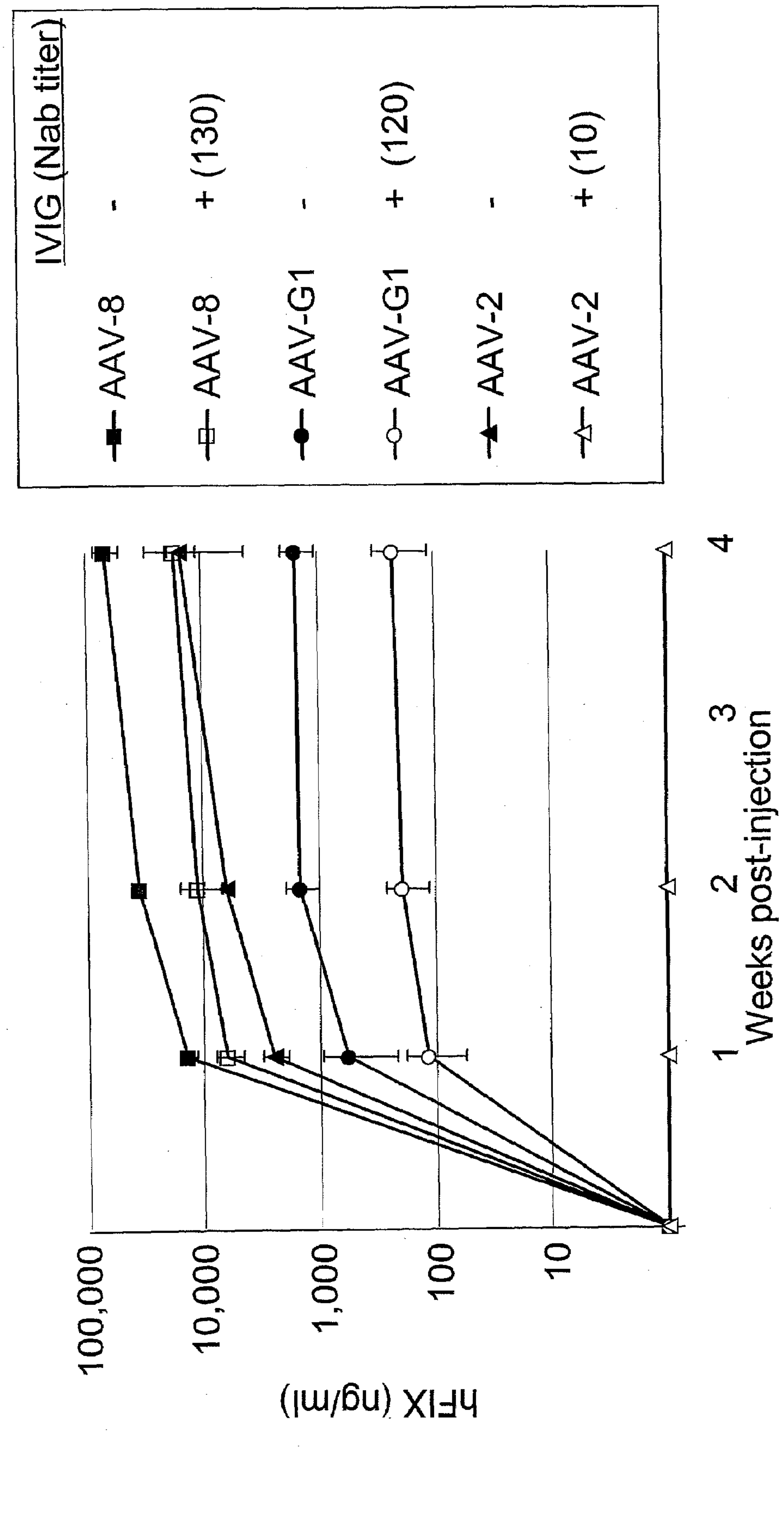
FIG. 18 shows transduction of liver in IVIG-treated SCID mice following tail vein administration of various rAAV hFIX virions.

As shown in FIG. 18, transdution of liver with the recombinant caprine AAV virions after intravenous administration was low. Higher hFIX expression was seen using the rAAV-8 virions than with the rAAV-2 virions, and rAAV-2 virions showed higher expression than the caprine rAAV virions. The caprine rAAV virions were more resistant to neutralization than the rAAV-2 virions in vivo. Human FIX expression was reduced in the caprine rAAV-injected mice with preexisting IVIG neutralizing titers of 120 while the expression of hFIX was completely blocked in the rAAV-2-injected mice with preexisting IVIG neutralizing titers of 10.

Figure 19:
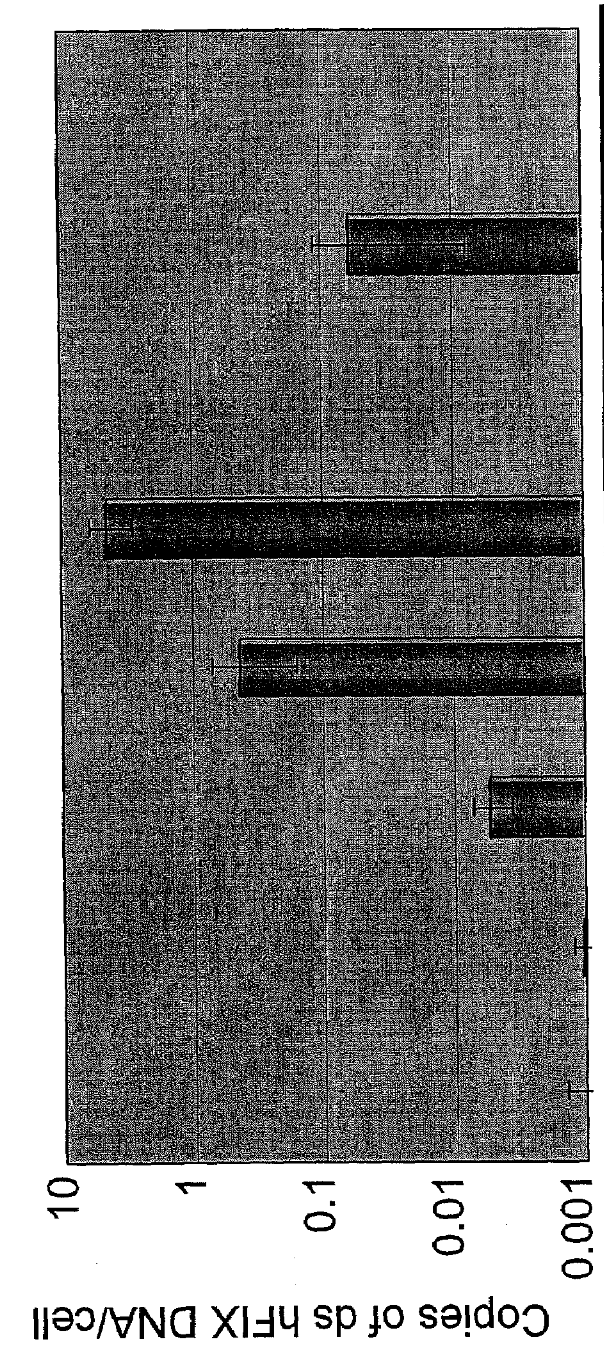
FIG. 19 shows the biodistribution of human factor IX (hFIX) follow intravenous administration of a recombinant caprine AAV vector encoding the same.

For biodistribution analysis, mice (2 mice per group) were sacrificed and organs were collected 4 weeks after vector injection. Organs collected included brain, testis, muscle (quadriceps), kidney, spleen, lung, heart, and liver. To measure hFIX, quantitative-PCR was done on DNA samples extracted from different tissues. As shown in FIG. 19, biodistribution of intravenously-administered caprine rAAV virions in male SCID mice showed that the caprine rAAV virions had lung tropism.

Example 10

Isolation and Characterization of a New Bovine AAV

Evidence of parvovirus contamination was seen in bovine adenovirus (BAV) type 8, strain Misk/67 (available from the ATCC, Manassas, Va., Accession no. VR-769) isolated from calf lungs, using techniques known in the art. This new isolate was named "AAV-C1." AAV-C1 was partially amplified by PCR, and sequenced. FIGS. 20A and 20B show the nucleotide sequence and amino acid sequence respectively, of VP1 from AAV-C1. The VP1 amino acid sequence from AAV-C1 was compared with other AAV VP1s. In particular, FIGS. 21A-21H show a comparison of the amino acid sequence of VP1 from AAV-C1 with primate AAV-1, AAV-2, AAV-3B, AAV-4, AAV-6, AAV-8, AAV-5 and caprine AAV. Conserved amino acids in the sequences are indicated by * and the accessibility of the various amino acid positions based on the crystal structure is shown. B indicates that the amino acid is buried between the inside and outside surface. I indicates the amino acid is found on the inside surface and O indicates the amino acid is found on the outside surface.

VP1 from AAV-C1 displayed approximately 76% identity with AAV-4. AAV-C1 displayed approximately 54% identity with AAV-5 VP1, with high homology in the Rep protein, the first 137 amino acids of AAV-5 VP1 and the non translated region after the stop of AAV-5 VP1 (not shown). Thus, AAV-C1 appears to be a natural hybrid between AAV-5 and AAV-4. AAV-C1 also displayed approximately 58% sequence identity with VP1s from AAV-2 and AAV-8, approximately 59% sequence identity with VP1s from AAV-1 and AAV-6, and approximately 60% sequence identity with VP1 from AAV-3B.

The sequence differences between AAV-4 and AAV-C1 were scattered throughout the capsid, unlike the differences between AAV-5 and caprine AAV (AAV-G1), wherein the changes were exclusively in the C-terminal hypervariable region of VP1. The similarity with the AAV-4 sequence was from the VP2 start to the capsid stop. AAV-C1 appears to be one of the most divergent of the mammalian AAVs with approximately 58% sequence homology with AAV-2. In particular, the bovine AAV described in Schmidt et at. was partially amplified from bovine adenovirus type 2. Comparison of the nucleotide sequence of VP1 from AAV-C1 and the bovine AAV described in Schmidt et al. showed 12 nucleotide changes 5 amino acid differences. These differences occurred at positions 334 (Q substituted for H present in AAV-C1 VP1), 464 (K substituted for N present in AAV-C1 VP1), 465 (T substituted for K present in AAV-C1 VP1), 499 (R substituted for G present in AAV-C1 VP1) and 514 (G substituted for R present in AAV-C1 VP1).

The full capsid of AAV-C1 was cloned in a plasmid that was used to produce pseudotyped AAV-2 vectors. An AAV-C1 vector containing the LacZ gene (AAV-C1-LacZ) was produced for further characterization, using the triple transfection techniques described above with the exception that the capsid sequence present in pHLP19 was replaced with the bovine capsid sequence. The titer of AAV-C1-LacZ (vg/ml) was calculated using quantitative PCR (Q-PCR) as described above. As shown in Table 17, AAV-C1 LacZ vector was produced efficiently; high titers of vector (2.45e10 vg/ml) were detected by Q-PCR. AAV-C1 LacZ vector showed efficient transduction of cells in vitro (cells expressing LacZ were present in numbers comparable to other AAVs).

TABLE 17

Q-PCR analysis of AAV-C1-LacZ vector.

| Sample | Average (vg/mL) | Std dev (vg/mL) | % CV |
|---|---|---|---|
| AAV2-lacZ | 1.11E+11 | 1.09E+10 | 9.9 |
| AAV-C1-LacZ | 2.45E+10 | 1.88E+09 | 7.7 |
| LacZ reference | 9.96E+12 | 7.11E+11 | 7.1 |

Example 11

Immunoreactivity of Bovine AAV and Comparison to Other AAVS

The neutralization activity of bovine AAV-C1 relative to primate AAV-2 was assessed using the methods described above in Example 6. Immunoreactivity was determined using a purified pooled human IgG (IVIG-8, Panglobulin Lot# 1838-00351, ZLB Bioplasma AG, Beme, Switzerland). Neutralizing assays in vitro showed that AAV-C1 was 16 times more resistant to neutralization by human IVIG than AAV-2. The lowest concentration of IVIG (mg/ml) showing more than 50% neutralization of AAV-2 was 0.2 mg/ml while AAV-C1 was 3.25 mg/ml.

Thus, methods for making and using mutant AAV virions with decreased immunoreactivity are described. Although preferred embodiments of the subject invention have been described in some detail, it is understood that obvious variations can be made without departing from the spirit and the scope of the invention as defined by the claims herein.

The invention claimed is:

1. A polynucleotide encoding a mutated adeno-associated virus (AAV) capsid protein that when present in an AAV virion imparts decreased immunoreactivity to the virion as compared to the corresponding wild-type virion, wherein the mutated AAV capsid protein comprises a substitution of one or more of the amino acids occurring at a position corresponding to a position of the AAV-2 VP2 capsid selected from the group consisting of amino acid 126, 127, 128, 130, 315, 360, 361, 365, 375, 396, 407, 437, 568, and 571.

2. The polynucleotide of claim 1, wherein the naturally occurring amino acid at the position is substituted with an alanine.

3. The polynucleotide of claim 1, wherein the protein comprises a substitution of lysine for the naturally occurring amino acid at the position corresponding to the amino acid found at position 571 of AAV-2 VP2.

4. A recombinant AAV virion comprising a mutated adeno-associated virus (AAV) capsid protein that when present in an AAV virion imparts decreased immunoreactivity to the virion as compared to the corresponding wild-type virion, wherein the mutated AAV capsid protein comprises a substitution of one or more of the amino acids occurring at a position corresponding to a position of the AAV-2 VP2 capsid selected from the group consisting of amino acid 126, 127, 128, 130, 315, 360, 361, 365, 375, 396, 407, 437, 568, and 571.

5. The recombinant AAV virion of claim 4, wherein the naturally occurring amino acid at the position is substituted with an alanine.

6. The recombinant AAV virion of claim 4, wherein the protein comprises a substitution of lysine for the naturally occurring amino acid at the position corresponding to the amino acid found at position 571 of AAV-2 VP2.

7. The recombinant AAV virion of claim 4, wherein said virion comprises a heterologous nucleic acid molecule encoding an antisense RNA or a ribozymes.

8. The recombinant AAV virion of claim 4, wherein said virion comprises a heterologous nucleic acid molecule encoding a therapeutic protein operably linked to control elements capable of directing the in vivo transcription and translation of said protein.

9. The recombinant AAV virion of claim 5, wherein said virion comprises a heterologous nucleic acid molecule encoding a therapeutic protein operably linked to control elements capable of directing the in vivo transcription and translation of said protein.

10. The recombinant AAV virion of claim 6, wherein said virion comprises a heterologous nucleic acid molecule encoding a therapeutic protein operably linked to control elements capable of directing the in vivo transcription and translation of said protein.

11. A method of delivering a recombinant AAV virion to a cell or tissue of a vertebrate subject, said method comprising:

(a) providing a recombinant AAV virion according to claim 4;

(b) delivering said recombinant AAV virion to said cell or tissue, whereby said protein is expressed at a level that provides a therapeutic effect.

12. The method of claim 11, wherein said cell or tissue is a muscle cell or tissue.

13. The method of claim 12, wherein said muscle cell or tissue is derived from skeletal muscle.

14. The method of claim 11, wherein said recombinant AAV virion is delivered into said cell or tissue in vivo.

15. The method of claim 14, wherein said recombinant AAV virion is delivered by intramuscular injection.

16. The method of claim 11, wherein said recombinant AAV virion is delivered into said cell or tissue in vitro.

17. The method of claim 11, wherein said recombinant AAV virion is delivered into the bloodstream.

18. The method of claim 17, wherein said recombinant AAV virion is delivered intravenously.

19. The method of claim 17, wherein said recombinant AAV virion is delivered intraarterially.

20. The method of claim 11, wherein said recombinant AAV virion is delivered to the liver.

21. The method of claim 11, wherein said recombinant AAV virion is delivered to the brain.

22. The polynucleotide of claim 1, wherein the protein comprises a substitution of histidine for the naturally occurring amino acid at the position corresponding to the amino acid found at position 360 of AAV-2 VP2.

23. The recombinant AAV virion of claim 4, wherein the protein comprises a substitution of histidine for the naturally occurring amino acid at the position corresponding to the amino acid found at position 360 of AAV-2 VP2.

24. The recombinant AAV virion of claim 23, wherein said virion comprises a heterologous nucleic acid molecule encoding a therapeutic protein operably linked to control elements capable of directing the in vivo transcription and translation of said protein.

* * * * *